(12) United States Patent
Meunier et al.

(10) Patent No.: US 6,403,788 B1
(45) Date of Patent: Jun. 11, 2002

(54) NON-GENOTOXIC METALLOPORPHYRINS AS SYNTHETIC CATALYTIC SCAVENGERS OF REACTIVE OXYGEN SPECIES

(75) Inventors: Bernard Meunier, Castanet; Frédéric Cosledan, Escalquens, both of (FR)

(73) Assignee: Eukarion, Inc., Bedford, MA (US)

( * ) Notice: Subject to any disclaimer, the term of this patent is extended or adjusted under 35 U.S.C. 154(b) by 0 days.

(21) Appl. No.: 09/613,891

(22) Filed: Jul. 11, 2000

(51) Int. Cl.$^7$ .................... A61K 31/555; C07D 487/22
(52) U.S. Cl. ................ 540/145; 540/145; 514/185
(58) Field of Search .................. 540/145; 514/185, 514/81

(56) References Cited

U.S. PATENT DOCUMENTS

| | | | |
|---|---|---|---|
| 4,658,023 A | 4/1987 | Shudo | 540/145 |
| 4,892,941 A | 1/1990 | Dolphin et al. | 540/145 |
| 5,077,394 A | 12/1991 | Dolphin et al. | 530/505 |
| 5,192,788 A | 3/1993 | Dixon et al. | 514/410 |
| 5,202,317 A | 4/1993 | Bruice | 514/185 |
| 5,236,914 A | 8/1993 | Meunier et al. | 514/185 |
| 5,268,371 A | 12/1993 | Mauclaire et al. | 514/185 |
| 5,284,647 A | 2/1994 | Niedballa et al. | 424/84 |
| 5,599,924 A | 2/1997 | Therien et al. | 540/145 |
| 5,674,467 A | 10/1997 | Maier et al. | 424/1.65 |
| 5,747,026 A | 5/1998 | Crapo et al. | 424/94.3 |
| 5,760,216 A | 6/1998 | Chorghade et al. | 540/145 |
| 5,994,339 A | 11/1999 | Crapo et al. | 514/185 |
| 6,127,356 A | 10/2000 | Crapo et al. | 514/185 |

FOREIGN PATENT DOCUMENTS

| | | |
|---|---|---|
| EP | 0 337 598 A2 | 10/1989 |
| WO | WO95/10185 | 4/1995 |
| WO | WO96/09053 | 3/1996 |
| WO | WO96/40223 | 12/1996 |
| WO | WO99/55388 | 11/1999 |
| WO | WO 00/75144 | 12/2000 |
| WO | WO 01/26655 | 4/2001 |

OTHER PUBLICATIONS

D. Deniaud et al, New. J. Chem. (1998) 901.*
M. Brockhart et al. Organometallics 11 (1992) 3920–3922.*
S. Melov Ann. NY Acad. Sci. 908 (2000) 219–25 (Medline Abstract).*
F. Müller et al. Eur. J. Clin. Invest. 30 (2000) 905–914.*

Bernadou, J., et al., "Potassium Monopersulfate and a Water–Soluble Manganese Porphyrin Complex, [Mn(T-MPyP0] (OAC)$_5$, as an Efficient Reagent for the Oxidative Cleavage of DNA," Biochemistry 28:7268–7275 (1989).

Vialas, C., et al., "Guanine Oxidation in Double–Stranded DNA by Mn–TMPyP/KHSO$_5$, 8–Dihydroxy–7, 8–dihydroguanine Residue as a Key Precursor of Imidazolone and Parabanic Acid Derivatives," J. Am. Chem. Soc. 122:2157–2167 (2000).

Meunier, B., "Metalloporphyrins as Versatile Catalysts for Oxidation Reactions–and Oxidative DNA Cleavage," Chem. Rev. 92:1411–1456 (1992).

Batinic–Haberle, I.B., et al., "Relationship Among Redox Potentials, Proton Dissociation Constants of Pyrrolic Nitrogens, and In Vivo and In Vitro Superoxide Dismutating Activities of Manganese(III) and Iron(III) Water–Soluble Porphyrins," Inorg. Chem. 38:4011–4022 (1999).

Patel, M., et al., "Metalloporphyrin Class of Therapeutic Catalytic Antioxidants," TiPS 20:359–364 (1999).

Doctrow, S.R., et al., "Salen–Manganese Complexes: Combined Superoxide Dismutase/Catalase Mimics with Broad Pharmacological Efficacy," Advances in Pharmacology 38:247–269 (1997).

Crapo, J., "Role of EC–SOD in Modulating Responses to Cerebral Ischemia Reperfusion (Stroke)," International Society of Antioxidants in Nutrition & Health (2$^{nd}$ International Conference) Pasteur Institute, 34–35 (2000).

Song, R., et al., "Anti–HIV Activities of Anionic Metalloporphyrins and Related Compounds", Antiviral Chemistry and Chemotherapy, 8(2) : 85–97 (1997).

Rocha Gonsalves, A.M.d'A., et al., "Sulphonamide Porphyrins in the Biomimetic Oxidations by H$_2$O$_2$. An Efficient Two–phase System, " An. Quim. Int. Ed., 92(6) :375–380 (1996).

* cited by examiner

Primary Examiner—Richard L. Raymond
Assistant Examiner—Kahsay Habte
(74) Attorney, Agent, or Firm—Hamilton, Brook, Smith & Reynolds, P.C.

(57) ABSTRACT

This invention relates to compounds which are non-genotoxic metalloporphyrins. These compounds are synthetic catalytic scavengers of reactive oxygen chemical species. The invention also relates to pharmaceutical compositions comprising these compounds and to methods of use of these compounds for preventing or arresting free radical associated diseases or conditions.

39 Claims, 2 Drawing Sheets

Histogram representation of the cleavage of ΦX 174DNA Plasmid (Form I) in the presence of Ascorbate and $H_2O_2$.

NON-GENOTOXIC METALLOPORPHYRINS AS SYNTHETIC CATALYTIC SCAVENGERS OF REACTIVE OXYGEN SPECIES

BACKGROUND OF THE INVENTION

Molecular oxygen is an essential nutrient for nonfacultative aerobic organisms, including humans. Oxygen, although essential for aerobic metabolism, can be converted to poisonous metabolites, such as superoxide anion and hydrogen peroxide, collectively known as reactive oxygen species. Excessive concentrations of various forms of oxygen and of free radicals can have serious adverse effects on living systems, including the peroxidation of membrane lipids, the hydroxylation of nucleic acid bases, and the oxidation of sulfhydryl groups and other sensitive moieties in proteins. If uncontrolled, mutations and cell death result.

Biological antioxidants include well-defined naturally occurring metalloenzymes, such as superoxide dismutase (SOD), catalase (CAT), and selenium glutathione peroxidase, as well as the enzyme, phospholipid hydroperoxide glutathione peroxidase. A large number of diseases or degenerative processes are related to disorders with metalloenzymes involved in the detoxification of reactive oxygen species derived from dioxygen reduction. The role of these metalloenzymes has been demonstrated with animals underexpressing SOD or CAT enzymes. In addition, the induction of nitric oxide-dependent apoptosis in motor neurons by zinc-deficient superoxide dismutase has recently been shown (Estévez et al. (2000), Science, 286:2498–2500).

Obstacles exist for the use of recombinant metalloenzymes in therapy including: solution instability, limited cellular accessibility, immunogenicity, short half-lives, cost of production and proteolytic digestion. These synthetic catalytic scavengers must be stable in physiological conditions and, in particular, the metal should be strictly inserted within the ligand to avoid any demetallation and trapping of the metal ion by serum proteins. These synthetic catalytic scavengers must also be soluble in water at pH 7.0. Avoiding synthetic molecules that lead to DNA cleavage is an additional concern.

Consequently, there is a need for new synthetic transition metal complexes with the ability to catalyze the dismutation of the reactive oxygen species derived from the non-controlled reduction of dioxygen. The need exists for providing non-genotoxic water soluble metallophorphyrin derivatives able to act as SOD and CAT mimics without creating oxidative damage of DNA.

SUMMARY OF THE INVENTION

The present invention relates to compounds which are effective as synthetic catalytic scavengers for reactive oxygen species. The compounds are effective as superoxide dismutase (SOD), and/or catalase (CAT), and/or peroxidase (POD) mimetics which, accordingly, have antioxidant and/or free radical scavenging properties and function in vivo as antioxidants. In particular, the present invention relates to non-genotoxic metalloenzyme mimetics, pharmaceutical formulations containing them, methods for their preparation and the use of such compounds in prophylaxis and therapy for diseases and degenerative processes resulting from reactive oxygen species.

The metallophorphyrin derivatives of this invention can be represented by Structural Formula I:

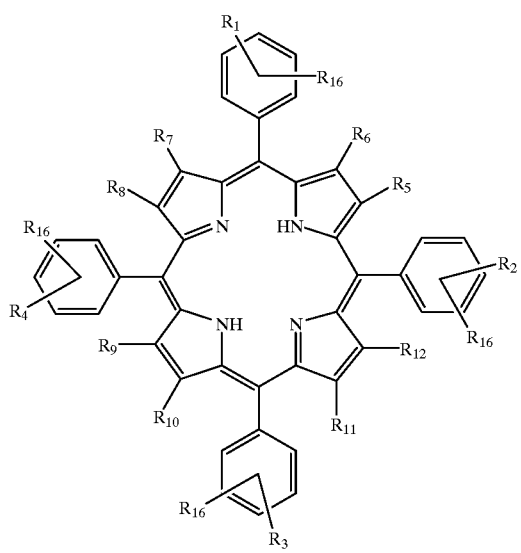

In a preferred embodiment, Structural Formula I is a complex containing a metal ion, preferably a transition metal such as manganese or iron. In Structural Formula I, $R_1$, $R_2$, $R_3$ and $R_4$ are the same or different and are each a group of the formula:

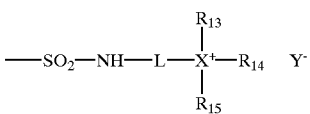

where L is a linker of about 2 to about 12 atoms in length. The atoms within the linker are carbon atoms optionally interspersed with from 1 to 4 heteroatoms selected from the group consisting of oxygen, nitrogen and sulfur. Preferably L is a linear $C_2$–$C_6$ alkylene group, more preferably ethylene, X is nitrogen or phosphorus; $R_{13}$, $R_{14}$ and $R_{15}$ are each, independently, hydrogen, alkyl or arylalkyl; Y- is a monovalent anion; $R_5$, $R_6$, $R_7$, $R_8$, $R_9$, $R_{10}$, $R_{11}$ and $R_{12}$ are each independently selected from the group consisting of hydrogen, alkyl and halo; and each $R_{16}$ independently represents one or more substituents independently selected from the group consisting of hydrogen, hydroxy, halo and alkyl.

Herein, halo is, for example, fluoro, chloro, bromo, iodo; preferably it is fluoro, chloro or bromo.

The counter monovalent anion Y can represent any suitable anion with which the complex of Structural Formula I can be formed. Suitable examples include chloride, hydroxide and acetate, preferably chloride or acetate.

In another embodiment, the invention relates to methods of preparing compounds of Structural Formula I.

In another aspect, the invention provides methods of using the compounds of Structural Formula I for prophylaxis or treatment of a free radical associated disease or condition in a mammal.

In yet another aspect, the invention provides pharmaceutical formulations comprising one or more pharmaceutically acceptable carriers, diluents or excipients and a therapeutically effective amount of compound represented by Structural Formula I.

In yet another embodiment, the invention relates to methods of treating, preventing or arresting free radical associated diseases or conditions comprising administering to an individual in need thereof a therapeutically effective amount of a compound represented by Structural Formula I.

DETAILED DESCRIPTION OF THE INVENTION

Figure 1:
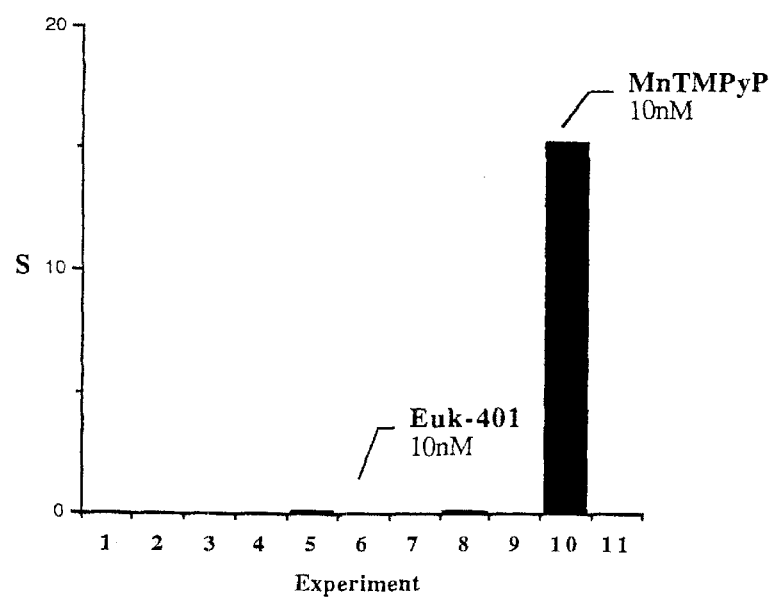
FIG. 1 is a histogram representation of the cleavage of ΦX 174 DNA Plasmid (Form I) in the presence of $KHSO_5$ when a compound of this invention or a control compound (MnTMPyP) is present.

Aerobic cells generally contain a number of defenses against the deleterious effects of oxyradicals and their reaction products. Superoxide dismutases (SODs) catalyze the reaction:

$$2O_2^{\cdot-} + 2H^+ \rightarrow O_2 + H_2O_2$$

which removes superoxide and forms hydrogen peroxide. $H_2O_2$ is not a radical, but it is toxic to cells. It is removed by the enzymatic activities of catalase or glutathione peroxidase (GSH-Px). Catalase catalyzes the reaction:

$$2H_2O_2 \rightarrow 2H_2O + O_2$$

thereby removing hydrogen peroxide and forming water and oxygen. GSH-Px removes hydrogen peroxide by using it to oxidize reduced glutathione (GSH) into oxidized glutathione (GSSG) according to the following reaction:

$$2GSH + H_2O_2 \rightarrow GSSG + 2H_2O$$

Other enzymes, such as phospholipid hydroperoxide glutathione peroxidase (PLOOH-GSH-Px), convert reactive phospholipid hydroperoxides, free fatty acid hydroperoxides, and cholesterol hydroperoxides to corresponding harmless fatty acid alcohols. Glutathione S-transferases also participate in detoxifying organic peroxides. In the absence of these enzymes and in presence of transition metals, such as iron or copper, superoxide and hydrogen peroxide can participate in the following reactions which generate the extremely reactive hydroxyl radical HO•:

$$O_2^{\cdot-} + Fe^{3+} \rightarrow O_2 + Fe^{2+}$$

$$H_2O_2 + Fe^{2+} \rightarrow HO\cdot + HO^- + Fe^{3+}$$

In addition to enzymatic detoxification of free radicals and oxidant species, a variety of low molecular weight antioxidants such as glutathione, ascorbate, tocopherol, ubiquinone, bilirubin, and uric acid serve as naturally-occurring physiological antioxidants (Krinsky, NI (1992) *Proc. Soc. Exp. Biol. Med.* 200: 248–54). Carotenoids are another class of small molecule antioxidants that have been implicated as protective agents against oxidative stress and chronic diseases. Canfield et al. (1992) *Proc. Soc. Exp. Biol. Med.* 200: 260 summarize reported relationships between such carotenoids and various chronic diseases, including coronary heart disease, cataracts, and cancer. Carotenoids have also been shown to dramatically reduce the incidence of certain premalignant conditions, such as leukoplakia, in some patients.

In an effort to prevent the damaging effects of oxyradical formation during reoxygenation of ischemic tissues, a variety of antioxidants have been used. One strategy for preventing oxyradical-induced damage is to inhibit the formation of oxyradicals such as superoxide. Iron ion chelators, such as desferrioxamine (also called deferoxamine or Desferal) and others, inhibit iron ion-dependent HO• generation and thus act as inhibitors of free radical formation (Gutteridge et al. (1979) *Biochem. J.* 184: 469; Halliwell B (1989) *Free Radical Biol. Med.* 7: 645; Van der Kraaij et al. (1989) *Circulation* 80: 158). Amino-steroid-based antioxidants such as the 21-aminosteroids termed "lazaroids" (e.g, U74006F) have also been proposed as inhibitors of oxyradical formation. Desferrioxamine, allopurinol, and other pyrazolopyrimidines such as oxypurinol, have also been tested for preventing oxyradical formation in a myocardial stunning model system (Bolli et al. (1989) *Circ. Res.* 65: 607) and following hemorrhagic and endotoxic shock (DeGarvilla et al. (1992) *Drug Devel. Res.* 25:139). However, each of these compounds has notable drawbacks for therapeutic usage. For example, deferoxamine is not an ideal iron chelator and its cellular penetration is quite limited.

Another strategy for preventing oxyradical-induced damage is to catalytically remove oxyradicals such as superoxide once they have been formed. Superoxide dismutase and catalase have been extensively explored, with some success, as protective agents when added to reperfusates in many types of experiments or when added when ischemia is imminent (reviewed in Gutteridge JMC and Halliwell B (1990) op. cit.). The availability of recombinant superoxide dismutase has allowed more extensive evaluation of the effect of administering SOD in the treatment or prevention of various medical conditions including reperfusion injury of the brain and spinal cord (Uyama et al. (1990) *Free Radic. Biol. Med.* 8: 265; Lim et al. (1986) *Ann. Thorac. Surg.* 42: 282), endotoxemia (Schneider et al. (1990) *Circ. Shock* 30: 97; Schneider et al. (1989) *Prog. Clin. Biol. Res.* 308: 913), myocardial infarction (Patel et al. (1990) *Am. J. Physiol.* 258: H369; Mehta et al. (1989) *Am. J. Physiol.* 257: H1240; Nejima et al. (1989) *Circulation* 79: 143; Fincke et al (1988) *Arzneimittelforschung* 38: 138; Ambrosio et al. (1987) *Circulation* 75: 282), and osteoarthritis and intestinal ischemia (Vohra et al (1989) *J. Pediatr. Surg.* 24: 893; Flohe L. (1988) *Mol. Cell. Biochem.* 84: 123). Superoxide dismutase also has been reported to have positive effects in treating systemic lupus erythematosus, Crohn's disease, gastric ulcers, oxygen toxicity, burned patients, renal failure attendant to transplantation, and herpes simplex infection.

An alternative strategy for preventing oxyradical-induced damage is to scavenge oxyradicals such as superoxide once these have been formed, typically by employing small molecule scavengers which act stoichiometrically rather than catalytically. Congeners of glutathione have been used in various animal models to attenuate oxyradical injury. For example, N-2-mercaptopropionylglycine has been found to confer protective effects in a canine model of myocardial ischemia and reperfusion (Mitsos et al. (1986) *Circulation* 73: 1077). N-acetylcysteine ("Mucomyst") has been used to treat endotoxin toxicity in sheep (Bernard et al. (1984) *J. Clin. Invest.* 73: 1772). Dimethyl thiourea (DMTU) and butyl-α-phenylnitrone (BPN) are believed to scavenge the hydroxyl radical, HO•, and have been shown to reduce ischemia-reperfusion injury in rat myocardium and in rabbits (Vander Heide et al. (1987) *J. Appl. Physiol.* 63: 2426). Mannitol has also been used as a free radical scavenger to reduce organ injury during reoxygenation (Fox RB (1984) *J. Clin. Invest.* 74: 1456; Ouriel et al. (1985) *Circulation* 72: 254).

Thus, application of inhibitors of oxyradical formation and/or enzymes that remove superoxide and hydrogen peroxide and/or small molecules that act as oxyradical scavengers have all shown promise for preventing re-oxygenation damage present in a variety of ischemic pathological states and for treating or preventing various disease states associated with free radicals. However, the molecular constituents of each of these categories exhibit a number of deleterious properties. For example, inhibitors of oxyradical formation typically chelate transition metals which are used in essential enzymatic processes in normal physiology and respiration; moreover, even at very high doses, these inhibitors do not completely prevent oxyradical formation. Superoxide dismutases and catalase are large polypeptides which are expensive to manufacture, do not penetrate cells or the blood-brain barrier, and generally require parenteral routes of administration. Free radical scavengers act stoichiometrically and are thus easily depleted and must be administered in high dosages to be effective. There are other strong limitations for the use of recombinant metalloenzymes in therapy including solution instability, limited cellular accessibility, immunogenicity, short half-lives, genotoxicity, cost of production and proteolytic digestion.

The complex formed between the chelator desferrioxamine and manganese has SOD activity and has shown some activity in biological models but the instability of the metal ligand complex apparently precludes its pharmaceutical use. The metal ligand must be strictly inserted within the ligand to avoid any demetallation and trapping by serum proteins, especially ceruloplasmin and albumin.

The cationic metalloporphyrins synthesized by Fridovich et al., (*Inorg. Chem.* 38: 4011–4022, (1999)) are SOD mimics. Of these 5, 10, 15, 20 meso-tetrakis(4-methylpyridiniumyl)porphyrinato-manganese (III), (Mn-TMPyP), is also a powerful oxidative DNA cleaver, able to generate DNA damage at nanomolar concentrations (Bernadou et al., *Biochemistry*, 28:7268–7275 (1989), Vialas, C. et al, *J. Am. Chem. Soc.*, 122: 2157–2167 (2000), Meunier, B., *Chem Rev*, 92:1411–1456 (1992)).

A genotoxic compound is able to cause damage to double-stranded DNA and compounds can be compared to a reference. Known DNA cleavers such as Bleomycin, an anticancer agent, is a typical reference. The DNA cleavage activity is quantified in terms of the number of single-strand breaks per DNA molecule according to the equation $S = 4 \ln Io/I$, $Io = \%$ form I in the DNA control, and $I = \%$ form I (supercoiled DNA) in the test material. (see Bernadou et al., *Biochemistry*, 28: 7268–7275, (1989)). As used herein, the term "non-genotoxic" shall apply to compounds, which when tested as in Example 8, yield S values of less than 1 when the compounds are at a concentration of equal to or less than 1000 nM and $KHSO_5$ is present at a concentration of equal to or less than 100 $\mu M$.

The present invention relates to the discovery of compounds which are synthetic non-genotoxic, soluble SOD and CAT mimetics. These compounds offer a significant advantage, compared to known reactive oxygen scavenger compounds currently in use, due to their water solubilities, metal entrapment caging effects, longer half lives, and non-genotoxic properties. In particular, some complexes of the present invention have sterically hindered phenyl substituents at the meso positions to avoid the formation of μ-oxo dimers during catalytic cycles (Meunier, B., *Chemical Review Articles* 92:1411–1456 (1992), Vialas, et al., *J. Am. Chem. Soc.* 122:2157–2167 (2000), Bernadou, J. et al., *Biochemistry*, 28:7268–7275 (1989)).

In one embodiment, the invention relates to compounds of Structural Formula I:

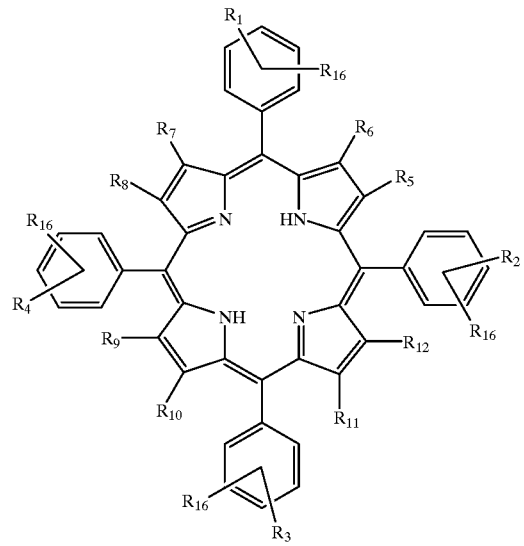

In a preferred embodiment, Structural Formula I is a complex containing a metal ion, preferably a transition metal such as manganese or iron. In Structural Formula I, $R_1$, $R_2$, $R_3$ and $R_4$ are the same or different and are each a group of the formula:

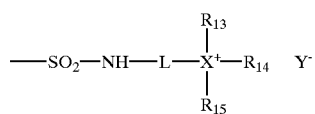

where L is a linker of about 2 to about 12 atoms in length. The atoms within the linker are carbon atoms optionally interspersed with from 1 to 4 heteroatoms selected from the group consisting of oxygen, nitrogen and sulfur; X is nitrogen or phosphorus; $R_{13}$, $R_{14}$ and $R_{15}$ are each, independently, hydrogen, alkyl or arylalkyl; Y- is a monovalent anion; $R_5$, $R_6$, $R_7$, $R_8$, $R_9$, $R_{10}$, $R_{11}$ and $R_{12}$ are each independently selected from the group consisting of hydrogen, alkyl and halo; and each $R_{16}$ independently represents one or more substituents independently selected from the group consisting of hydrogen, hydroxy, halo and alkyl.

For the purposes of the present invention, the term "alkyl" refers to a straight chain or branched hydrocarbon group. Halo is, for example, fluoro, chloro, bromo, iodo; preferably it is fluoro, chloro or bromo. $C_2$–$C_{20}$ alkyl refers to a straight chain or branched hydrocarbon group, L is a linker of about 2 to about 12 atoms in length. The atoms within the linker are carbon atoms optionally interspersed with from 1 to 4 heteroatoms selected from the group consisting of oxygen, nitrogen and sulfur.

The counter monovalent anion Y can represent any suitable anion with which the complex of Structural Formula I can be formed. Suitable examples include chloride, hydroxide and acetate, preferably chloride or acetate.

In an embodiment, $R_1$, $R_2$, $R_3$ and $R_4$ are the same.

In another embodiment, $R_5$, $R_6$, $R_7$, $R_8$, $R_9$, $R_{10}$, $R_{11}$ and $R_{12}$ are each hydrogen.

In one embodiment, $R_1$, $R_2$, $R_3$ and $R_4$ are the same and $R_{13}$, $R_{14}$ and $R_{15}$ are each independently selected from the group consisting of hydrogen and linear and branched $C_1$–$C_{20}$ alkyl.

In still another embodiment, L is selected from group consisting of linear or branched $C_2$–$C_{12}$ alkylene and linear or branched alkylene optionally interspersed at one or more positions by a heteroatom and $R_{13}$, $R_{14}$ and $R_{15}$ are each, independently, hydrogen, methyl or ethyl.

In another embodiment, $R_1$, $R_2$, $R_3$ and $R_4$ are the same and $R_{13}$ and $R_{14}$ are each independently, methyl or ethyl and $R_{15}$ is hydrogen.

In another embodiment, $R_5$, $R_6$, $R_7$, $R_8$, $R_9$, $R_{10}$, $R_{11}$ and $R_{12}$ are each hydrogen and L is a linear $C_2$–$C_6$ alkylene group; for example, ethylene.

In another embodiment, $R_1$, $R_2$, $R_3$ and $R_4$ are the same and $R_{16}$ represents hydrogen.

In another embodiment, $R_1$, $R_2$, $R_3$ and $R_4$ are the same and are each connected to the 3 position of the phenyl ring, and $R_{16}$ represents methyl groups at the 2, 4 and 6 positions of the phenyl ring.

In another embodiment, $R_1$, $R_2$, $R_3$ and $R_4$ are the same, $R_5$, $R_6$, $R_7$, $R_8$, $R_9$, $R_{10}$, $R_{11}$ and $R_{12}$ are each hydrogen, $R_{16}$ represents hydrogen, $R_1$, $R_2$, $R_3$ and $R_4$ are connected to the 3 or 4 position of the phenyl ring, L is an ethylene group and $R_{13}$, $R_{14}$ and $R_{15}$ are each independently hydrogen, methyl or ethyl.

Where isomers of the metalloporphyrin compounds of the present invention are possible, all such isomers are within the scope of the invention; i.e., ortho, meta, and para isomers.

The labile axial positions of the water-soluble metalloporphyrins, namely Structural Formulas: I, II, III, IV, V, VI, VII, and VIII, can be occupied by a water molecule.

The invention further relates to the compound represented by Structural Formula II.

Structural Formula II

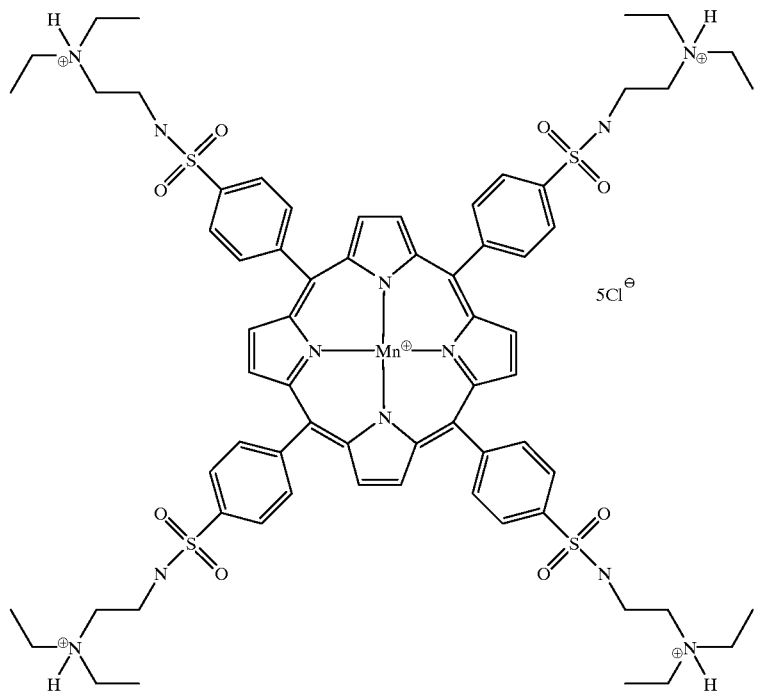

The invention also relates to the compound represented by the Structural Formula III.
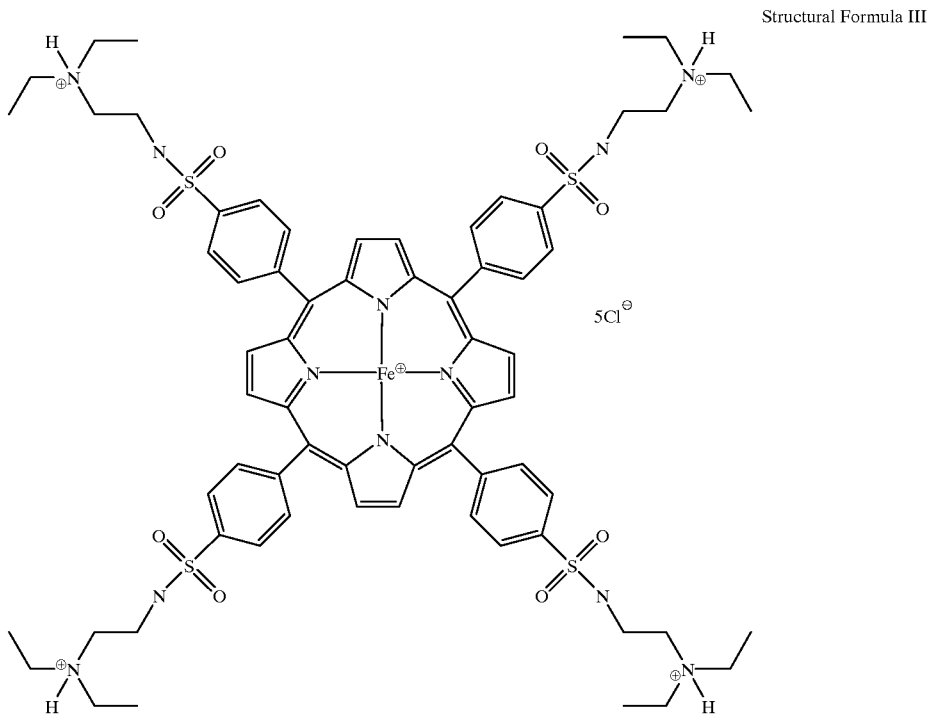
Structural Formula III
The invention further relates to the compound represented by Structural Formula IV.
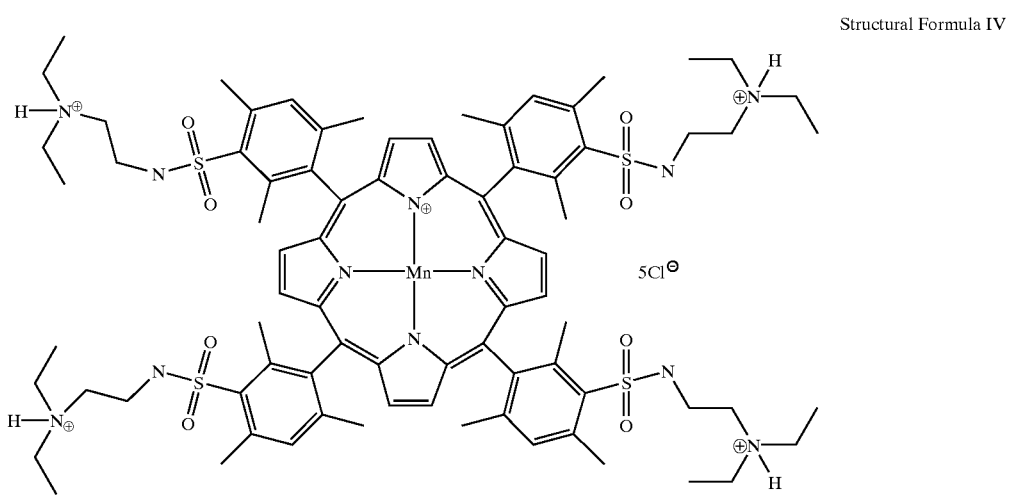
Structural Formula IV
The invention further relates to the compound represented by Structural Formula V.

Structural Formula V
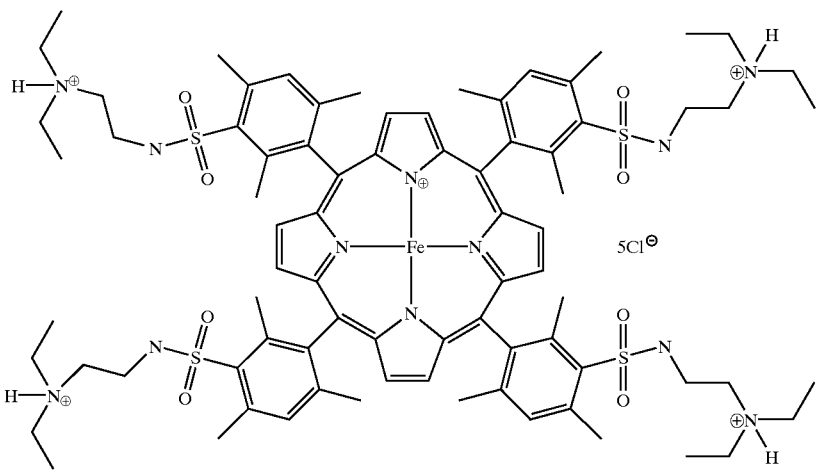
The invention further relates to the compound represented by Structural Formula VI.
Structural Formula VI
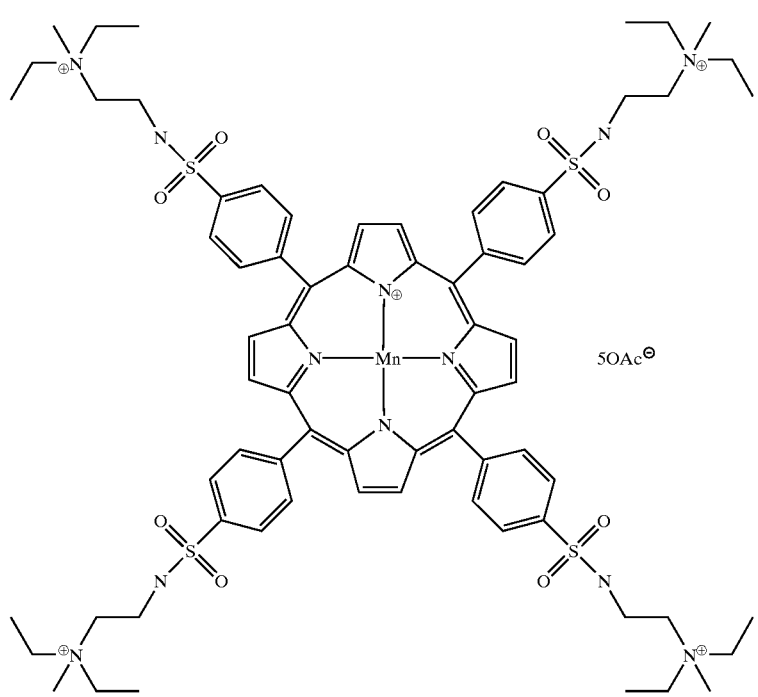
The invention further relates to the compound represented by Structural Formula VII.

Structural Formula VII

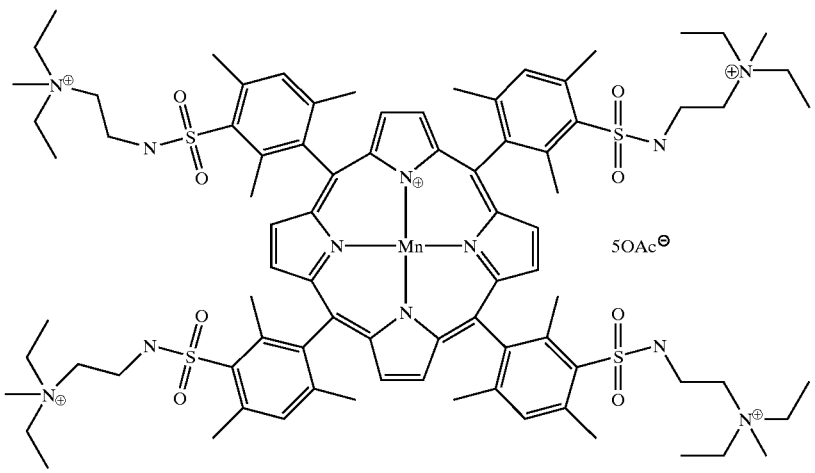

The invention further relates to the compound represented by Structural Formula VIII.

Structural Formula VIII

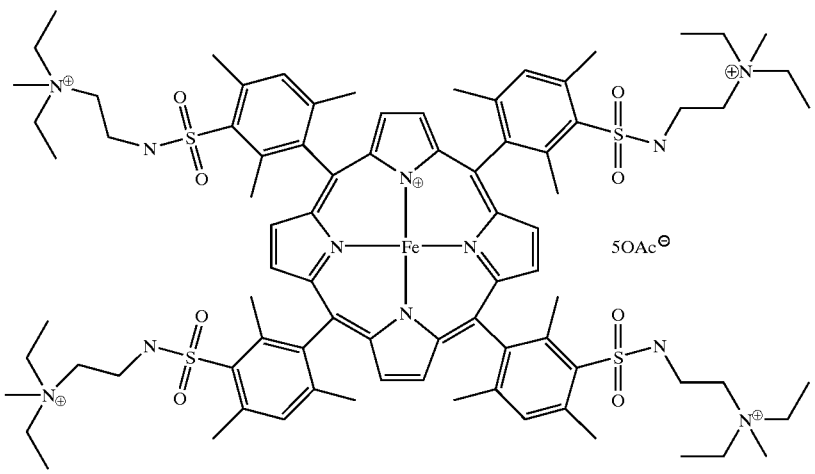

In a particularly preferred embodiment there is provided a ligand of Structural Formula I as defined above and selected from the group:
meso-tetrakis[4-(N-(2-(N,N-dimethylamino)ethyl) aminosulfonyl)phenyl]porphyrinato;
meso-tetrakis[4-(N-(2-(N,N-dimethylammonio)ethyl) aaminosulfonyl)phenyl]porphyrinato $A^{4-}$;
meso-tetrakis[4-(N-(2-(N,N,N-trimethylammonio)ethyl) aminosulfonyl)phenyl]porphyrinato $A^{4-}$;
meso-tetrakis[4-(N-(2-(N,N-diethylamino)ethyl) aminosulfonyl)phenyl]porphyrinato;
meso-tetrakis[4-(N-(2-(N,N-diethylammonio)ethyl) aminosulfonyl)phenyl]porphyrinato; $A^{4-l;}$
meso-tetrakis[4-(N-(2-(N,N,N-triethylammonio)ethyl) aminosulfonyl)phenyl]porphyrinato $A^{4-}$;
meso-tetrakis[4-(N-(2-(N,N,N-ethyldimethylammonio) ethyl)aminosulfonyl)phenyl]porphyrinato $A^{4-}$;
meso-tetrakis[4-(N-(2-(N,N,N-diethylmethylammonio) ethyl)aminosulfonyl)phenyl]porphyrinato $A^{4-}$;
meso-tetrakis[3-(N-(2-(N,N-dimethylamino)ethyl) aminosulfonyl)-2,4,6-trimethylphenyl]porphyrinato;
meso-tetrakis[3-(N-(2-(N,N-dimethylammonio)ethyl) aminosulfonyl)-2,4,6-trimethylphenyl]porphyrinato $A^{4-}$;
meso-tetrakis[3-(N-(2-(N,N-diethylammonio)ethyl) aminosulfonyl)-2,4,6-trimethylphenyl]porphyrinato $A^{4-}$;

meso-tetrakis[3-(N-(2-(N,N-diethylamino)ethyl) aminosulfonyl)-2,4,6-trimethylphenyl]porphyrinato;
meso-tetrakis[3-(N-(2-(N,N,N-triethylammonio)ethyl) aminosulfonyl)-2,4,6-trimethylphenyl]porphyrinato $A^{4-}$;
meso-tetrakis[3-(N-(2-(N,N,N-trimethylammonio)ethyl) aminosulfonyl)-2,4,6-trimethylphenyl]porphyrinato $A^{4-}$;
meso-tetrakis[3-(N-(2-(N,N-ethyldimethylammonio)ethyl) aminosulfonyl)-2,4,6-trimethylphenyl]porphyrinato $A^{4-}$;
meso-tetrakis[3-(N-(2-(N,N,N-diethylmethylammonio) ethyl)aminosulfonyl)-2,4,6-trimethylphenyl]porphyrinato $A^{4-}$;
meso-tetrakis[4-(N-(2-(N,N-ethylmethylamino)ethyl) aminosulfonyl)phenyl]porphyrinato;
meso-tetrakis[4-(N-(2-(N,N-ethylmethylammonio)ethyl) aminosulfonyl)phenyl]porphyrinato $A^{4-}$;
meso-tetrakis[3-(N-(2-(N,N-ethylmethylammonio)ethyl) aminosulfonyl)-2,4,6-trimethylphenyl]porphyrinato $A^{4-}$; and
meso-tetrakis[3-(N-(2-(N,N-ethylmethylammonio)ethyl) aminosulfonyl)-2,4,6-trimethylphenyl]porphyrinato $A^{4-}$;
meso-tetrakis[4-(N-(2-(N,N-dimethylphosphonio)ethyl) aminosulfonyl)phenyl]porphyrinato;

meso-tetrakis[4-(N-(2-(N,N-diethylphosphonio)ethyl) aminosulfonyl)phenyl]porphyrinato;

meso-tetrakis[3-(N-(2-(N,N-dimethylphosphonio)ethyl) aminosulfonyl)-2,4,6-trimethylphenyl]porphyrinato;

meso-tetrakis[3-(N-(2-(N,N-diethylphosphonio)ethyl) aminosulfonyl)-2,4,6-trimethylphenyl]porphyrinato $A^{4-}$;

meso-tetrakis[3-(N-(2-(N,N-diethylphosphonio)ethyl) aminosulfonyl)-2,4,6-trimethylphenyl]porphyrinato; and meso-tetrakis[4-(N-(2-(N,N-ethylmethylphosphonio)ethyl) aminosulfonyl)phenyl]porphyrinato;

or a complex thereof with a metal ion, wherein $A^{4-}$ represents from 1 to 4 anions having a total electronic charge of $4^-$.

While it is possible for the compounds of the present invention to be administered as the complex per se, it is preferred to present the compounds or the complexes in the form of a pharmaceutical formulation.

Pharmaceutical formulations can be adapted for administration by any appropriate route, for example by the oral (including buccal or sublingual), rectal, nasal, topical (including buccal, sublingual or transferal), vaginal or parenteral (including subcutaneous, intramuscular, intravenous or intradermal) route. Such formulations can be prepared by any method known in the art of pharmacy, for example by bringing into association the active ingredient with the carrier(s), diluent(s) or excipient(s).

Thus, according to a further aspect of the present invention there is provided a pharmaceutical formulation comprising at least one compound of Structural Formula I together with one or more pharmaceutically acceptable carriers, diluents or excipients.

Pharmaceutical formulations may be presented in unit dose forms containing a predetermined amount of active ingredient per unit dose. Such a unit may contain for example 1 µg to 10 µg, preferably 0.01 mg to 1000 mg, more preferably 0.1 mg to 250 mg, of a compound of Structural Formula I depending on the condition being treated, the route of administration and the age, weight and condition of the patient.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions. Typically, tablet or capsules will be prepared to contain from 1 mg to 1000 mg, preferably 2.5 mg to 250 mg of active ingredient per unit dose.

Pharmaceutical formulations adapted for transferal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas; rectal ointments and foams may also be employed.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurized aerosols, nebulizers or insufflators. Spray compositions may, for example, be formulated as aerosols delivered from pressurized packs, such as a metered dose inhaler, with the use of a suitable liquified propellant. Capsules and cartridges for use in an inhaler or insufflator, for example gelatine, may be formulated containing a powder mix for inhalation of a compound of the invention and a suitable powder base such as lactose or starch. Each capsule or cartridge may generally contain between 1 µg–10 mg of the compound of Structural Formula I. Aerosol formulations are preferably arranged so that each metered dose or "puff" of aerosol contains 1 µg–2000 µg, preferably about 1 µg–500 µg of a compound of Structural Formula I. Administration may be once daily or several times daily, for example 2, 3, 4 or 8 times, giving for example 1, 2 or 3 doses each time. The overall daily dose with an aerosol will generally be within the range 10 µg–10 mg, preferably 100 µg–2000 µg. The overall daily dose and the metered dose delivered by capsules and cartridges in an inhaler or insufflator will generally be double those with aerosol formulations.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain the antioxidants as well as buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

As used herein, an "antioxidant" is a substance that, when present in a mixture or structure containing an oxidizable substrate biological molecule, significantly delays or prevents oxidation of the substrate biological molecule. Antioxidants can act by scavenging biologically important reactive free radicals or other reactive oxygen species ($O_2^{\bullet-}$, $H_2O_2$, HO•, HOCl, ferryl, peroxyl, peroxynitryl, and alkoxyl), or by preventing their formation, or by catalytically converting the free radical or other reactive oxygen species to a less reactive species. An antioxidant compound of the present invention generally has detectable SOD, CAT and/or POD activity. A compound of the present invention has antioxidant activity if the complex, when added to a cell culture or assay reaction, produces a detectable decrease in the amount of a free radical, such as superoxide, or a nonradical reactive oxygen species, such as hydrogen peroxide, as compared to a parallel cell culture or assay reaction that is not treated with the complex. The relative amount of free radical species is often determined by detection of a secondary indicator (e.g., an oxidized substrate; peroxidized lipid, cytochrome C).

As used herein, "free radical-associated diseases or conditions" refers to a pathological condition of an individual that results at least in part from the production of or exposure to free radicals, particularly oxyradicals, and other reactive oxygen species in vivo. Most pathological conditions are multifactorial, in that multiple factors contributing to the disease state are present, and that assigning or identifying the predominant causal factor(s) for any individual pathological condition is frequently extremely difficult. For these reasons, the term "free radical associated disease" encompasses pathological states that are recognized in the art as being conditions wherein damage from free radicals or reactive oxygen species is believed to contribute to the pathology of the disease state, or wherein administration of a free radical inhibitor (e.g., desferrioxamine), scavenger (e.g., tocopherol, glutathione), or catalyst (e.g., SOD, catalase) is shown to produce a detectable benefit by decreasing symptoms, increasing survival, or providing other detectable clinical benefits in treating or preventing the pathological state. For example, but not in limitation, the following disease states discussed herein are considered free radical-associated diseases: ischemic reperfusion injury, inflammatory diseases, systemic lupus erythematosus, myocardial infarction, stroke, traumatic hemorrhage, spinal cord trauma, Crohn's disease, autoimmune diseases (e.g., rheumatoid arthritis, diabetes), cataract formation, uveitis, emphysema, gastric ulcers, oxygen toxicity, neoplasia, undesired cell apoptosis, radiation sickness, and other pathological states discussed above, such as toxemia and acute lung injury. Such diseases can include "apoptosis-related ROS" which refers to reactive oxygen species (e.g., $O_2^{\bullet-}$, HOOH) which damage critical cellular components (e.g., lipid peroxidation) in cells stimulated to undergo apoptosis. Such apoptosis-related ROS may be formed in a cell in response to an apoptotic stimulus and/or produced by non-respiratory electron transport chains (i.e., other than ROS produced by oxidative phosphorylation).

The compounds of Structural Formula I have antioxidant and/or free radical scavenging properties as demonstrated hereinafter by their SOD, CAT or POD mimetic activity.

The present invention thus also provides compounds of Structural Formula I for use in medical therapy. The compounds of the present invention are of potential utility in treating and preventing free radical associated diseases and conditions which involve a component of oxidative stress including, for example, Alzheimer's disease, dementia, Parkinson's disease, Lou Gehrig's disease, motor neuron disorders, Huntington's disease, cancer, multiple sclerosis, systemic lupus erythematosus, scleroderma, eczema, dermatitis, delayed type hypersensitivity, psoriasis, gingivitis, adult respiratory distress syndrome, septic shock, multiple organ failure, asthma, allergic rhinitis, pneumonia, emphysema, chronic bronchitis, AIDS, inflammatory bowel disease, pancreatitis, transplantation rejection, atherosclerosis, hypertension, congestive heart failure, myocardial ischemic disorders, angioplasty, endocarditis, retinopathy of prematurity, cataract formation, uveitis, rheumatoid arthritis, osteoarthritis and aging.

In preferred embodiments, the compounds of the present invention and formulations thereof may be used for preventing, arresting, or treating (1) neurological damage such as Parkinson's disease or Alzheimer's disease, (2) cardiac tissue necrosis resulting from cardiac ischemia, (3) autoimmune neurodegeneration (e.g., encephalomyelitis), (4) acute lung injury such as in sepsis and endotoxemia, and (5) neuronal damage resulting from ischemia (e.g., stroke, drowning, brain surgery) or trauma (e.g., concussion or cord shock).

The compounds of the present invention and formulations thereof also have utility for the following additional indications: (1) for preventing ischemic/reoxygenation injury in a patient, (2) for preserving organs for transplant in an anoxic, hypoxic, or hyperoxic state prior to transplant, (3) for protecting normal tissues from free radical-induced damage consequent to exposure to ionizing radiation and/or chemotherapy, as with bleomycin, (4) for protecting cells and tissues from free radical-induced injury consequent to exposure to xenobiotic compounds which form free radicals, either directly or as a consequence of monooxygenation through the cytochrome P-450 system, (5) for enhancing cryopreservation of cells, tissues, organs, and organisms by increasing viability of recovered specimens and (6) for prophylactic administration to prevent carcinogenesis, cellular senescence, cataract formation, formation of malondialdehyde adducts, HIV pathology (as described below) and macromolecular crosslinking, such as collagen crosslinking.

The compounds of the present invention and formulations thereof can also be of benefit to patients who are infected with a human immunodeficiency virus (e.g., HIV-1) or who are at risk of becoming infected with a human immunodeficiency virus. The antioxidant compounds of the present invention can prevent or inhibit the induction of HIV-1replication in CD4+lymphocytes by tumor necrosis factor (TNF or other inflammatory mediators) and/or prevent damage to or death of CD4+cells as a consequence of HIV-1 infection. Without wishing to be bound by any particular theory of HIV-1 replication or HIV-1 pathogenesis, it is believed that administration of an antioxidant complex can inhibit and/or slow the development of HIV-1 related pathology and/or can reduce the rate of decline of the CD4+ lymphocyte population in HIV infected individuals. The antioxidant compounds of the present invention can also inhibit pathology resulting from excessive or inappropriate levels of TNF or other inflammatory mediators, both in AIDS and in other conditions (e.g., septic shock). Frequently, a dosage of about 50 to 5000 mg will be administered to a patient with HIV and/or with excessive or inappropriate levels of TNF, either in single or multiple doses, to reduce or retard the development of pathology and clinical symptoms. Antioxidant compounds of the present invention can be administered therapeutically to treat viral diseases other than HIV.

The compounds of the present invention and formulations thereof can also have utility in enhancing the recovery of skin of a warm-blooded animal from wounds, such as surgical incisions, burns, inflammation or minor irritation due to oxidative damage, etc.

A further aspect of the invention provides a method of prophylaxis or treatment of a human or animal subject suffering from a disease or condition, which involves a component of oxidative stress and/or a free radical-associated condition, comprising the administration to said subject of, an effective amount of a compound of Structural Formula I.

A further aspect of the present invention provides the use of a compound of Structural Formula I in the preparation of a medicament for the prophylaxis or treatment of a disease or condition which involves a component of oxidative stress and/or a free radical-associated disease or condition.

A further aspect of the present invention provides the use of a compound of Structural Formula I in the preparation of a medicament for the prophylaxis or treatment of the specific disorders and conditions referred to above.

The compounds of the present invention and formulations thereof can be administered for prophylactic and/or therapeutic treatments. In therapeutic application, formulations are administered to a patient already affected by the particular free radical associated disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration, but generally range from about 1 $\mu$g to about 10 g of antioxidant compounds of the present invention per dose, with dosages of from 0.1 mg to 2000 mg per patient being more commonly used.

In prophylactic applications, formulations containing the antioxidant compound of the present invention or cocktails thereof are administered to a patient not already in a disease state to enhance the patient's resistance or to retard the progression of disease. Such an amount is defined to be a "prophylactically effective dose." In this use, the precise amounts again depend upon the patient's state of health and general level of immunity, but generally range from 1 $\mu$g to 10 g per dose, especially 0.01 mg to 1000 mg per patient.

As indicated above, a typical formulation of a compound of the present invention will contain between about 0.1 and 250 mg of the complex in a unit dosage form. Single or multiple administrations of the formulations can be carried out with dose levels and dosing pattern being selected by the treating physician.

In general, for treatment of free radical-associated diseases, a suitable effective dose of the antioxidant compound of the present invention will be in the range of 0.01 microgram ($\mu$g) to 1000 milligram (mg) per kilogram (kg) of body weight of recipient per day, preferably in the range of 0.1 $\mu$g to 100 mg per kg of body weight per day, more preferably in the range of 1 $\mu$g to 10 mg per kg of body weight per day. For example, 0.2 mg/kg for a 70 kg human adult would result in a daily dose of 14 mg. The desired dosage is preferably presented in one, two, three, four or more subdoses administered at appropriate intervals throughout the day. These subdoses can be administered in unit dosage forms as referred to above.

Kits can also be supplied which contain the compounds of the present invention for use in the protection against or therapy for a free radical-associated disease. Thus, the subject formulation of the present invention may be provided, usually in a lyophilized form or aqueous solution, in a container, either alone or in conjunction with additional antioxidant compounds of the present invention of the desired type. The antioxidant compounds are included in the kits with buffers, such as Tris, phosphate, carbonate, etc., stabilizers, biocides, inert proteins, e.g. serum albumin, or the like, and a set of instructions for use. Generally, these materials will be present in less than about 5% wt. based on the amount of antioxidant compounds of the present invention and usually present in total amount of at least about 0.001% based again on the concentration. Frequently, it will be desirable to include an inert extender or excipient to dilute the active ingredients, where the excipient may be present in from about 1 to 99.999% wt. of the total formulation.

The compounds of the present invention may be employed alone or in combination with other therapeutic agents for the treatment of the above-mentioned conditions, and in particular in combination with other antioxidant agents that have SOD activity, catalase activity, peroxidase activity, or are free radical scavengers or inhibitors of free radical formation. Combination therapies according to the present invention thus comprise the administration of at least one compound of Structural Formula I or a pharmaceutically acceptable derivative(s) thereof and at least one other pharmaceutically active agent. The compound(s) of Structural Formula I or a pharmaceutically acceptable derivative(s) thereof and the other pharmaceutically active agent(s) may be administered together or separately and, when administered separately, the respective administrations may occur simultaneously or sequentially in any order. The amounts of the compound(s) of Structural Formula I or pharmaceutically acceptable derivative(s) thereof and the other pharmaceutically active agent(s) as well as the relative timings of administration will be selected in order to achieve the desired combined therapeutic effect.

Certain embodiments of the present invention will now be illustrated by way of example only. The physical data given for the compounds exemplified is consistent with the assigned structure of those compounds.

EXAMPLES

In the following synthesis examples, all chemicals were of reagent grade and purchased from Aldrich (Milwaukee, Wis.). Column chromatography was carried out on silica gel 60 (70–230 mesh), or basic alumina 90 (70–230 mesh) obtained from Merck (Whitehouse Station, N.J.). The ion-exchange resin AG1-X8 (100–200 mesh) acetate form was purchased from Bio Rad Laboratories (Hercules, Calif.). Elemental analyses were carried out by the "Service de Microanalyse du Laboratoire de Chimie de Coordination du CNRS". The nuclear magnetic resonance spectra were recorded on a Bruker AM 250 A or a Bruker AC 200 spectrometer. UV-visible spectra were obtained on Hewlett packard 8452A diode array spectrophotometer. The mass spectra were recorded on a Nermag R10-10H for the FAB+ spectra and on a API 365 PE SCIEX for the electrospray spectra. Infrared spectra were recorded on a Perkin-Elmer 1725X FT-IR Spectrometer. DMF refers to dimethylformamide.

Example 1

(Scheme A)

Synthesis of meso-tetrakis[4-(N-(2-(N,N-diethylammonio)ethyl)aminosulfonyl)phenyl]porphyrinato diaqua-manganese (III) pentachloride, Structural Formula II This complex, Structural Formula II, was prepared from meso-tetraphenylporphyrin, Structural Formula i, in three steps as described hereafter.

1.1. Synthesis of meso-tetraphenylporphyrin, Structural Formula i

Structural Formula i was prepared from pyrrole and benzaldehyde according to the method of J. S. Lindsey and R. W. Wagner, *J. Org. Chem.*, 54, 1989, 828.

1.2. Synthesis of meso-tetrakis[4-(N-(2-(N,N-diethylamino)ethyl)aminosulfonyl)phenyl]porphyrin, Structural Formula ii Meso-tetraphenyl porphyrin (Structural Formula i; 1.00 g, 1.62 mmol) was dissolved in 100 mL $CH_2Cl_2$. 12.97 mL of chlorosulfonic acid were added dropwise with stirring at 0° C. for 0.5 h. When the formation of hydrogen chloride stopped, the reaction mixture was cooled to room temperature, stirred for 0.5 h and then heated to 55° C. for 1 h. After the reaction mixture cooled to room temperature, the reaction flask was put in an ice-water bath and 200 mL of crushed ice was quickly added. A solution of 2 M KOH in water was then added to bring the mixture to pH 14. To this heterophasic mixture, 9.14 mL (65.05 mmol) of N,N-diethylenediamine was added at room temperature and heated to 55° C. for 2 h. When the solution cooled to room temperature, the organic layer was separated with $CH_2Cl_2$, dried over anhydrous magnesium sulfate and the solvents removed under vacuum. The crude product was dissolved in the minimum quantity of $CH_2Cl_2$ and precipitated by adding n-hexane. The precipitate was filtered and washed with a large quantity of n-hexane to give the purple powder, Structural Formula ii: 1.58 g (70% yield). UV-visible $(CH_2Cl_2)$ $\lambda(\epsilon\ mol^{-1}\ L\ cm^{-1})$: 420 (486×10$^3$), 514 (27.8×10$^3$), 548 (11.9×10$^3$), 590 (9.6×10$^3$), 646 (5.5×10$^3$). $^1$H NMR (CDCl$_3$ at 298K) δ: −2.85 (s, 2H, NH), 1.04 (t, J=6.9 Hz, 24H, $\underline{CH_3}CH_2N$), 2.53 (q, J=6.9 Hz, 16H, $CH_3\underline{CH_2}N$), 2.68 (t, J=5.5 Hz, 8H, $CH_2\underline{CH_2}N$), 3.26 (t, J=5.5 Hz, 8H, $\underline{CH_2}CH_2N$), 8.32 (AB System, J=7.8 Hz, 16H, Har), 8.77 (s, 8H, Hβ). Anal.: Calc for $C_{68}H_{86}N_{12}O_8S_4 \cdot H_2O$: C, 60.69; H, 6.59; N, 12.49. Found: C, 60.60; H, 6.46; N; 12.43. MS (FAB+/MNBA), m/z 1327 (MH+).

1.3. Synthesis of meso-tetrakis[4-(N-(2-(N,N-diethylamino)ethyl)aminosulfonyl)phenyl]porphyrinato-hydroxo-manganese (III), Structural Formula iii To a solution of 0.70 g (0.52 mmol) of Structural Formula ii in 50 mL of DMF 0.69 mL (5.27 mmol) of 2,4,6-collidine was added and a large excess of $Mn(OAc)_2 \cdot 4H_2O$ (10.5 mmol). The mixture was heated at 150° C. for 2 h. The reaction mixture was then cooled to room temperature and 50 mL of DMF and 200 mL of 1 M KOH were added. The metallated porphyrin was extracted with 200 mL of $CH_2Cl_2$ and the organic layer was dried over anhydrous magnesium sulfate. Solvents were removed under vacuum and the crude product was dissolved in the minimum quantity of $CH_2Cl_2$. A large quantity of n-hexane was then added to the solution until a precipitate formed. The precipitate was filtered and washed several times with n-hexane leaving a dark green powder, Structural Formula iii. 0.47 g (60% yield). UV-visible $(CH_2Cl_2)$ $\lambda(\epsilon\ mol^{-1}\ L\ cm^{-1})$: 348 (40.4×10$^3$), 374 (51.5×10$^3$), 398 (42.8×10$^3$), 478 (105.2×10$^3$), 580 (10.2×10$^3$), 616 (9.8×10$^3$). Anal.: Calc for $C_6H_{85}N_{12}O_9S_4Mn \cdot 5H_2O$: C, 54.90; H, 6.44; N, 11.30. Found: C, 54.57; H, 5.95; N, 11.03. MS (FAB+/MNBA), m/z 1379 (M+).

1.4. Synthesis of meso-tetrakis[4-(N-(2-(N,N-diethylammonio)ethyl)aminosulfonyl)phenyl]porphyrinato diaqua-manganese (III) pentachloride 4, Structural Formula II To a solution of 0.44 g (0.29 mmol) of Structural Formula iii in 10 mL of absolute ethanol, 1 mL of a solution of 6 M HCl in isopropanol at room temperature was added. After 10 min, solvents were removed and the dried residue was dissolved in the minimum quantity of methanol. The protonated metalloporphyrin was precipitated by adding a large quantity of diethylether and then filtered leaving a dark green powder which was dried under vacuum overnight: 0.46 g (92% yield). UV-visible (MeOH) $\lambda(\epsilon\ mol^{-1}\ L\ cm^{-1})$: 378(47.7×10$^3$), 398 (49.9×10$^3$), 466 (98.5×10$^3$), 562 (11.3×10$^3$), 594 (7.3×10$^3$). Anal.: Calc for $C_{68}H_{88}N_{12}O_8S_4Cl_5Mn \cdot 8H_2O$: C, 47.87; H, 6.14; N, 9.85. Found: C, 47.87; H, 5.56; N, 9.81. MS (ES), m/z 1379.5 $(C_{68}H_{84}N_{12}O_8S_4Mn, z=1)$, 690.4 $(C_{68}H_{85}N_2O_8S_4Mn, z=2)$.

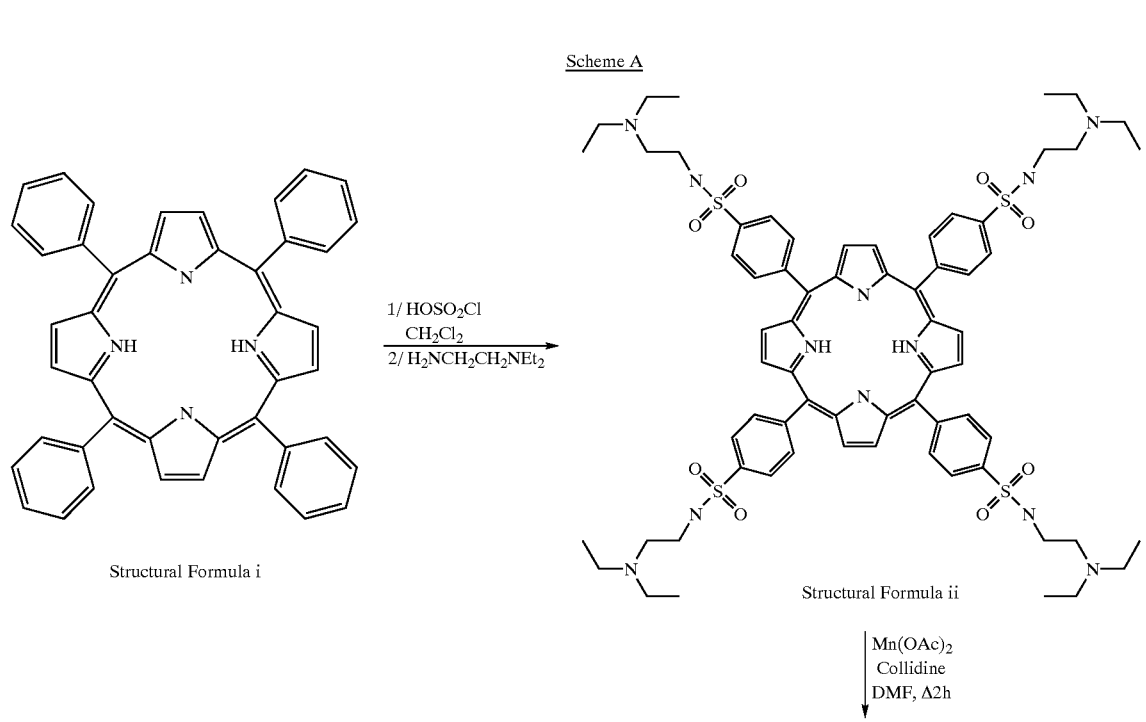

Scheme A

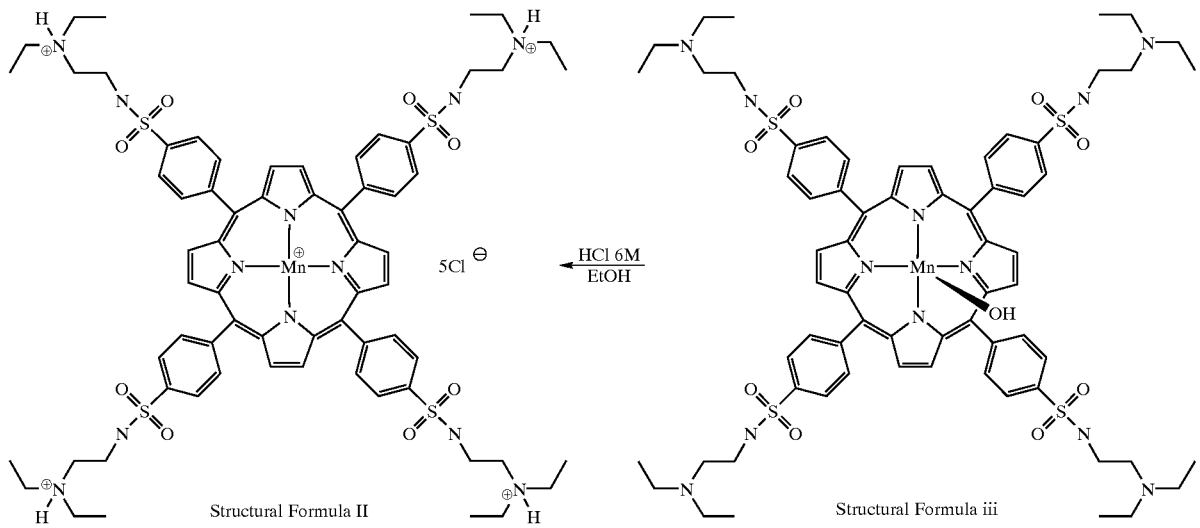

Example 2
(Scheme B)

Synthesis of meso-tetrakis[4-(N-(2-(N,N-diethylammonio)ethyl)aminosulfonyl)phenyl]porphyrinato diaqua-iron (III) pentachloride, Structural Formula III This complex of Structural Formula III was prepared from meso-tetraporphyrin, Structural Formula i, in three steps as described hereafter 2.1. Synthesis of μ-oxo-[meso-tetrakis[4-(N-(2-(N,N-diethylamino)ethyl)aminosulfonyl)phenyl]porphyrinato iron (III), Structural Formula iv To a solution of 0.22 g (0.16 mmol) of Structural Formula ii (prepared from Structural Formula i, as described above, in Example 1) in 20 mL of DMF, 0.21 mL (1.65 mmol) of 2,4,6-collidine and a large excess of $FeCl_2.4H_2O$ (3.29 mmol) was added. The mixture was heated at 150° C. for 4 h. The reaction mixture was then cooled to room temperature and 50 mL of DMF and 200 mL of 1 M KOH were added. The metallated porphyrin was extracted with 200 mL of $CH_2Cl_2$ and the organic layer was dried over anhydrous magnesium sulfate. Solvents were removed under vacuum and the crude product was dissolved in the minimum quantity of $CH_2Cl_2$. A large quantity of n-hexane was then added to the solution until a precipitate formed. The precipitate was filtered off, and washed several times with n-hexane leaving a dark brown powder, Structural Formula iv: 0.17 g (73% yield). UV-visible ($CH_2Cl_2$) $\lambda(\epsilon$ mol$^{-1}$ L cm$^{-1}$): 318 (30.1× $10^3$), 408 (93.7×$10^3$), 566 (8.9×$10^3$), 608 (4.1×$10^3$). Anal.: Calc for $C_{136}H_{168}N_{24}O_{17}S_8Fe_2.6H_2O$: C, 56.58; H, 6.28; N, 11.64. Found: C, 56.53 ; H, 5.83; N, 11.39. MS (ES), m/z 2780.3 (M+H, z=1), 1390.2 (M+2H, z=2), 927.3 (M+3H, z=3). IR (KBr) 875.0 cm$^{-1}$ (Fe—O—Fe).

2.2. Synthesis of meso-tetrakis[4-(N-(2-(N,N-diethylammonio)ethyl)aminosulfonyl)phenyl]porphyrinato diaqua-iron (III) pentachloride, Structural Formula III To a solution of 0.50 g (0.17 mmol) of Structural Formula iv in 10 mL of ethanol 95%, 0.31 mL of an aqueous solution of 1 M HCl was added at room temperature. After 10 min, solvents were removed and the dried residue was dissolved in the minimum quantity of methanol. The protonated metalloporphyrin was precipitated by adding a large quantity of diethylether and then filtered leaving a dark brown powder which was dried under vacuum overnight: 0.49 g (86% yield). UV-visible (MeOH) $\lambda(\epsilon$ mol$^{-1}$ L cm$^{-1}$): 340 (34.4× $10^3$), 414 (119.4×$10^3$). Anal.: Calc for $C_{68}H_{88}N_{12}O_8S_4Cl_5Fe.6H_2O$: C, 48.88; H, 6.03; N, 10.06. Found: C, 48.83; H, 5.28; N, 10.00. MS (ES), m/z 1416.5 ($C_{68}H_{85}N_{12}O_8S_4FeCl$, z=1), 708.9 ($C_{68}H_{86}N_{12}O_8S_4FeCl$, z=2).

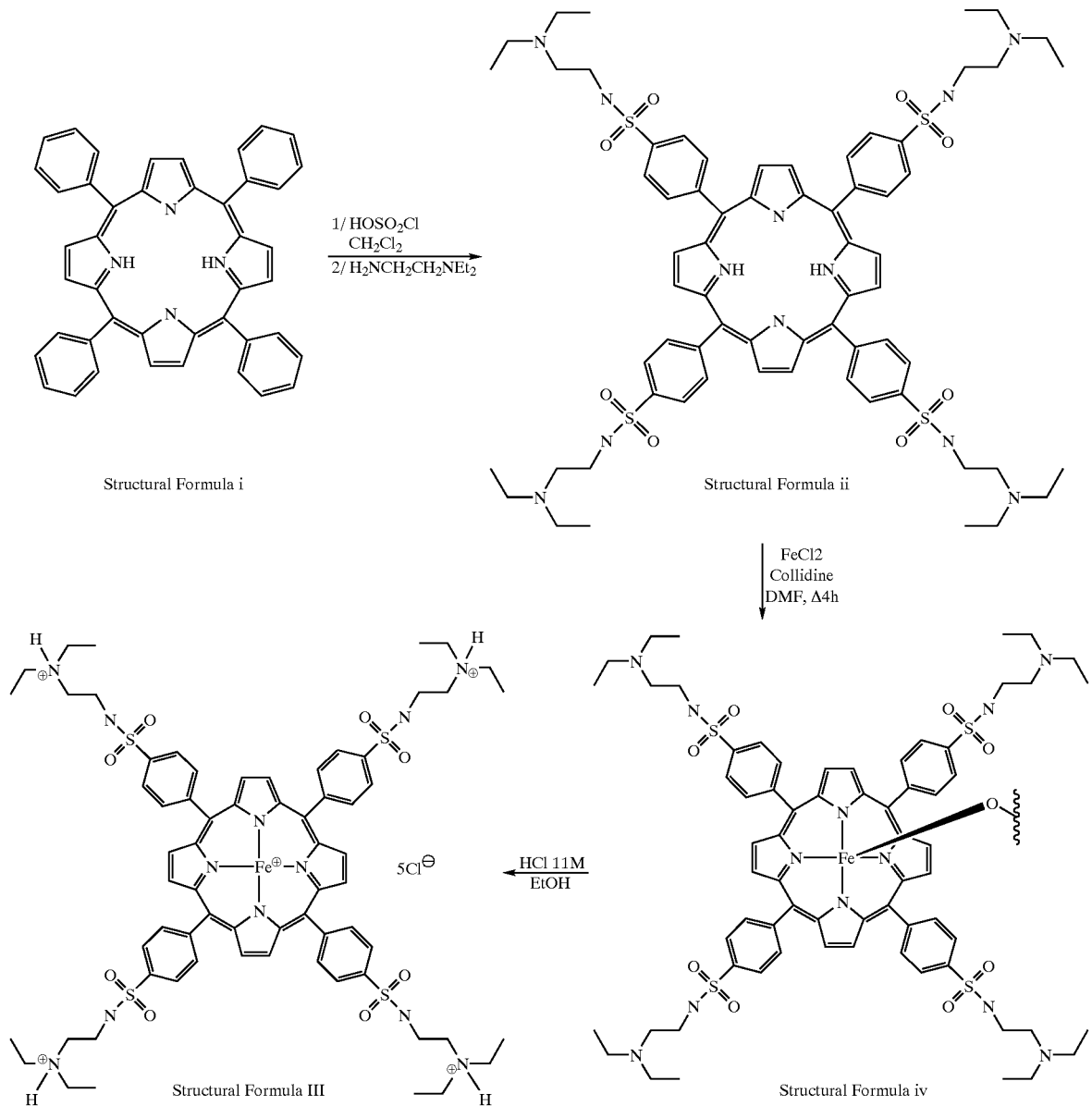

Scheme B

Example 3
(Scheme C)

Synthesis of meso-tetrakis[3-(N-(2-(N,N-diethylammonio)ethyl)aminosulfonyl)-2,4,6-trimethylphenyl]porphyrinato diaqua-manganese (III) pentachloride, Structural Formula IV This complex was prepared from compound Structural Formula v, in three steps as described hereafter.

3.1. Synthesis of meso-tetrakis(2,4,6-trimethylphenyl) porphyrin, Structural Formula v Structural Formula v was prepared from pyrrole and mesitaldehyde by the method of J. S. Lindsey and R. W. Wagner, *J. Org. Chem.*, 54, 1989, 828.

3.2. Synthesis of meso-tetrakis[3-(N-(2-(N,N-diethylamino)ethyl)aminosulfonyl)-2,4,6-trimethylphenyl]porphyrin, Structural Formula vi Structural Formula v (0.61 g, 0.78 mmol) was dissolved in 50 mL $CH_2Cl_2$. 7.95 mL of chlorosulfonic acid was added dropwise with stirring at 0° C. for 0.5 h. When the formation of hydrogen chloride stopped, the reaction mixture was cooled to room temperature, stirred for 0.5 h and then heated to 55° C. for 1 hour. After the reaction mixture cooled to room temperature, the reaction flask was put in an ice-water bath and 200 mL of crushed ice were quickly added to the mixture. When the addition was finished, a solution of 2 M KOH in water was added to bring the mixture to pH 14. To this heterophasic mixture, 4.39 mL (31.0 mmol) of N,N-diethylenediamine was added at room temperature and then heated to 55° C. for 2 h. The solution was cooled to room temperature. The organic layer was separated with $CH_2Cl_2$, dried over anhydrous magnesium sulfate and the solvents were removed under vacuum. The crude product was dissolved in the minimum quantity of $CH_2Cl_2$ and precipitated by adding n-hexane. The precipitate was filtered and then washed with a large quantity of n-hexane to give the purple powder, Structural Formula vi: 0.96 g (82% yield). UV-visible (CH$_2$Cl$_2$) λ(ε mol$^{-1}$ L cm$^{-1}$): 420 (429×10$^3$), 516 (20.5×10$^3$), 548 (6.2×10$^3$), 592 (6.1×10$^3$). $^1$H NMR (CDCl$_3$ at 298K) δ: −2.45 (s, 2H, NH), 0.92 (m, 24H, CH$_3$CH$_2$N), 1.81 (m, 12H, CH$_3$(6)), 2.19 (m, 12H, CH$_3$(2)), 2.55 (m, 16H, CH$_3$CH$_2$N), 2.73 (s, 8H, CH$_2$CH$_2$N), 3.00 (s, 12H, CH$_3$(4)), 3.19 (s, 8H, CH$_2$CH$_2$N), 7.44 (s, 4H, Har) 8.52 (s, 8H, Hβ). Anal.: Calc for C$_{80}$H$_{110}$N$_{12}$O$_8$S$_4$.H$_2$O: C, 63.46; H, 7.46; N, 11.10. Found: C, 62.78; H, 7.44; N, 10.93. MS (FAB+/MNBA), m/z 1495 (MH+).

3.3. Synthesis of meso-tetrakis[3-(N-(2-(N,N-diethylamino)ethyl)aminosulfonyl)-2,4,6-trimethylphenyl]porphyrinato hydroxo-manganese (III), Structural Formula vii To a solution of 0.32 g (0.21 mmol) of Structural Formula vi in 20 mL of DMF, 0.28 mL (2.13 mmol) of 2,4,6-collidine and a large excess of Mn(OAc)$_2$.4H$_2$O (4.26 mmol) was added. The mixture was heated at 150° C. for 2 h. The reaction mixture was cooled to room temperature and then 50 mL of DMF and 200 mL of 1 M KOH were added. Metallated porphyrin was extracted with 200 mL of CH$_2$Cl$_2$ and the organic layer was dried over anhydrous magnesium sulfate. The solvents were removed under vacuum and the crude product was dissolved in the minimum quantity of CH$_2$Cl$_2$. A large quantity of n-hexane was then added to the solution until a precipitate formed. The precipitate was filtered and washed several times with n-hexane leaving a dark green powder, Structural Formula vii: 0.26 g (77% yield). UV-visible (CH$_2$Cl$_2$) λ(ε mol$^{-1}$ L cm$^{-1}$): 372 (54.9× 10$^3$), 400 (47.9×10$^3$), 478 (118.8×10$^3$), 582 (12.4×10$^3$), 616 (10.6×10$^3$). Anal.: Calc for C$_{80}$H$_{109}$N$_{12}$O$_9$S$_4$Mn.2H$_2$O: C, 59.98; H, 7.11; N, 10.49. Found: C, 59.51; H, 6.55; N, 10.23. MS (FAB+/MNBA), m/z 1549 (M+).

3.4. Synthesis of meso-tetrakis[3-(N-(2-(N,N-diethylammonio)ethyl)aminosulfonyl)-2,4,6-trimethylphenyl]porphyrinato diaqua-manganese (III) pentachloride, Structural Formula IV To a solution of 0.24 g (0.15 mmol) of Structural Formula vii in 10 mL of absolute ethanol, 0.25 mL of a solution of 6 M HCL in isopropanol was added at room temperature. After 10 min, the solvents were removed and the dried residue was dissolved in the minimum quantity of methanol. The protonated metalloporphyrin was precipitated by adding a large quantity of diethylether and filtered off leaving a dark green powder which was dried under vacuum overnight: 0.23 g (80% yield). UV-visible (MeOH) λ(ε mol$^{-1}$ L cm$^{-1}$): 376 (38.0×10$^3$), 398 (40.2×10$^3$), 468 (101.0×10$^3$), 568 (9.3× 10$^3$), 596 (5.7×10$^3$). Anal.: Calc for C$_{80}$H$_{112}$N$_{12}$O$_8$S$_4$Cl$_5$Mn.8H$_2$O: C, 51.26; H, 6.88; N, 8.97. Found: C, 51.01; H, 6.31; N, 8.95. MS (ES), m/z 1584.0 (C$_{80}$H$_{109}$N$_{12}$O$_8$S$_4$ClMn, z=1), 1548.8 (C$_{80}$H$_{108}$N$_{12}$O$_8$S$_4$Mn, z=1).

Scheme C

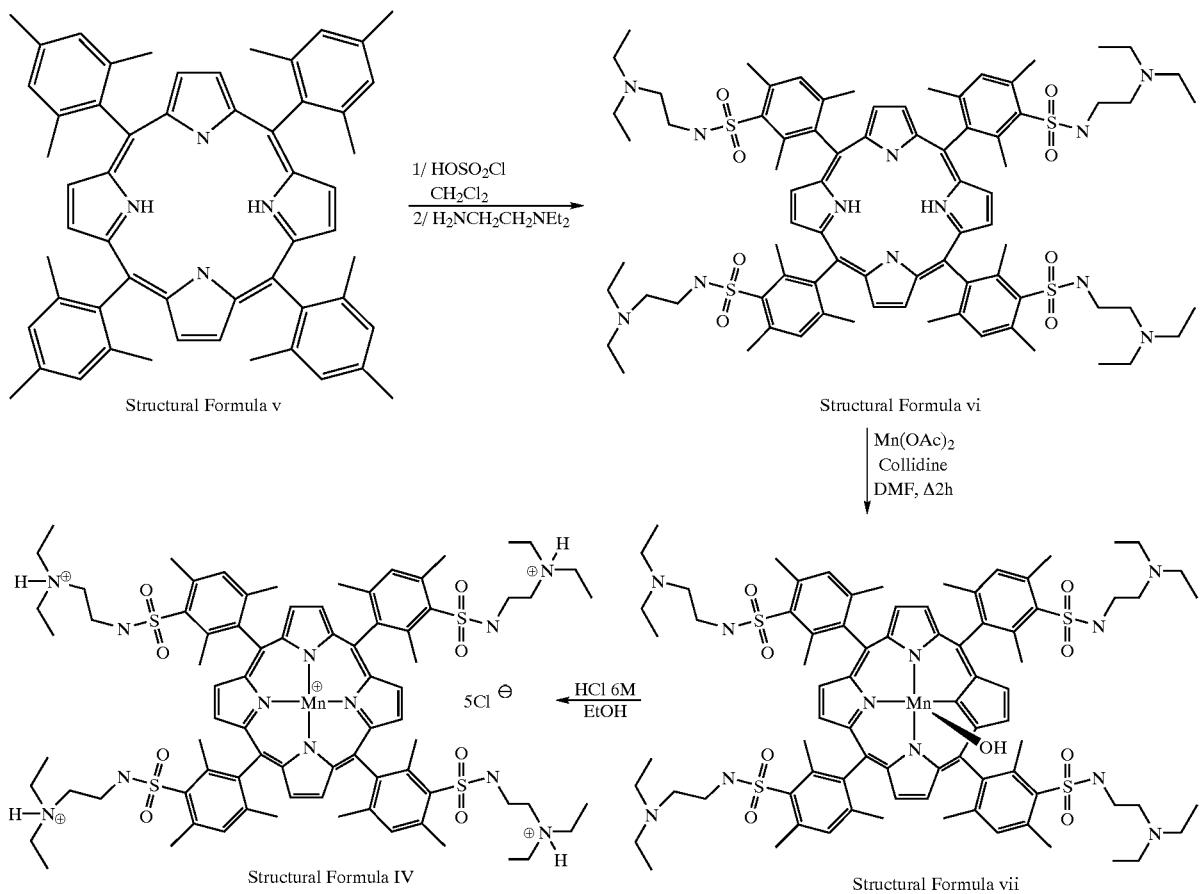

Structural Formula v

Structural Formula vi

Structural Formula IV

Structural Formula vii

Example 4

(Scheme D)

Synthesis of meso-tetrakis[3-(N-(2-(N,N-diethylammonio)ethyl)aminosulfonyl)-2,4,6- trimethylphenyl]porphyrinato diaqua-iron (III) pentachloride, Structural Formula V The complex of Structural Formula V was prepared from meso-tetraporphyrin, Structural Formula v, in three steps as described hereafter.

4.1. Synthesis of meso-tetrakis[3-(N-(2-(N,N-diethylamino)ethyl)aminosulfonyl)-2,4,6-trimethylphenyl]porphyrinato hydroxo-iron(III), Structural Formula viii To a solution of 0.33 g (0.22 mmol) of Structural Formula vi (prepared from Structural Formula v, as described above, Example 3) in 20 mL of DMF, 0.28 mL (2.13 mmol) of 2,4,6-collidine and a large excess of $FeCl_2.4H_2O$ (4.35 mmol) were added. The mixture was heated at 150° C. for 4 h. The reaction mixture was then cooled to room temperature. 50 mL of DMF and 200 mL of 1M KOH were then added. Metallated porphyrin was extracted with 200 mL of $CH_2Cl_2$ and the organic layer was dried over anhydrous magnesium sulfate. Solvents were removed under vacuum and the crude product was dissolved in the minimum quantrimethylphenyl]porphyrinato diaqua-iron (III) pentachloride, Structural Formula V To a solution of 0.23 g (0.14 mmol) of Structural Formula viii in 10 mL of absolute ethanol, 0.25 mL of a solution of 6M HCl in isopropanol was added at room temperature. After 10 min, solvents were removed and the dried residue was dissolved in the minimum quantity of methanol. The protonated metalloporphyrin was precipitated by adding a large quantity of diethylether and then filtered off leaving a dark brown powder which was dried under vacuum overnight: 0.23 g (90% yield). UV-visible (MeOH) $\lambda(\epsilon\ mol^{-1}\ L\ cm^{-1})$: 336 (34.6×10$^3$), 416 (121.4×10$^3$). Anal.: Calc for $C_{80}H_{112}N_{12}O_8S_4Cl_5Fe.6H_2O$: C, 52.24; H, 6.80; N, 9.14. Found: C, 52.60; H, 5.83; N, 8.87. MS (ES), m/z 1548.7 ($C_{80}H_{108}N_{12}O_8S_4Fe$, z=1), 801.9 ($C_{80}H_{110}N_{12}O_8S_4ClFe+H_2O$, z=2), 523.0 ($C_{80}H_{110}N_{12}O_8S_4Fe+H_2O$, z=3).

Scheme D

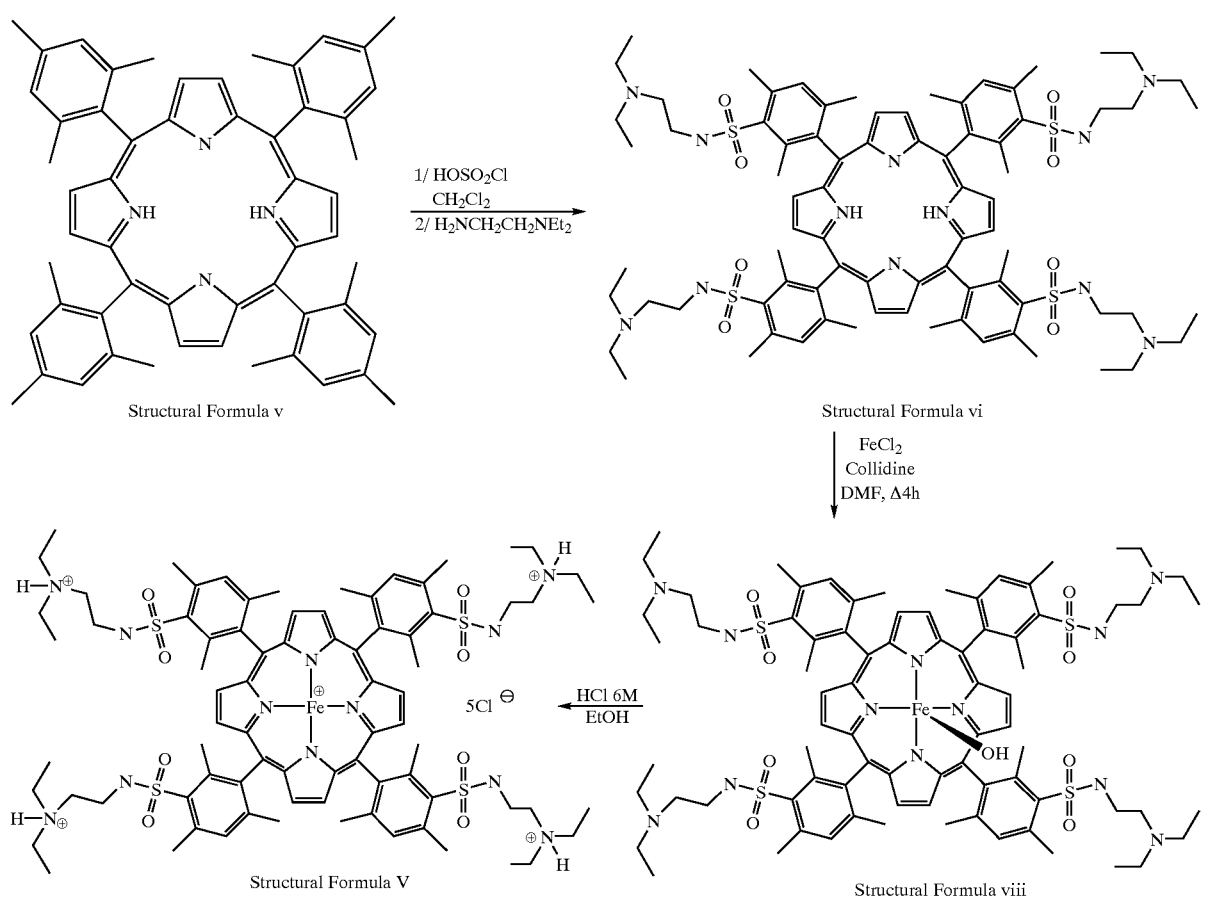

tity of $CH_2Cl_2$. A large quantity of n-hexane was then added to the solution to obtain a precipitate. The precipitate was filtered and washed several times with n-hexane leaving a dark brown powder, Structural Formula viii: 0.24 g (70% yield). UV-visible ($CH_2Cl_2$) $\lambda(\epsilon\ mol^{-1}\ L\ cm^{-1})$: 348 (49.3×10$^3$), 370 (55.0×10$^3$), 420 (119.8×10$^3$), 510 (14.7×10$^3$). Anal.: Calc for $C_{80}H_{109}N_{12}O_9S_4Fe.2H_2O$: C, 59.95; H, 7.11; N, 10.49. Found: C, 58.95; H, 6.74; N, 10.13. MS (FAB+/MNBA), m/z 1550 (M+).

4.2. Synthesis of meso-tetrakis[3-(N-(2-(N,N-diethylammonio)ethyl)aminosulfonyl)-2,4,6-

Example 5

(Scheme E)

Synthesis of meso-tetrakis[4-(N-(2-(N,N,N-diethylmethylammonio)ethyl)aminosulfonyl)phenyl]porphyrinato diaqua-manganese (III) pentaacetate, Structural Formula VI This complex of Structural Formula VI, was prepared from compound Structural Formula iii in two steps as described hereafter.

5.1. Synthesis of meso-tetrakis[4-(N-(2-(N,N,N-diethylmethylammonio)ethyl)aminosulfonyl)phenyl] porphyrinato diaqua-manganese (III) pentaiodide, Structural Formula ix 10.6 mL of methyl iodide was added to a solution of Structural Formula iii (0.50 g, 0.34 mmol) in 50 mL DMF at room temperature. The mixture was stirred 3 h. After concentration under vacuum, the crude product was dissolved in a minimum quantity of methanol and precipitated by adding diethylether. The powder was filtered and washed several times with diethylether leaving a dark green powder, Structural Formula ix: 0.63 g (84% yield). UV-visible ($H_2O$) $\lambda(\epsilon$ $mol^{-1}$ $L$ $cm^{-1}$): 378 (55.5×10$^3$), 400 (56.9×10$^3$), 418 (37.6×10$^3$), 466 (99.7×10$^3$), 560 (13.7×10$^3$), 588 (9.2×10$^3$). Anal.: Calc for $C_{72}H_{96}N_{12}O_8S_4I_5Mn\cdot6H_2O$: C, 39.61; H, 4.99; N, 7.70. Found: C, 39.13; H, 4.87; N, 8.01. MS (ES), m/z 1805.5 ($C_{71}H_{93}N_{12}O_8S_4I_3Mn$, z=1), 839.3 ($C_{71}H_{93}N_{12}O_8S_4I_2Mn$, x=2).

5.2. Synthesis of meso-tetrakis[4-(N-(2-(N,N,N-diethylmethylammonio)ethyl)aminosulfonyl)phenyl] porphyrinato diaqua-manganese (III) pentaacetate, Structural Formula VI To a solution of 0.52 g (0.24 mmol) of Structural Formula ix in 25 mL of methanol, 16.5 g of AG1-X8 acetate form resin was added. The mixture was carefully stirred 3 h at room temperature. The resin was filtered and washed several times with a large quantity of methanol. The filtrate was then concentrated under vacuum. The residue was dissolved in a minimum quantity of methanol and precipitated by adding a large excess of diethylether. The precipitate was filtered, washed with diethylether and dried under vacuum overnight leaving a dark green powder, Structural Formula VI: 0.37 g (76% yield). UV-visible ($H_2O$) $\lambda(\epsilon$ $mol^{-1}$ $L$ $cm^{-1}$): 378 (57.9×10$^3$), 400 (59.0×10$^3$), 466 (104.6×10$^3$), 562 (13.7×10$^3$), 592 (8.9×10$^3$). Anal.: Calc for $C_{82}H_{111}N_{12}O_{18}S_4Mn\cdot6H_2O$: C, 53.41; H, 6.72; N, 9.11. Found: C, 53.23; H, 7.00; N, 9.60. MS (ES), m/z 1453.5 ($C_{71}H_{90}N_{12}O_{10}S_4Mn$, z=1).

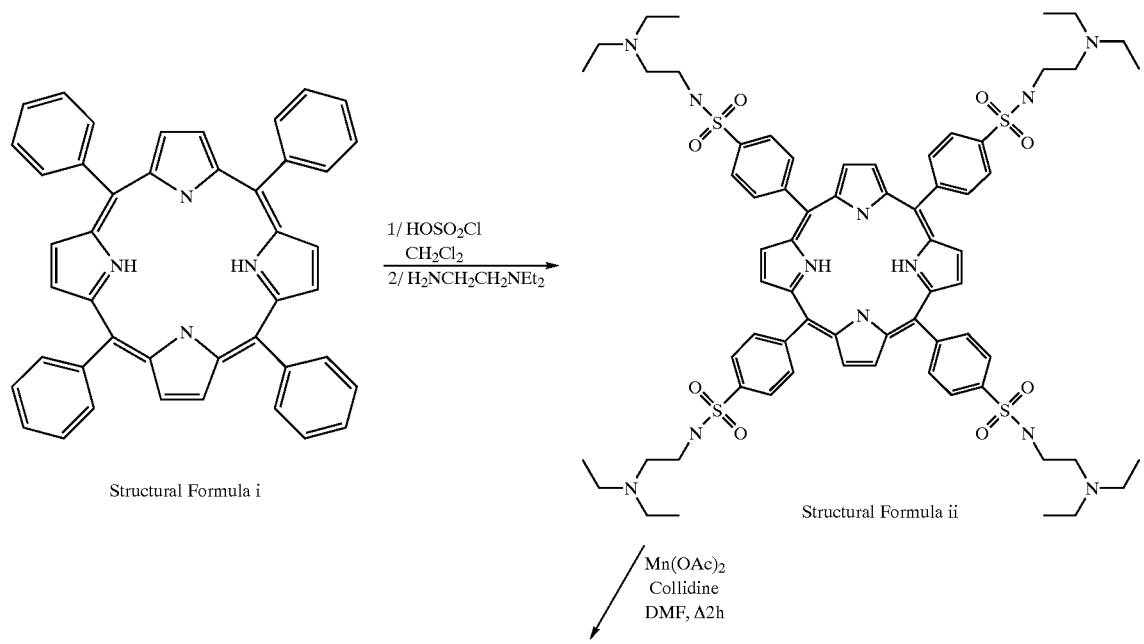

Scheme E

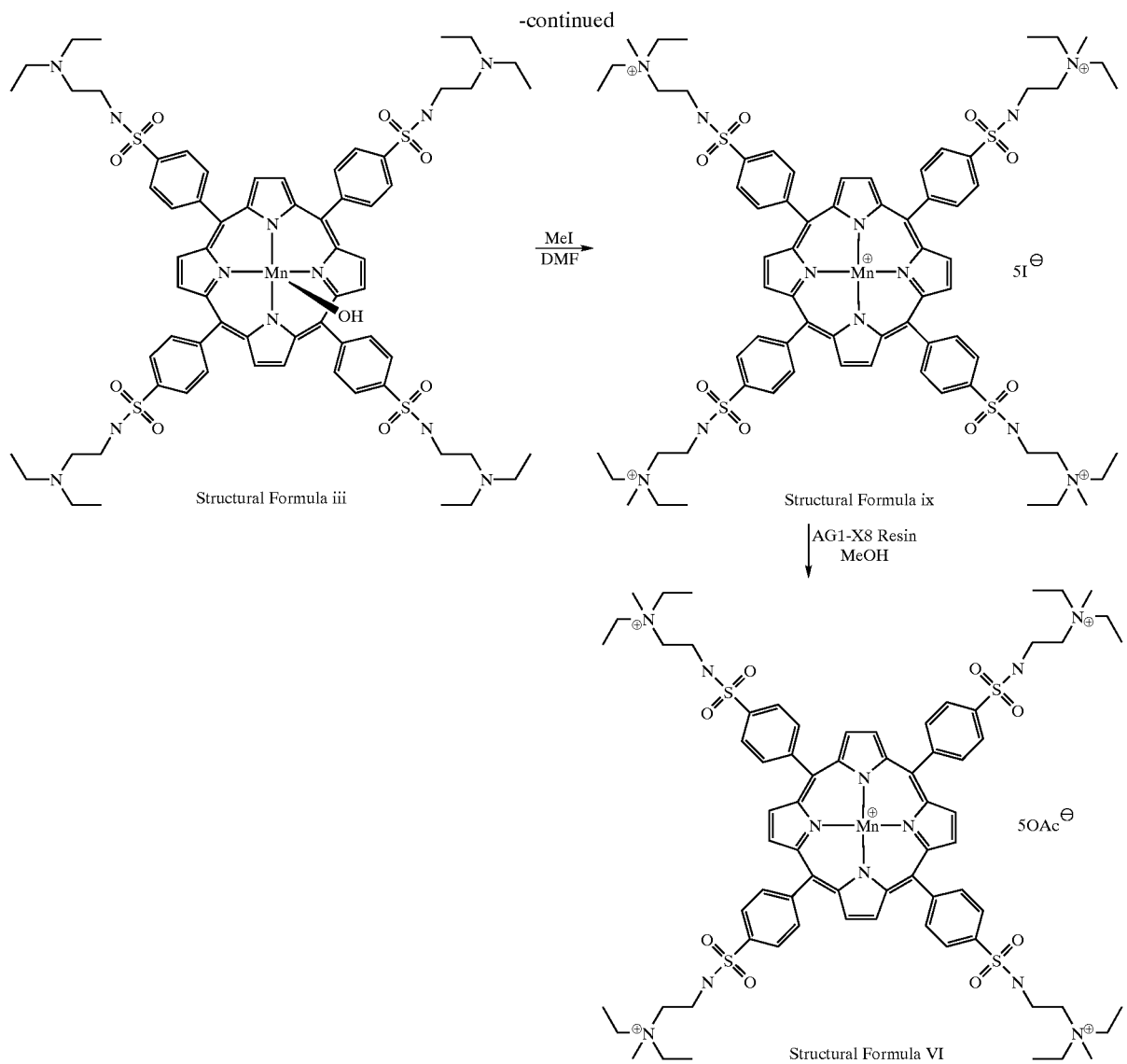

Example 6
(Scheme F)
Synthesis of meso-tetrakis[3-(N-(2-(N,N,N-diethylmethylammonio)ethyl)aminosulfonyl)-2,4,6-trimethylphenyl]porphyrinato diaqua-manganese (III) pentaacetate, Structural Formula VII This complex of Structural Formula VII was prepared from Structural Formula vii, (see Example 3) in two steps as described hereafter.

6.1. Synthesis of meso-tetrakis[3-(N-(2-(N,N,N-diethylmethylammonio)ethyl)aminosulfonyl)-2,4,6-trimethylphenyl]porphyrinato diaqua-manganese (III) pentaiodide, Structural Formula x 8.0 mL of methyl iodide was added to a solution of Structural Formula vii (0.41 g, 0.26 mmol) in 40 mL DMF at room temperature. The mixture was stirred for 3 h. After concentration under vacuum, the crude product was dissolved in the minimum quantity of methanol and precipitated by adding diethylether. The powder was filtered off and washed several times with diethylether leaving a dark green powder, Structural Formula x: 0.53 g (83% yield). UV-visible ($H_2O$) $\lambda(\epsilon$ mol$^{-1}$ L cm$^{-1}$): 378 (59.6×10$^3$), 400 (62.1×10$^3$), 466 (135.0×10$^3$), 568 (16.2×10$^3$), 598 (10.3×10$^3$). Anal.: Calc for $C_{84}H_{120}N_{12}O_8S_4I_5Mn.12H_2O$: C, 41.02; H, 5.90; N, 6.83. Found: C, 40.70; H, 5.23; N, 7.28. MS (ES), m/z 1973.4 ($C_{83}H_{117}N_{12}O_8S_4I_3Mn$, z=1), 1832.6 ($C_{82}H_{114}N_{12}O_8S_4I_2Mn$, z=1), 1689.7 ($C_{81}H_{111}N_{12}O_8S_4I_3Mn$, z=1).

6.2. Synthesis of meso-tetrakis[3-(N-(2-(N,N,N-diethylmethylammonio)ethyl)aminosulfonyl)-2,4,6-trimethylphenyl]porphyrinato diaqua-manganese (III) pentaacetate, Structural Formula VII To a solution of 0.40 g (0.16 mmol) of Structural Formula x in 25 mL of methanol, 11.8 g of AG1-X8 acetate form resin was added. The mixture was stirred 3 h at room temperature. The resin was filtered off and washed several times with a large quantity of methanol. The filtrate was then concentrated under vacuum. The residue was dissolved in a minimum quantity of methanol and precipitated by adding a large excess of diethylether. The precipitate was filtered, washed with diethylether and dried under vacuum overnight leaving a dark green powder: 0.28 g (84% yield). UV-visible ($H_2O$) $\lambda(\epsilon$ mol$^{-1}$ L cm$^{-1}$): 378 (51.4×10$^3$), 398 (53.8×10$^3$), 466 (118.6×10$^3$), 566 (13.4×10$^3$), 596 (8.3×10$^3$). Anal.: Calc for $C_{94}H_{135}N_{12}O_{18}S_4Mn \cdot 7H_2O$: C, 55.61; H, 7.40; N, 8.28. Found: C, 55.31; H, 7.42; N, 8.66. MS (ES), m/z 1622.8 ($C_{83}H_{114}N_{12}O_{10}S_4Mn$, z=1).

Scheme F

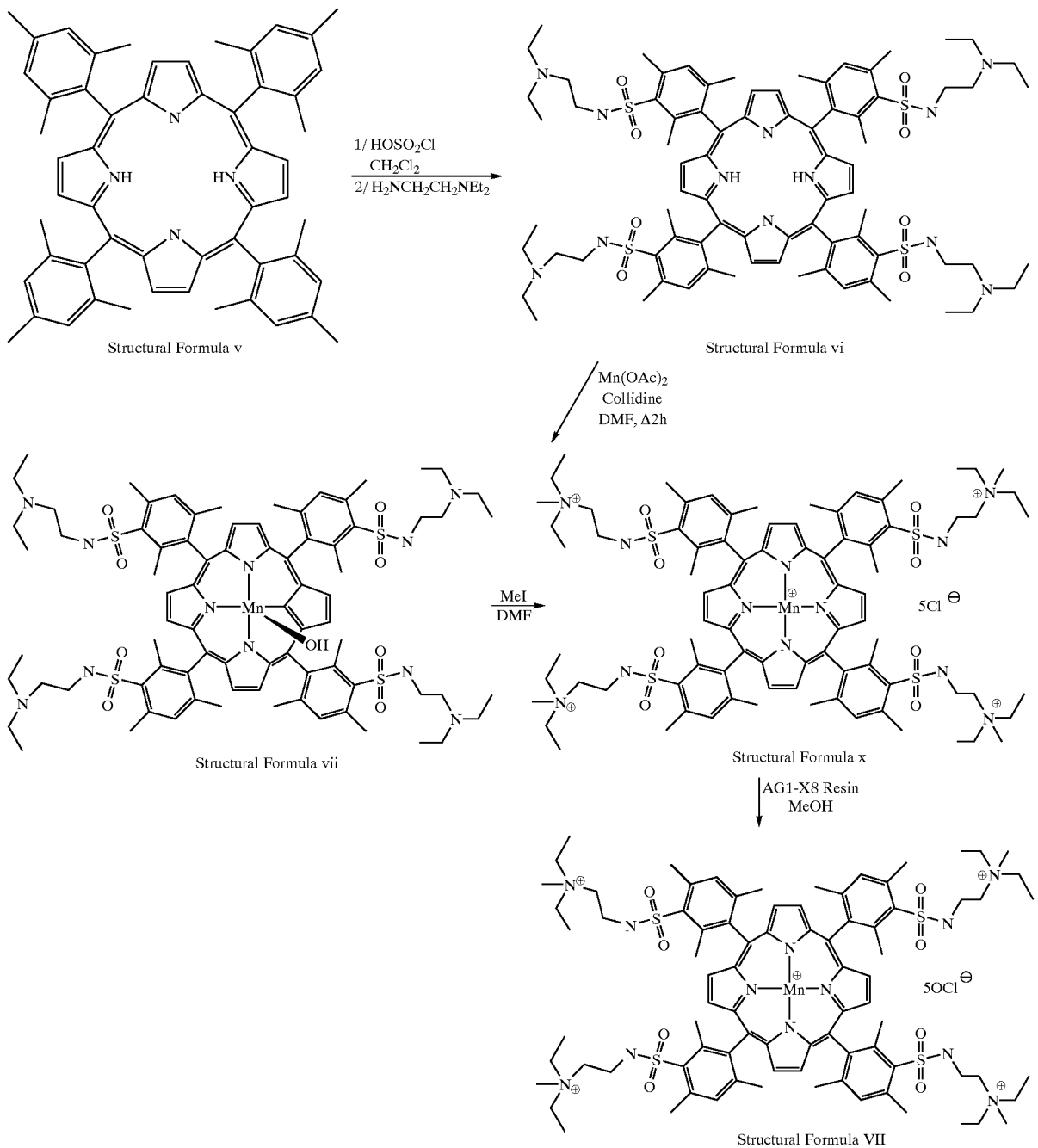

Example 7
(Scheme G)

Synthesis of meso-tetrakis[3-(N-(2-(N,N,N-diethylmethylammonio)ethyl)aminosulfonyl)-2,4,6-trimethylphenyl]porphyrinato diaqua-iron(III) pentaacetate, Structural Formula III The complex of Structural Formula VIII was prepared from Structural Formula vii in two steps as described hereafter.

7.1. Synthesis of meso-tetrakis[3-(N-(2-(N,N,N-diethylmethylammonio)ethyl)aminosulfonyl)-2,4,6-trimethylphenyl]porphyrinato diaqua-iron(III) pentaiodide, Structural Formula xi 8.0 mL of methyl iodide was added to a solution of Structural Formula vii (0.26 g, 0.16 mmol) in 25 mL DMF at room temperature. The mixture was stirred 3 h. After concentration under vacuum, the crude product was dissolved in the minimum quantity of methanol and precipitated by adding diethylether. The powder was filtered off and washed several times with diethylether leaving a dark brown powder Structural Formula xi: 0.37 g (95% yield). UV-visible ($H_2O$) $\lambda(\epsilon\ mol^{-1}\ L\ cm^{-1})$: 330 ($33.0 \times 10^3$), 416 ($93.0 \times 10^3$). Anal.: Calc for $C_{84}H_{120}N_{12}O_8S_4I_5Fe.10H_2O$: C, 41.61; H, 5.82; N, 6.93. Found: C, 39.96; H, 4.70; N, 6.92. MS (ES), m/z 995.0 ($C_{84}H_{120}N_{12}O_8S_4I_3Fe$, z=2).

7.2. Synthesis of meso-tetrakis[3-(N-(2-(N,N,N-diethylmethylammonio)ethyl)aminosulfonyl)-2,4,6-trimethylphenyl]porphyrinato diaqua-iron(III) pentaacetate, Structural Formula VIII To a solution of 0.37 g (0.15 mmol) of Structural Formula xi in 20 mL of methanol, 10.5 g of AG1-X8 acetate form resin was added. The mixture was carefully stirred 3 h at room temperature. The resin was filtered and washed several times with a large quantity of methanol. The filtrate was then concentrated under vacuum. The residue was dissolved in a minimum quantity of methanol and precipitated by adding a large excess of diethylether. The precipitate was filtered, washed with diethylether and dried under vacuum overnight leaving a dark brown powder, Structural Formula VIII: 0.22 g (67% yield). UV-visible ($H_2O$) $\lambda(\epsilon\ mol^{-1}\ L\ cm^{-1})$: 330 ($39.6 \times 10^3$), 416 ($105.9 \times 10^3$). Anal.: Calc for $C_{94}H_{135}N_{12}O_{18}S_4Fe.12H_2O$: C, 53.22; H, 7.55; N, 7.92. Found: C, 52.66; H, 7.28; N, 7.98. MS (ES), m/z 768.5 (z=2), 517.5 (z=3).

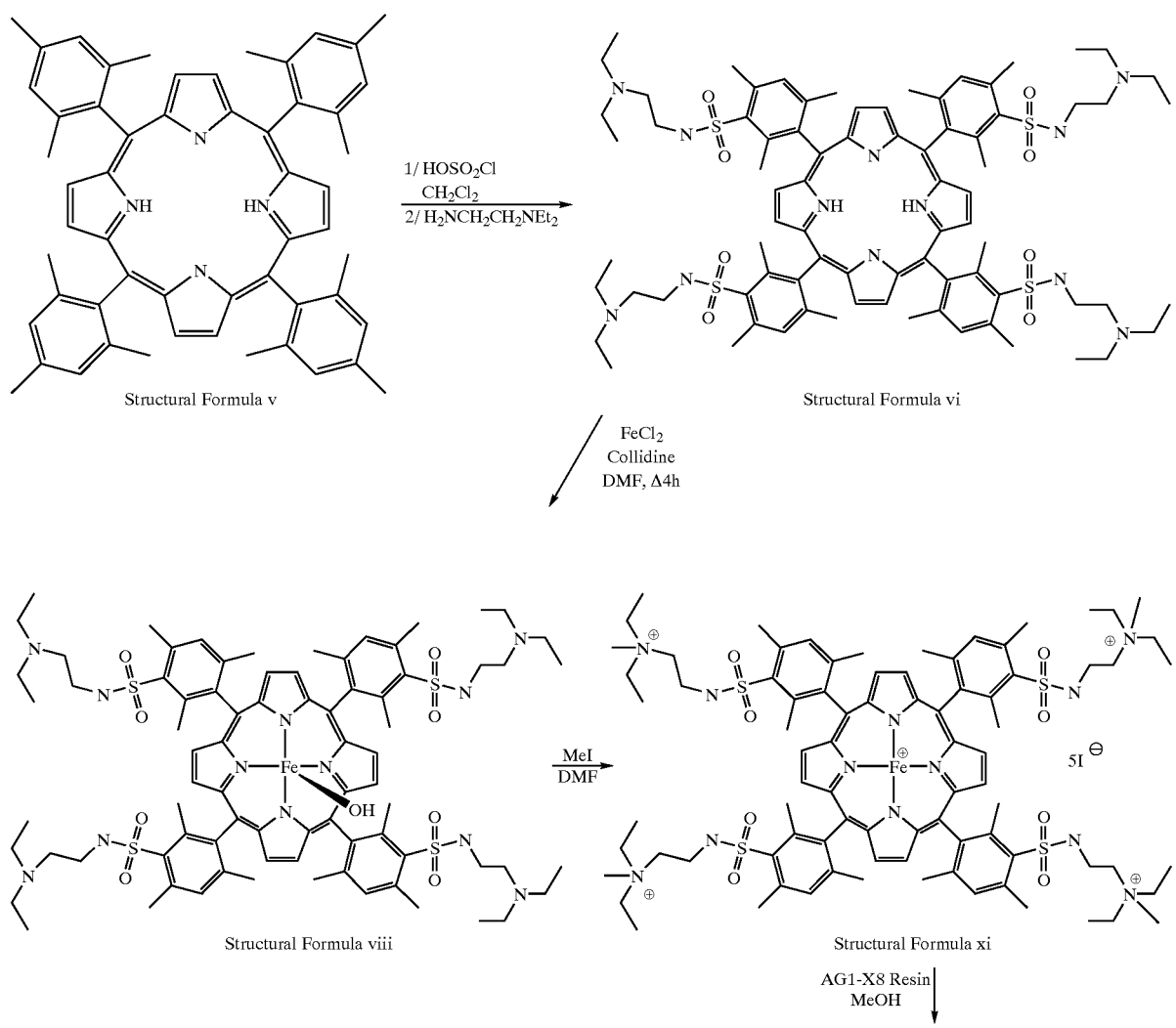

Scheme G

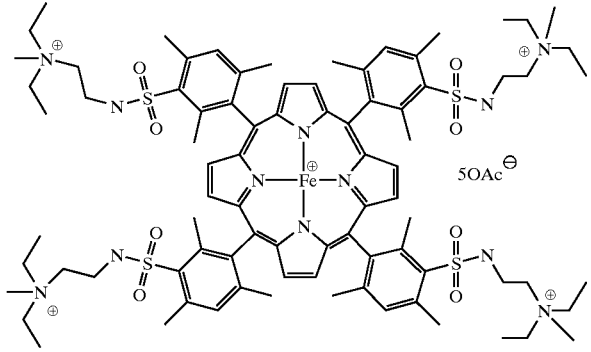

Structural Formula VIII

Example 8
Behavior of these metalloporphyrins with respect to oxidative DNA cleavage One of the lead metalloporphyrin molecules claimed as an SOD mimic (Fridovich et al., *Inorg. Chem.*, 38: 4011–4022 (1999)) is 5,10,15,20 meso-tetrakis(4-methylpyridinimyl) porphyrinato-manganese (III), commonly abbreviated as Mn-TMPyP. Mn-TMPyP is a very efficient effector of oxidative DNA cleavage at nanomolar concentrations when activated in vitro by potassium monopersulfate. A comparative study of some of the different metalloporphyrins described in the instant application with Mn-TMPyP was conducted (Bernadou et al., *Biochemistry*, 28:7268–7275 (1989), Vialas, C. et al., *J. Am. Chem. Soc.*, 122: 2157–2167 (2000), Meunier, B., *Chem Rev*, 92:1411–1456 (1992)).

Oxidative and Reductive Damage on ΦX 174 DNA

In order to strictly quantify the low levels of the DNA cleavage activity of Structural Formula V and Structural Formula VIII, these metalloporphyrin compounds were compared with the DNA cleavage activity of Mn-TMPyP activated by potassium monopersulfate and with bleomycin, a well-known anticancer agent able to cleave tumor cell DNA via the activation of its iron complex. The mechanism of action of this anticancer agent involves an activation of iron-bleomycin by a reducing agent in the presence of air leaving Bleo-Fe(III)-OOH and/or Bleo-Fe(V)=O species.

The DNA cleavage activity was quantified in terms of number of single-strand breaks per DNA molecule according to the equation S=4 Ln Io/I+3 (I–Io), Io=% form I (supercoiled DNA) in the DNA control, and I=% form I in the experiment (see Bernadou et al, *Biochemistry*, 28: 7268–7275, (1989)). This assay is very sensitive and is able to detect very low levels of DNA activity. S values less than S=1.0 are indicative of very low DNA cleavage activity when the compounds are at a concentration of equal to or less than 1000 nM and $KHSO_5$ is present at a concentration of equal to or less than 100 μM.

Experimental Procedures

Materials

Electrophoresis grade agarose was purchase from Sigma Chemical Co. (St. Louis, Mo.); phage ΦX 174 supercoiled DNA (0.25 μg/mL; storage buffer, 10 mM Tris-HCl, pH 7.4, 5 mM NaCl, 0.1 mM EDTA) was obtained from GIBCO BRL Laboratories, Life Technologies SARL (Cergy Pontoise, France). Tris, Hepes, disodium and monopotassium phosphates for the preparation of the different buffers were from Sigma Chemical Co.(St. Louis, Mo.). Potassium monopersulfate is the triple salt $2KHSO_5.KHSO_4K_2SO_4$, known under the tradename Oxone and was obtained from Peroxid-chemie GmbH (Munich, Germany). Ascorbate and $H_2O_2$ (30% w/v) were purchased from Sigma Chemical Co., (St Louis, Mo.) and Aldrich, (Milwaukee, Wis.). Water used for all the solutions was twice distilled.

Synthesis of Bleomycin-iron Complex $FeCl_3.6H_2O$ was purchased from Aldrich and bleomycin from ROGER BELLON Laboratories (Neuilly-sur-Seine, France). 5 μL of 10 mM Fe(III) in water was added to a solution of 1 mL of 50 μM bleomycin in water.

Reaction Conditions for DNA Cleavage and Gel Electrophoresis

ΦX 174 DNA digestion conditions for standard experiments were as follows: commercially available DNA was diluted to 50 μg/mL in phosphate buffer (10 mM, pH 7.5). The reaction involved 5 μL of ΦX 174 DNA (50 μg/mL, 74.8 μM in base pairs), 5 μL of 40 mM phosphate buffer, pH 7.5 with 400 mM NaCl, 5 μL of metalloporphyrin in double-distilled water or 5 μL of iron-bleomycin complex in double-distilled water, and 5 μL of $KHSO_5$ or 5 μL of $H_2O_2$ or 5 μL of ascorbate in double-distilled water. Preincubation of DNA and metalloporphyrins or iron-bleomycin complex was performed for about 15 min. The digestion time in the presence of $KHSO_5$ was 10 min, of $H_2O_2$ was 30 min and of ascorbate was 30 min at 20° C. DNA cleavage was monitored by agarose gel electrophoresis. Reactions with $KHSO_5$ were first quenched by 2 μL of 100 mM Hepes buffer, pH 8. In all cases, reactions were quenched by 5 μL of a stopping reagent. The stopping reagent consisted of 250 mM Hepes buffer, pH 7.4, containing 75% glycerol and 0.05% bromophenol blue. Reaction mixtures were then run in 0.8% agarose slab horizontal gel containing ethidium bromide 1 μl, at constant current (25 mA for 15h), in 89 mM Tris-borate buffer and 2.5 mM EDTA pH 8.3. Bands were located by WV light (254 nm), photographed, and quantitated by microdensitometry. The correction coefficient 1.47±0.30 was used for decreased stainability of form I DNA vs form II DNA and form III DNA.

Results

Activation with $KHSO_5$ (Data Illustrated in FIG. 1 and Table I)

Practically no cleavage activity was noticed with Structural Formula V until 1 μM (0.07 SSBs (Single-strand breaks)) without $KHSO_5$. The presence of $KHSO_5$ in the mixture does not produce a significant increase in DNA cleavage (0.01 to 0.07 SSBs) for 10 μM to 1 μM concentration of Structural Formula V, and 0.03 SSBs for 1 μM concentration of Structural Formula VIII. In all cases, these activities were able to be compared with MnTMPyP which exhibits a large amount of DNA cleavage activity at 10 nM concentration (15.3 SSBs). It is concluded that Structural Formula V, and Structural Formula VIII, in oxidative medium do not exhibit any significant DNA cleavage activity. Compared with Structural Formula V, at the same concentration (10 nM), MnTMPyP is 1527 times more active (obtained from data experiments 6, 9 and 10:1527= (15.3−0.03)/0.01). As thus demonstrated, the Structural Formula V and Structural Formula VIII molecules are non-genotoxic catalysts for the elimination of reduced oxygen species.

TABLE I

Cleavage of ΦX 174 DNA Plasmid (Form I) in the presence of KHSO$_5$.

| | | form % | | | |
|---|---|---|---|---|---|
| Exp | Mixture | I | II | III | S |
| 1 | DNA 3.5 nM | 92 | 8 | 0 | 0 |
| 2 | DNA 3.5 nM/KHSO$_5$.100 μM | 92 | 8 | 0 | 0 |
| 3 | DNA 3.5 nM/Structural Formula V 10 nM | 92 | 8 | 0 | 0 |
| 4 | DNA 3.5 nM/Structural Formula V 100 nM | 92 | 8 | 0 | 0 |
| 5 | DNA 3.5 nM/Structural Formula V 1 μM | 87 | 13 | 0 | 0.07 |
| 6 | DNA 3.5 nM/Structural Formula V 10 nM/KHSO$_5$100 μM | 91 | 9 | 0 | 0.01 |
| 7 | DNA 3.5 nM/Structural Formula V 100 nM/KHSO$_5$100 μM | 90 | 10 | 0 | 0.03 |
| 8 | DNA 3.5 nM/Structural Formula V 1 μM/KHSO$_5$100 μM | 87 | 13 | 0 | 0.07 |
| 9 | DNA 3.5 nM/MnTMPyP 10 nM | 90 | 10 | 0 | 0.03 |
| 10 | DNA 3.5 nM/MnTMPyP 10 nM/KHSO$_5$ 10 μM | 1 | 86 | 13 | 15.3 |
| 11 | DNA 3.5 nM/Structural Formula VIII 1 μM/KHSO$_5$100 μM | 90 | 10 | 0 | 0.03 |

When a compound is generating S values below 1, the compound is considered a non-cleaver of DNA when the compounds are at a concentration of equal to or less than 1000 nM and KHSO$_5$ is present at a concentration of equal to or less than 100 μM.

Figure 2:
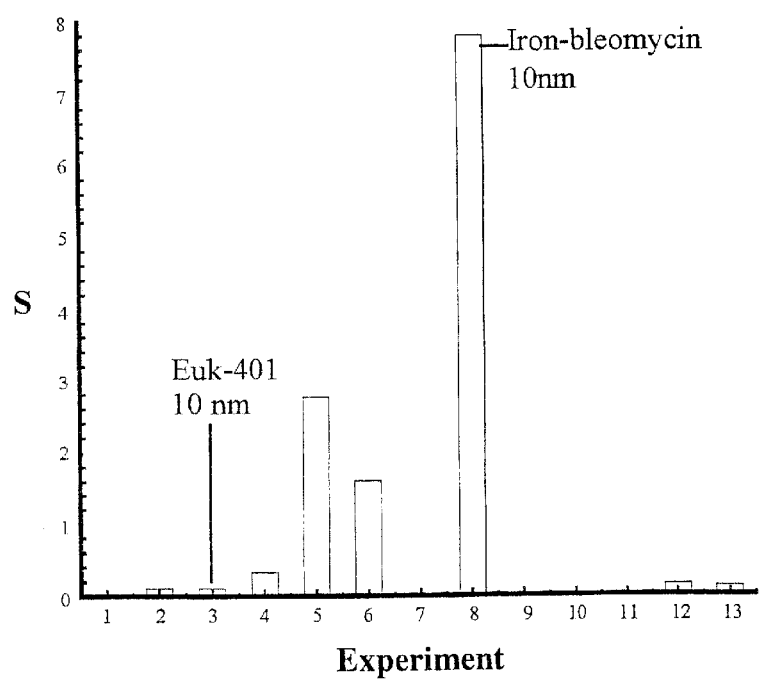
FIG. 2 is a histogram representation of the cleavage of ΦX 174 DNA Plasmid (Form I) in the presence of ascorbate and $H_2O_2$ when a compound of this invention or a control compound (iron-bleomycin) is present.

Activation with Ascorbate in the Presence of Air (Data Illustrated in FIG. 2 and Table II)

The presence of ascorbate with DNA leads to weak DNA cleavage. DNA cleavage activity of Structural Formula V starts to be significant at 1 μM(2.76 SSBs), slightly above that of Structural Formula VIII at the same concentration (1.61 SSBs). However, this activity is far below that of the iron-bleomycin complex: 7.79 SSBs at 10 nM (when used at 1 μM concentration all DNA is cleaved in small fragments and no comparative quantification is possible at such high fragment concentration). Thus, at the same concentration (10 nM), iron-bleomycin is 768 times more active than Structural Formula V (obtained from data experiments 2, 3, 7 and 8: (7.79−0.01)/(0.11−0.10).

Activation with H$_2$O$_2$

In H$_2$O$_2$ medium, Structural Formula V does not exhibit significant DNA cleavage activity. The same result was obtained with Structural Formula VIII

TABLE II

| | | form % | | | |
|---|---|---|---|---|---|
| Exp | Mixture | I | II | III | S |
| 1 | DNA 3.5 nM | 95 | 5 | 0 | 0 |
| 2 | DNA 3.5 nM/Asc.1 mM | 88 | 12 | 0 | 0.1 |
| 3 | DNA 3.5 nM/Structural Formula V 10 nM/Asc.1 mM | 87 | 13 | 0 | 0.11 |
| 4 | DNA 3.5 nM/Structural Formula V 100 nM/Asc.1 mM | 75 | 25 | 0 | 0.34 |
| 5 | DNA 3.5 nM/Structural Formula V 1 μM/Asc.1 mM | 29 | 71 | 0 | 2.76 |

TABLE II-continued

| | | form % | | | |
|---|---|---|---|---|---|
| Exp | Mixture | I | II | III | S |
| 6 | DNA 3.5 nM/Structural Formula VIII 1 μM/Asc.1 mM | 43 | 57 | 0 | 1.61 |
| 7 | DNA 3.5 nM/Bleomycin 10 nM | 94 | 6 | 0 | 0.01 |
| 8 | DNA 3.5 nM/Bleomycin 10 nM/Asc. 1 mM | 7 | 71 | 22 | 7.79 |
| 9 | DNA 3.5 nM/H$_2$O$_2$ 1 mM | 97 | 3 | 0 | 0 |
| 10 | DNA 3.5 nM Structural Formula V 10 nM/H$_2$O$_2$ 1 mM | 94 | 6 | 0 | 0.01 |
| 11 | DNA 3.5 nM Structural Formula V 100 nM/H$_2$O$_2$ 1 mM | 95 | 5 | 0 | 0 |
| 12 | DNA 3.5 nM/Structural Formula V 1 μM/H$_2$O$_2$ 1 mM | 84 | 16 | 0 | 0.16 |
| 13 | DNA 3.5 nM/Structural Formula VIII 1 μM/H$_2$O$_2$ 1 mM | 86 | 14 | 0 | 0.13 |

When a compound is generating S values below 1, the compound is considered a non-cleaver of DNA when the compounds are at a concentration of equal to or less than 1000 nM and KHSO$_5$ is present at a concentration of equal to or less than 100 μM.

Conclusion. Compared with the activity of classical DNA cleavage activity in oxidative medium, the tested compounds exhibit minimal DNA cleavage activity and very low DNA cleavage activity in reductive medium. This cleavage activity is more than two orders of magnitude below that of bleomycin under similar conditions.

Biological Experiments

Example 9

Animal Studies: Efficacy in Delayed Type Hypersensitivity

CBA/J female mice (Jackson Labs, Bar Harbor, ME) 7 weeks of age were pre-sensitized with 3% oxazolone (Sigma Chemical Co., St. Louis, Mo.) in 99.9% acetone, on the abdomen. After 8 days, the mice were challenged with 1.2% oxazolone topically on one ear to induce an inflammatory edema. Either Structural Formula V, Structural Formula IV at a dose of 7 nmoles/ear each, or ethanol, i.e. vehicle control (eight mice per study group), was applied topically to the ear immediately after the oxazolone challenge. Ear edema was measured by comparing the tissue water content (the wet weight minus the dry weight) of the challenged ear to that of the control ear. The percent edema (% water in the right ear-left ear) in the vehicle control was 6.5% and 2.1% and 3.9% for Structural Formula V and Structural Formula IV, respectively at a dose of 7 nmoles/ear. Thus, it is apparent that, Structural Formula V and Structural Formula IV are effective in reducing the percentage of edema caused by an oxidative agent compared to the vehicle alone.

Example 10

Enzyme Activities

Catalase activity was measured by incubating the sample compound with hydrogen peroxide and determining the amount of hydrogen peroxide remaining after a period of time using a colorimetric peroxidase-coupled assay method. 10 μM sample compound and 100 μM hydrogen peroxide in 40 mM sodium phosphate pH 7.4 were incubated together at ambient temperature in a multi-well plate. After the desired reaction period had elapsed, 20 μl of peroxidase/ABTS reagent was added (peroxidase/ABTS reagent contained 100 μl of 50 mM Na phosphate, pH 7.4, 1 mg horseradish peroxidase (1310 U/mg) and 1.6 g ABTS). After five minutes, absorbance at 750 nm was determined. The amount of hydrogen peroxide remaining was calculated based on a standard curve. To compare rates of catalase reaction, the amount of hydrogen peroxide consumed at 20 minutes was determined (See table III). It was also of interest to determine the total number of turnovers completed by the compound before inactivation by hydrogen peroxide. This was assayed under similar conditions, except that 15.8 μM compound was combined with 1582 μM hydrogen peroxide in 5 mM Na phosphate, pH 7.4. Reactions were allowed to proceed to completion and then the amount of hydrogen peroxide remaining was determined as described above. Results showing catalase consumed in the turnover assay (nmoles hydrogen peroxide per nmole compound) are also shown in Table III.

Peroxidase activity was measured by incubating 10 μM compound, 200 μM hydrogen peroxide and 500 μM ABTS in 50 mM sodium phosphate, pH 8.1. The rate of ABTS oxidation was monitored at 740 nm and initial rates (change in absorbance per min.) determined. These are also shown in Table III.

Superoxide Dismutase Activity was measured by incubating the compound with a superoxide generating system (Xanthine, 60 μM-Xanthine Oxidase, 0.009 units/ml) and a detector molecule (Cytochrome C, 27.8 μM). Upon reacting with a molecule of superoxide, Cytochrome C undergoes a spectrum-shift which can be detected as an increase in absorbance at 550 nm. In this assay procedure, the reactant concentrations were adjusted to give a reaction rate close to 0.1 AU/min. at 2–3 min. after the reaction began. Addition of compounds with Superoxide Dismutase activity reduce the rate of absorbance change. Compounds were assayed at several concentrations (typically at 0, 2, 4, and 8 μM) and the resulting rates were graphed and fitted to a linear regression formula. The linear regression formula was then solved to determine the concentration of compound required to reduce the reaction rate to 50% of the rate without compound present ($IC_{50}$).

TABLE III

SUMMARY OF THE ENZYMATIC ACTIVITIES

| COMPOUND | CATA-LASE* Rate at 20 mins. | CATA-LASE** $H_2O_2$ Consumption | PEROX-IDASE Initial Rate | Cyt C SOD 1/($IC_{50}$, μM) |
|---|---|---|---|---|
| Structural Formula II | 1.6 | 42.4 | 0.0151 | 0.034 |
| Structural Formula VI | 2.4 | 42 | 0.0011 | 0.041 |
| Structural Formula III | 0.3 | 4.7 | 0.0363 | 0.045 |
| Structural Formula IV | 1.0 | 189.9 | 0.021 | 0.043 |
| Structural Formula VII | 1.3 | 166.6 | 0.0025 | 0.013 |
| Structural Formula V | 6.4 | 36.1 | 0.0443 | 0.067 |
| MnTMPyP | 3.4 | 31.1 | 0.0672 | 0.143 |
| MnTBAP*** | 0.4 | 38.5 | 0.0304 | 0.015 |

*nmole $H_2O_2$/nmole Structural Formula compound, over 20 minutes.
**nmole $H_2O_2$/nmole Structural Formula compound, total
***Mn(III) tetrakis (4-benzoic acid) porphyrin While this invention has been particularly shown and described with references to preferred embodiments thereof, it will be understood by those skilled in the art that various changes in form and details may be made therein without departing from the scope of the invention encompassed by the appended claims.

We claim:
1. A compound of Structural Formula I:

Structural Formula I

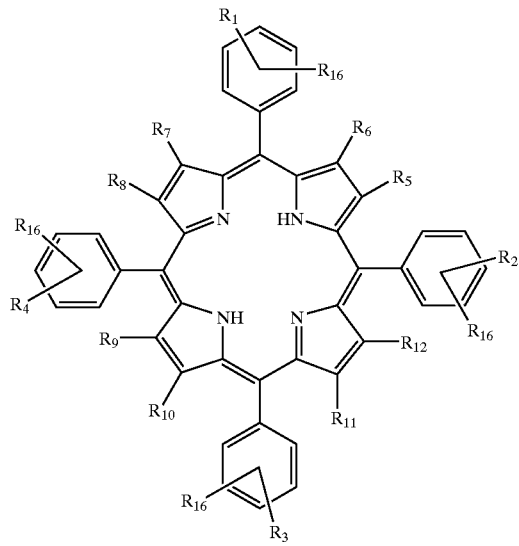

or a complex thereof with a first row transition metal ion, wherein $R_1$, $R_2$, $R_3$ and $R_4$ are the same or different and are each a group of the formula

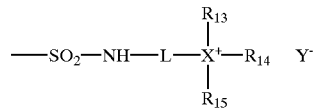

wherein L is a linker of 2 to 12 atoms in length, wherein said atoms are carbon atoms optionally interspersed with from 1 to 4 heteroatoms selected from the group consisting of oxygen, nitrogen and sulphur;

X is nitrogen or phosphorus;

$R_{13}$, $R_{14}$ and $R_{15}$ are each, independently, hydrogen, alkyl or arylalkyl; and Y— is a monovalent anion;

$R_5$, $R_6$, $R_7$, $R_8$, $R_9$, $R_{10}$, $R_{11}$ and $R_{12}$ are each independently selected from the group consisting of hydrogen, alkyl and halo; and each $R_{16}$ independently represents one or more substituents independently selected from the group consisting of hydrogen, hydroxy, halo and alkyl.

2. The compound of claim 1 wherein $R_1$, $R_2$, $R_3$ and $R_4$ are the same.

3. The compound of claim 1 wherein $R_5$, $R_6$, $R_7$, $R_8$, $R_9$, $R_{10}$, $R_{11}$, and $R_{12}$ are each hydrogen.

4. The compound of claim 1 wherein L is selected from the group consisting of linear or branched $C_2$–$C_{12}$ alkylene and linear or branched alkylene interspersed at one or more positions with a heteroatom selected from the group consisting of oxygen, nitrogen and sulphur.

5. The compound of claim 2 wherein $R_{13}$, $R_{14}$ and $R_{15}$ are each independently selected from the group consisting of hydrogen and linear and branched $C_1$–$C_{20}$ alkyl.

6. The compound of claim 4 wherein $R_{13}$, $R_{14}$ and $R_{15}$ are each independently hydrogen or methyl or ethyl.

7. The compound of claim 5 wherein $R_{13}$ and $R_{14}$ are each independently, methyl or ethyl and $R_{15}$ is hydrogen.

8. The compound of claim 3 wherein L is a linear $C_2$–$C_6$ alkylene group.

9. The compound of claim 7 wherein L is an ethylene group.

10. The compound of claim 2 wherein $R_{16}$ represents hydrogen.

11. The compound of claim 2 wherein $R_1$, $R_2$, $R_3$ and $R_4$ are each connected to the 3 position of the phenyl ring and $R_{16}$ represents methyl groups at the 2, 4 and 6 positions of the phenyl ring.

12. The compound of claim 2 wherein:

$R_5$, $R_6$, $R_7$, $R_8$, $R_9$, $R_{10}$, $R_{11}$ and $R_{12}$ are each hydrogen;

$R_{16}$ represents hydrogen;

$R_1$, $R_2$, $R_3$ and $R_4$ are connected to the 3 or 4 position of the phenyl ring;

L is an ethylene group; and $R_{13}$, $R_{14}$ and $R_{15}$ are each, independently, hydrogen, methyl or ethyl.

13. A compound selected from the group of ligands consisting of:

meso-tetrakis[4-(N-(2-(N,N-dimethylamino)ethyl) aminosulfonyl)phenyl]porphyrinato;

meso-tetrakis[4-(N-(2-(N,N-dimethylammonio)ethyl) aminosulfonyl)phenyl]porphyrinato $A^{4-}$;

meso-tetrakis[4-(N-(2-(N,N,N-trimethylammonio)ethyl) aminosulfonyl)phenyl]porphyrinato $A^{4-}$;

meso-tetrakis[4-(N-(2-(N,N-diethylamino)ethyl) aminosulfonyl)phenyl]porphyrinato;

meso-tetrakis[4-(N-(2-(N,N-diethylammonio)ethyl) aminosulfonyl)phenyl]porphyrinato $A^{4-}$;

meso-tetrakis[4-(N-(2-(N,N,N-triethylammonio)ethyl) aminosulfonyl)phenyl]porphyrinato $A^{4-}$;

meso-tetrakis[4-(N-(2-(N,N,N-ethyldimethylammonio) ethyl)aminosulfonyl)phenyl]porphyrinato $A^{4-}$;

meso-tetrakis[4-(N-(2-(N,N,N-diethylmethylammonio) ethyl)aminosulfonyl)phenyl]porphyrinato $A^{4-}$;

meso-tetrakis[3-(N-(2-(N,N-dimethylamino)ethyl) aminosulfonyl)-2,4,6-trimethylphenyl]porphyrinato;

meso-tetrakis[3-(N-(2-(N,N-dimethylammonio)ethyl) aminosulfonyl)-2,4,6-trimethylphenyl]porphyrinato $A^{4-}$;

meso-tetrakis[3-(N-(2-(N,N-diethylammonio)ethyl) aminosulfonyl)-2,4,6-trimethylphenyl]porphyrinato $A^{4-}$;

meso-tetrakis[3-(N-(2-(N,N-diethylamino)ethyl) aminosulfonyl)-2,4,6-trimethylphenyl]porphyrinato;

meso-tetrakis[3-(N-(2-(N,N,N-triethylammonio)ethyl) aminosulfonyl)-2,4,6-trimethylphenyl]porphyrinato $A^{4-}$;

meso-tetrakis[3-(N-(2-(N,N,N-trimethylammonio)ethyl) aminosulfonyl)-2,4,6-trimethylphenyl]porphyrinato $A^{4-}$;

meso-tetrakis[3-(N-(2-(N,N-ethyldimethylammonio)ethyl) aminosulfonyl)-2,4,6-trimethylphenyl]porphyrinato $A^{4-}$;

meso-tetrakis[3-(N-(2-(N,N-diethylmethylammonio) ethyl)aminosulfonyl)-2,4,6-trimethylphenyl]porphyrinato $A^{4-}$;

meso-tetrakis[4-(N-(2-(N,N-ethylmethylamino)ethyl) aminosulfonyl)phenyl]porphyrinato;

meso-tetrakis[4-(N-(2-(N,N-ethylmethylammonio)ethyl) aminosulfonyl)phenyl]porphyrinato $A^{4-}$;

meso-tetrakis[3-(N-(2-(N,N-ethylmethylammonio)ethyl) aminosulfonyl)-2,4,6-trimethylphenyl]porphyrinato $A^{4-}$; and meso-tetrakis[3-(N-(2-(N,N-ethylmethylammonio)ethyl) aminosulfonyl)-2,4,6-trimethylphenyl]porphyrinato $A^{4-}$;

meso-tetrakis[4-(N-(2-(N,N-dimethylphosphonio)ethyl) aminosulfonyl)phenyl]porphyrinato;

meso-tetrakis[4-(N-(2-(N,N-diethylphosphonio)ethyl) aminosulfonyl)phenyl]porphyrinato;

meso-tetrakis[3-(N-(2-(N,N-dimethylphosphonio)ethyl) aminosulfonyl)-2,4,6-trimethylphenyl]porphyrinato;

meso-tetrakis[3-(N-(2-(N,N-diethylphosphonio)ethyl) aminosulfonyl)-2,4,6-trimethylphenyl]porphyrinato $A^{4-}$;

meso-tetrakis[3-(N-(2-(N,N-diethylphosphonio)ethyl) aminosulfonyl)-2,4,6-trimethylphenyl]porphyrinato; and meso-tetrakis[4-(N-(2-(N,N-ethylmethylphosphonio)ethyl) aminosulfonyl)phenyl]porphyrinato;

or a complex thereof with a first row transition metal ion; wherein $A^{4-}$ represents from 1 to 4 anions having a total electronic charge of $4^-$.

14. The compound of claim 13 wherein said compound is a complex with a transition metal ion selected from the group consisting of manganese, iron, cobalt, copper and zinc.

15. The compound of claim 14 wherein the transition metal ion is Mn(III) or Fe(III) and the transition metal ion is bonded to an additional anionic ligand.

16. The compound of claim 15 wherein the additional anionic ligand is selected from the group consisting of fluoro, chloro, bromo, iodo, hydroxyl and $ZCOO^-$, wherein Z is an alkyl, aryl or arylalkyl group.

17. The compound of claim 16 wherein the additional anionic ligand is hydroxyl, chloro or acetato.

18. A pharmaceutical formulation comprising one or more pharmaceutically acceptable carriers, diluents or excipients and a therapeutically effective amount of at least one compound represented by Structural Formula I:

Structural Formula I

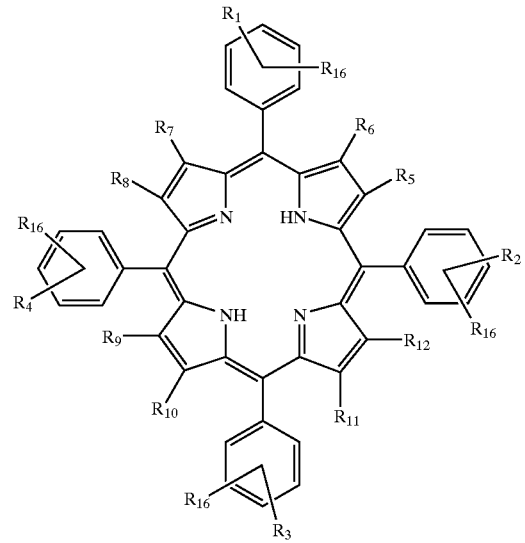

or a complex thereof with a first row transition metal ion, wherein $R_1$, $R_2$, $R_3$ and $R_4$ are the same or different and are each a group of the formula

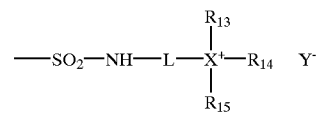

wherein L is a linker of 2 to 12 atoms in length, wherein said atoms are carbon atoms optionally interspersed with from 1 to 4 heteroatoms selected from the group consisting of oxygen, nitrogen and sulphur;

X is nitrogen or phosphorus;

$R_{13}$, $R_{14}$ and $R_{15}$ are each, independently, hydrogen, alkyl or arylalkyl; and Y— is a monovalent anion;

$R_5$, $R_6$, $R_7$, $R_8$, $R_9$, $R_{10}$, $R_{11}$ and $R_{12}$ are each independently selected from the group consisting of hydrogen, alkyl and halo; and each $R_{16}$ independently represents one or more substituents independently selected from the group consisting of hydrogen, hydroxy, halo and alkyl.

19. A pharmaceutical formulation of claim 18 wherein the compound is selected from the group consisting of meso-tetrakis[4-(N-(2-(N,N-diethylamino)ethyl)aminosulfonyl)phenyl]porphyrinato manganese(III) pentachloride, meso-tetrakis[4-(N-(2-(N,N-diethylammonio)ethyl) aminosulfonyl)phenyl]porphyrinato diaqua-iron (III) pentachloride, meso-tetrakis[3-(N-(2-(N,N-diethylammonio)ethyl)aminosulfonyl)-2,4,6-trimethylphenyl]porphyrinato diaqua-manganese(III) pentachloride, meso-tetrakis[3-(N-(2-(N,N-diethylammonio)ethyl)aminosulfonyl)-2,4,6-trimethylphenyl]porphyrinato diaqua-iron (III) pentachloride, meso-tetrakis[4-(N-(2-N,N,N-diethylmethylammonio)ethyl)aminosulfonyl)phenyl] porphyrinato diaqua-manganese(III) pentaacetate, meso-tetrakis[3-(N-(2-(N,N,N-diethylmethylammonio)ethyl) aminosulfonyl)-2,4,6-trimethylphenyl]porphyrinato diaqua-manganese(III) pentaacetate, and meso-tetrakis[3-(N-2-(N,N,N,-diethylmethylammonio)ethyl)aminosulfonyl)2,4,6-trimethylphenyl]porphyrinato diaqua-iron (III) pentaacetate.

20. A pharmaceutical formulation of claim 18 wherein the compound is non-genotoxic.

21. A method of treating, preventing or arresting a free radical associated disease or condition comprising administering to a mammal in need of a therapeutically effective amount of a compound, represented by Structural Formula I:

Structural Formula I

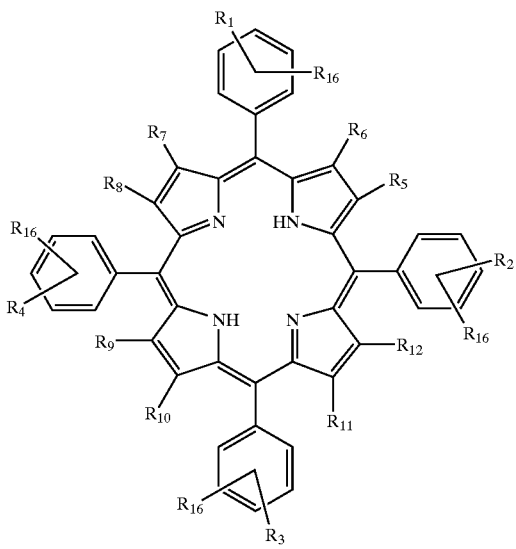

or a complex thereof with a first row transition metal ion, wherein $R_1$, $R_2$, $R_3$ and $R_4$ are the same or different and are each a group of the formula

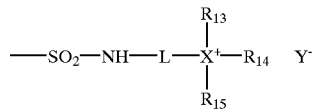

wherein L is a linker of 2 to 12 atoms in length, wherein said atoms are carbon atoms optionally interspersed with from 1 to 4 heteroatoms selected from the group consisting of nitrogen, oxygen and sulfur;

X is nitrogen or phosphorus;

$R_{13}$, $R_{14}$ and $R_{15}$ are each, independently, hydrogen, alkyl or arylalkyl; and Y— is a monovalent anion;

$R_5$, $R_6$, $R_7$, $R_8$, $R_9$, $R_{10}$, $R_{11}$ and $R_{12}$ are each independently selected from the group consisting of hydrogen, alkyl and halo; and each $R_{16}$ independently represents one or more substituents independently selected from the group consisting of hydrogen, hydroxy, halo and alkyl; wherein said administering of the compound alleviates or prevents free radical associated disease or conditions.

22. A method of claim 21 wherein the compound is selected from the group consisting of: Structural Formula II, Structural Formula III, Structural Formula IV, Structural Formula V, Structural Formula VI, Structural Formula VII and Structural Formula VIII.

23. A method of claim 21 wherein the compound is non-genotoxic.

24. A method of claim 21, wherein the free radical associated disease or condition is damage resulting from a stroke, Alzheimer's disease, dementia, Parkinson's disease, Lou Gehrig disease, motor neuron disorders, Huntington's disease, cancer, multiple sclerosis, systemic lupus erythematosus, scleroderma, eczema, dermatitis, delayed type hypersensitivity, psoriasis, gingivitis, adult respiratory distress syndrome, septic shock, multiple organ failure, inflammatory diseases, asthma, allergic rhinitis, pneumonia, emphysema, chronic bronchitis, AIDS, inflammatory bowel disease, gastric ulcers, pancreatitis, transplantation rejection, atherosclerosis, hypertension, congestive heart failure, myocardial ischemic disorders, angioplasty, endocarditis, retinopathy of prematurity, cataract formation, uveitis, rheumatoid arthritis, oxygen toxicity, herpes simplex infection, burns, osteoarthritis and aging.

25. A compound represented by the following Structural Formula II:

Structural Formula II
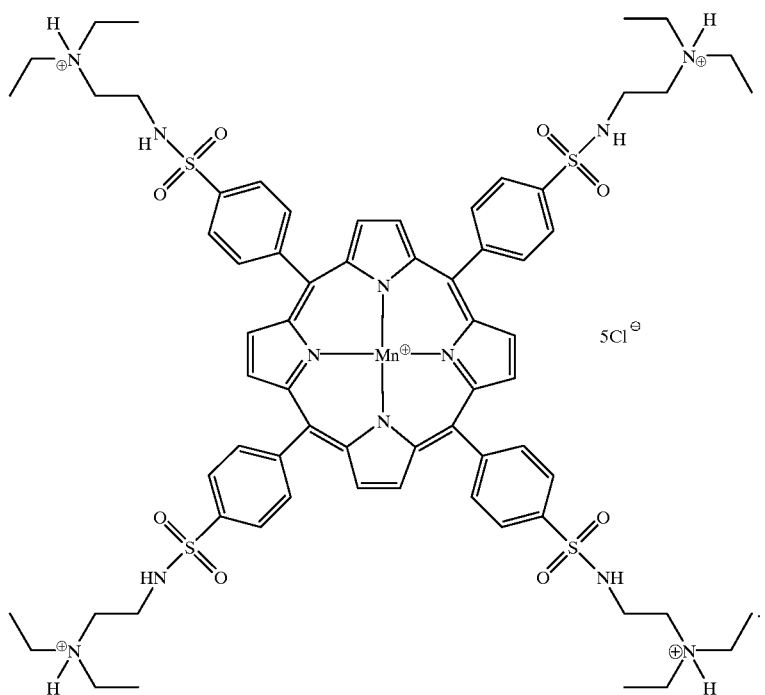
26. A compound represented by the following Structural Formula III:
Structural Formula III
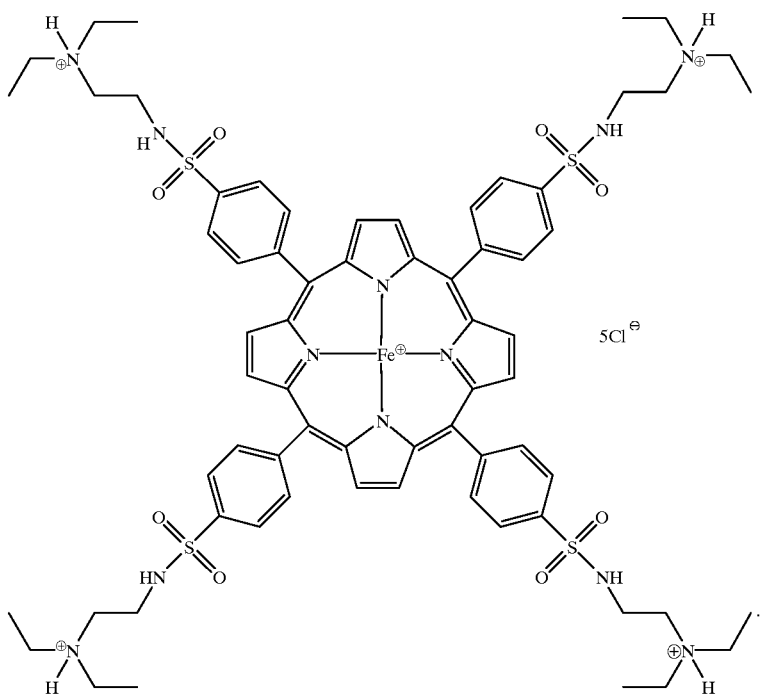
27. A compound represented by the following Structural Formula IV:

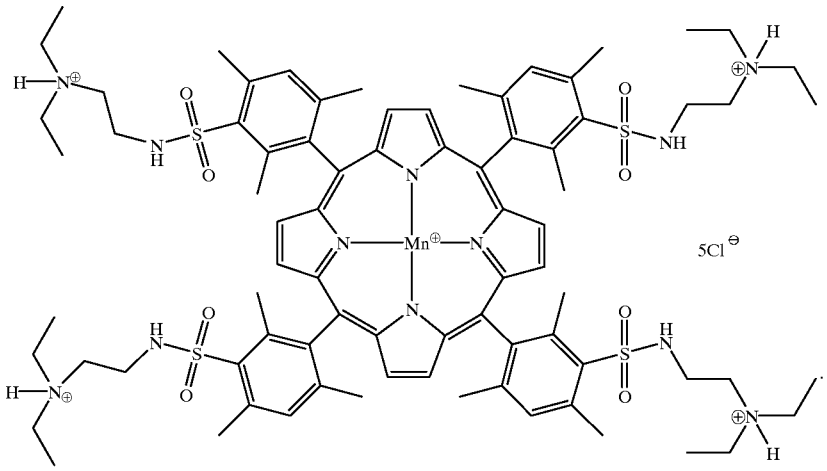
Structural Formula IV
28. A compound represented by the following Structural Formula V:
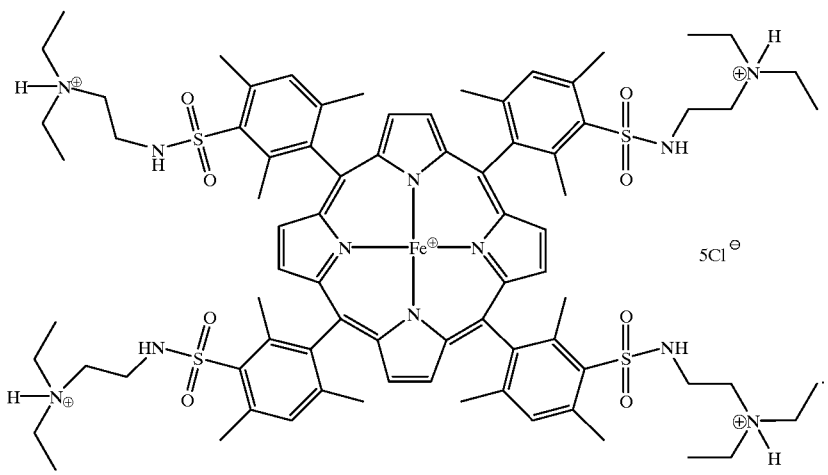
Structural Formula V
29. A compound represented by the following Structural Formula VI:

Structural Formula VI
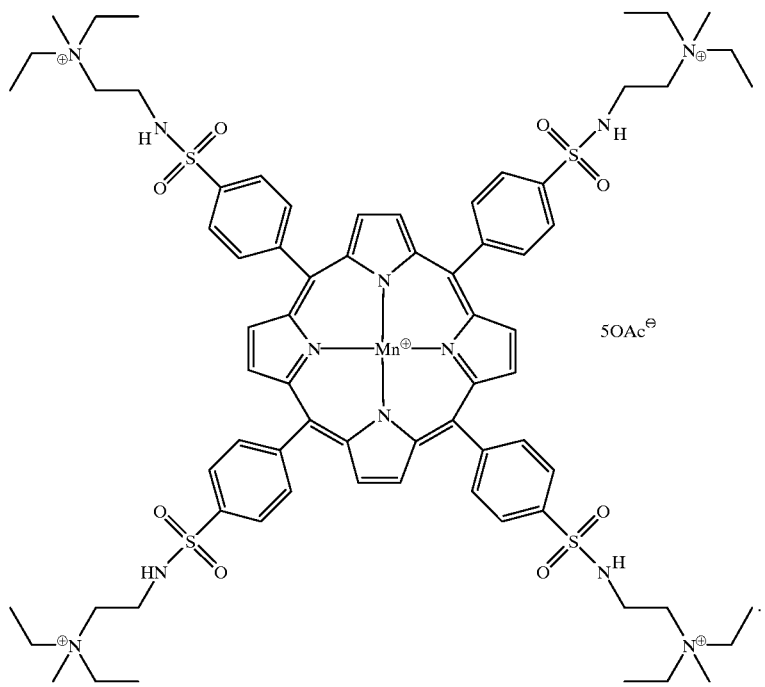
30. A compound represented by the following Structural Formula VII:
Structural Formula VII
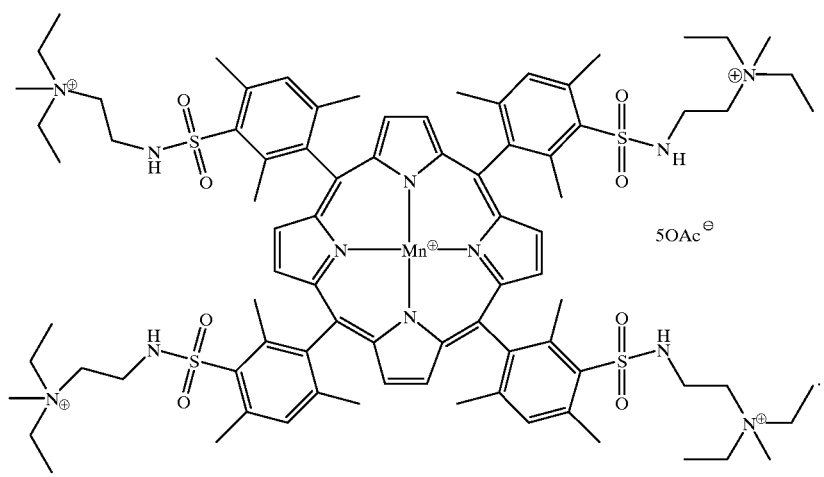
31. A compound represented by the following Structural Formula VIII:

Structural Formula VIII

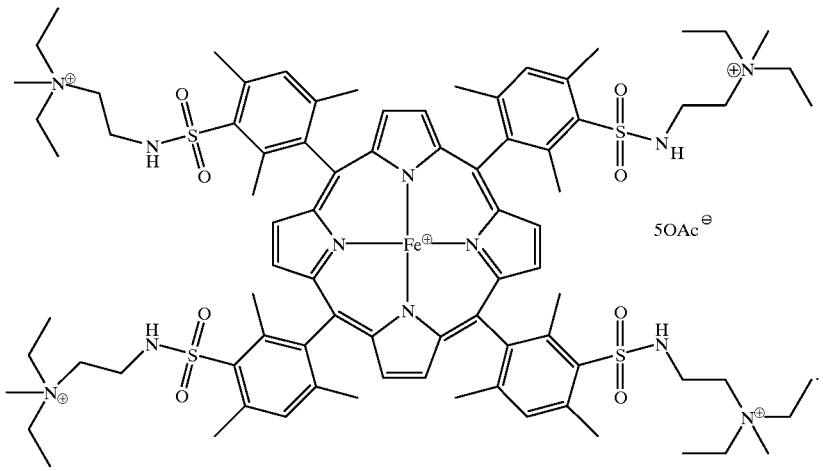

32. A method of preparing the compound, meso-tetrakis[4-(N-(2-(N,N-diethylamino)ethyl)aminosulfonyl)phenyl] porphyrinato manganese (III) pentachloride, represented by Structural Formula II, comprising:

(a) reacting meso-tetraphenyl porphyrin, Structural Formula i, with chlorosulfonic acid and subsequently N,N-diethylenediamine thereby forming first intermediate, Structural Formula ii, meso-tetrakis[4-(N-(2-(N,N-diethylamino)ethyl)aminosulfonyl)phenyl]porphyrin;

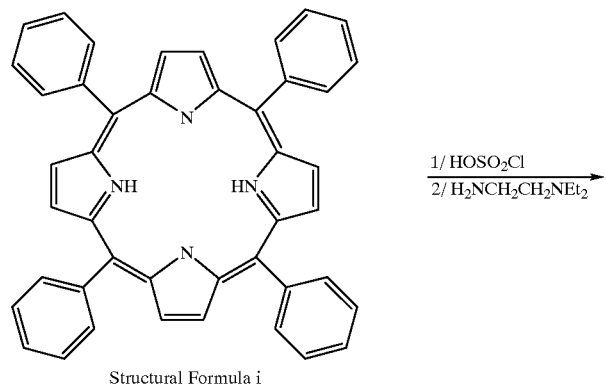

Structural Formula i

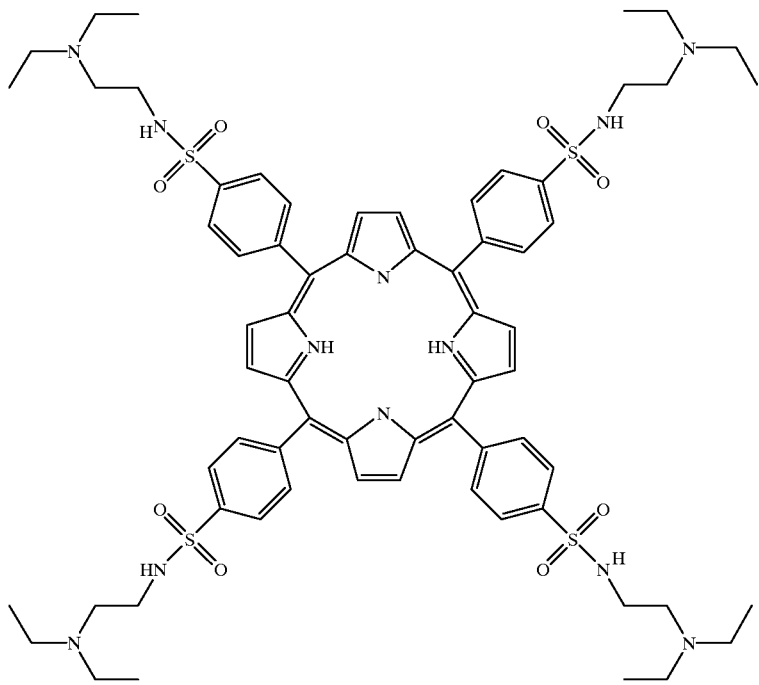
Structural Formula ii
(b) reacting first intermediate, Structural Formula ii, with Mn(OAc)₂ in the presence of a hindered base, thereby forming second intermediate, Structural Formula iii, meso-tetrakis[4-(N-(2-(N,N-diethylamino))aminosulfonyl)phenyl]porphyrinato hydroxo-manganese (III); and
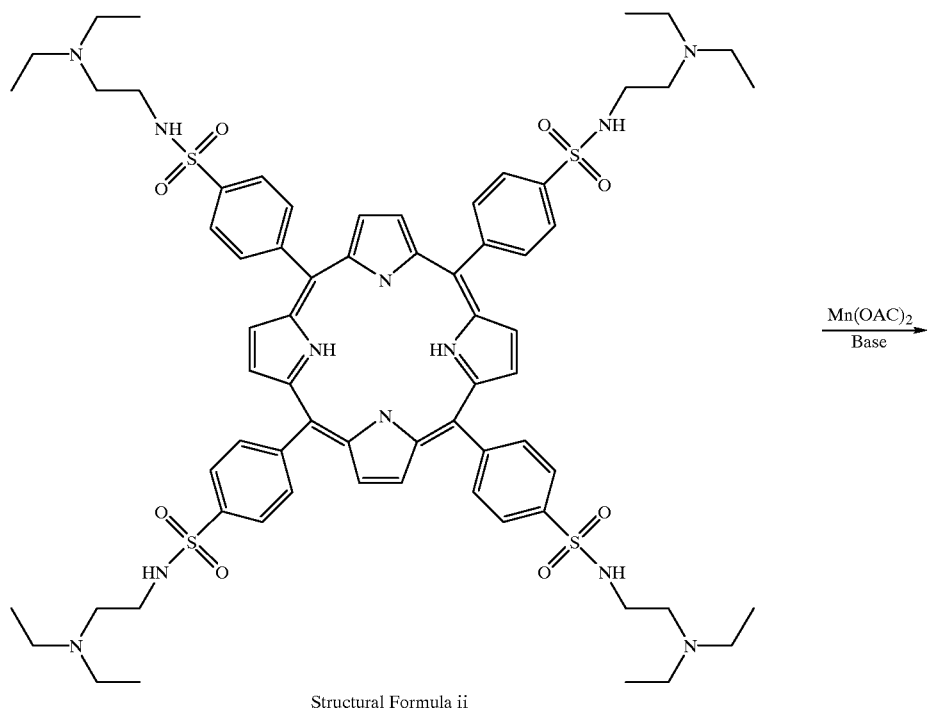
Structural Formula ii

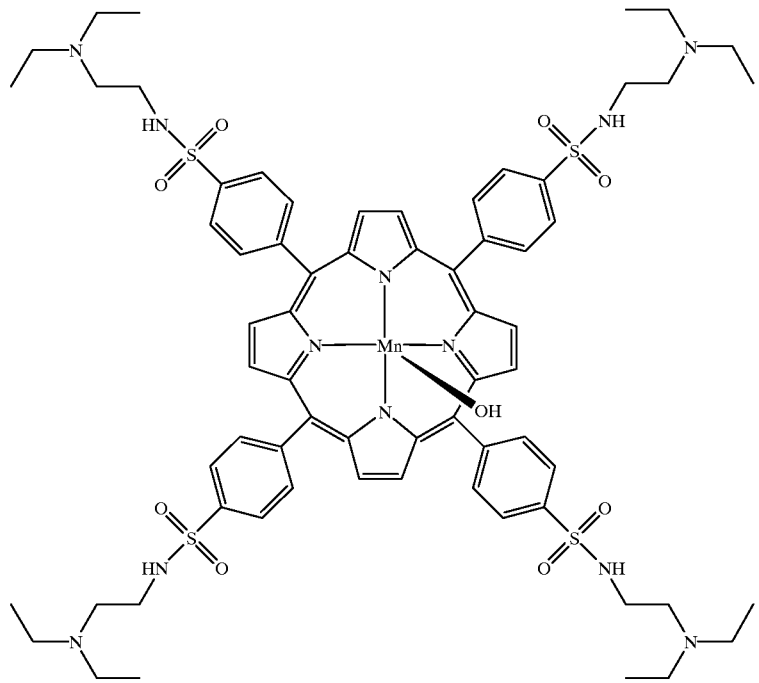

Structural Formula iii (c) reacting second intermediate, Structural Formula iii, meso-tetrakis[4-(N-(2-(N,N-diethylamino)ethyl) aminosulfonyl)phenyl]porphyrinato hydroxo-manganese (III) with hydrochloric acid thereby forming Structural Formula II, meso-tetrakis[4-(N-(2-(N,N-diethylamino)ethyl)aminosulfonyl)phenyl] porphyrinato diaqua-manganese (III) pentachloride,

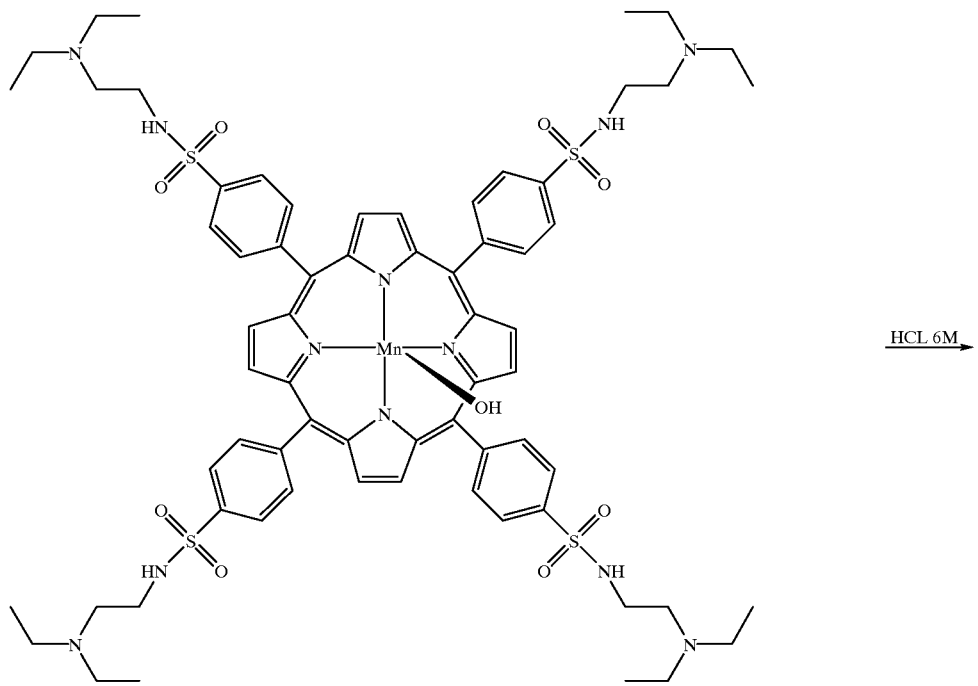

Structural Formula iii

HCL 6M

-continued

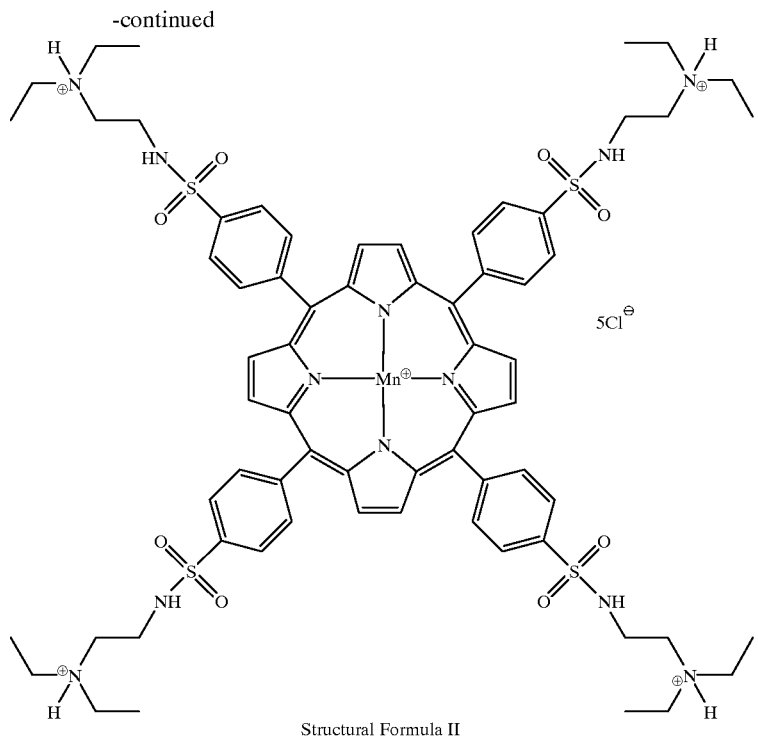

Structural Formula II

33. A method of preparing compound, meso-tetrakis[4-(N-(2-(N,N-diethylammonio)ethyl)aminosulfonyl)phenyl] porphyrinato diaqua-iron(III) pentachloride, represented by Structural Formula III, comprising:

(a) reacting meso-tetraphenyl porphyrin, Structural Formula i with chlorosulfonic acid and subsequently N,N-diethylenediamine thereby forming first intermediate, Structural Formula ii, meso-tetrakis[4-(N-(2-(N,N-diethylamino)ethyl)aminosulfonyl)phenyl]porphyrin;

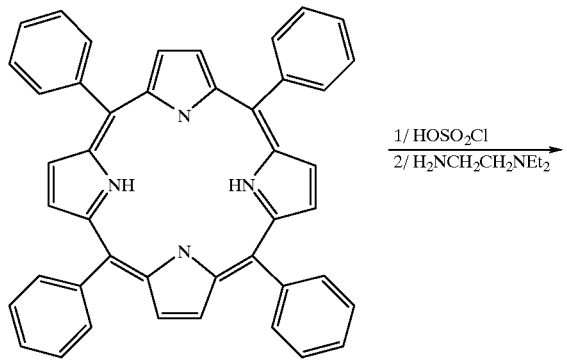

Structural Formula i

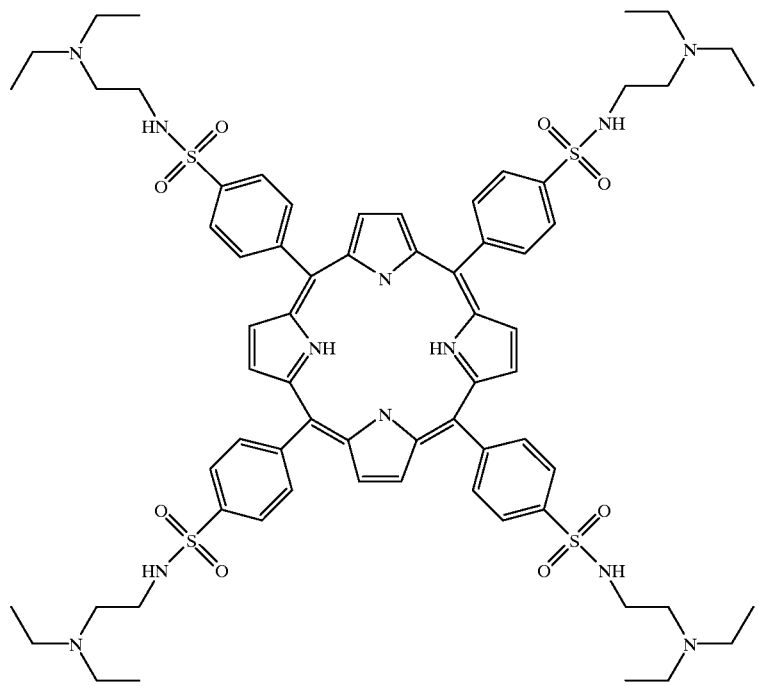
Structural Formula ii
(b) reacting first intermediate, Structural Formula ii, with FeCl$_2$ in the presence of a hindered base, thereby forming second intermediate, Structural Formula iv,
-oxo-[meso-tetrakis[4-(N-(2-(N,N-diethylamino)ethyl)aminosulfonyl)phenyl]porphyrinato iron(III); and
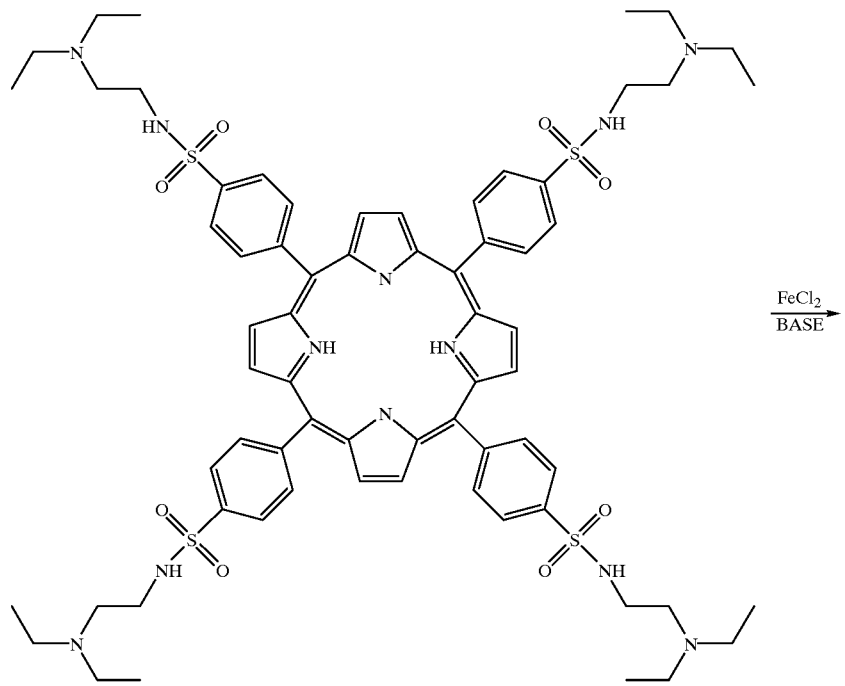
Structural Formula ii -continued
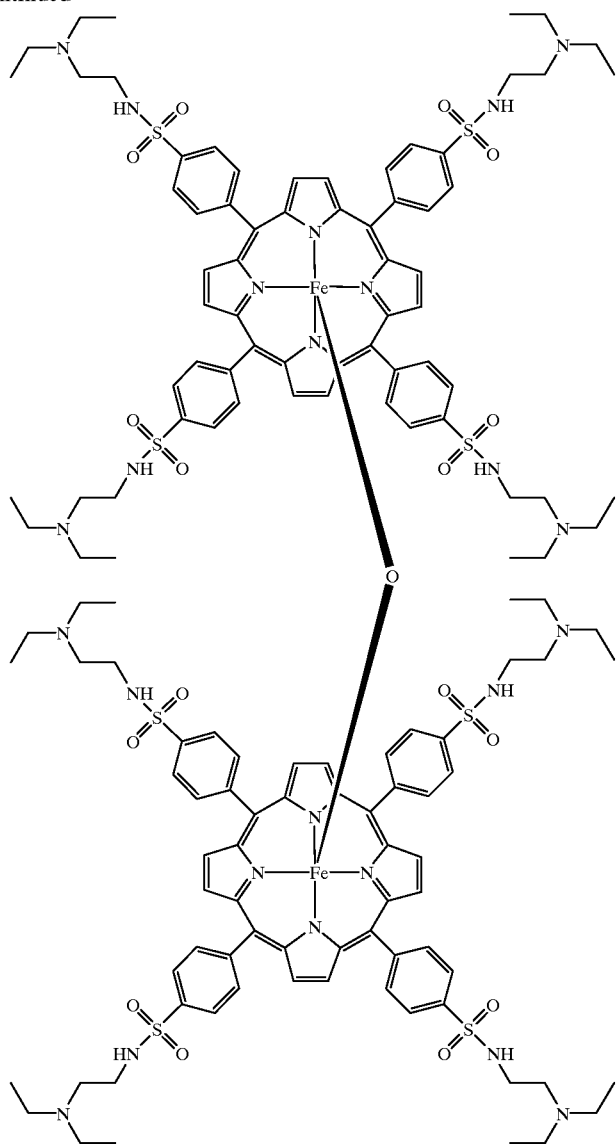
Structural Formula iv
(c) reacting second intermediate, Structural Formula iv, μ-oxo-[meso-tetrakis[4-(N-(2-(N,N-diethylamino)ethyl)aminosulfonyl)phenyl]porphyrinato iron(III) with hydrochloric acid, thereby forming Structural Formula III, meso-tetrakis[3-(N-(2-(N,N-diethylammonio)ethyl)aminosulfonyl)phenyl]porphyrinato diaqua-iron(III) pentachloride,

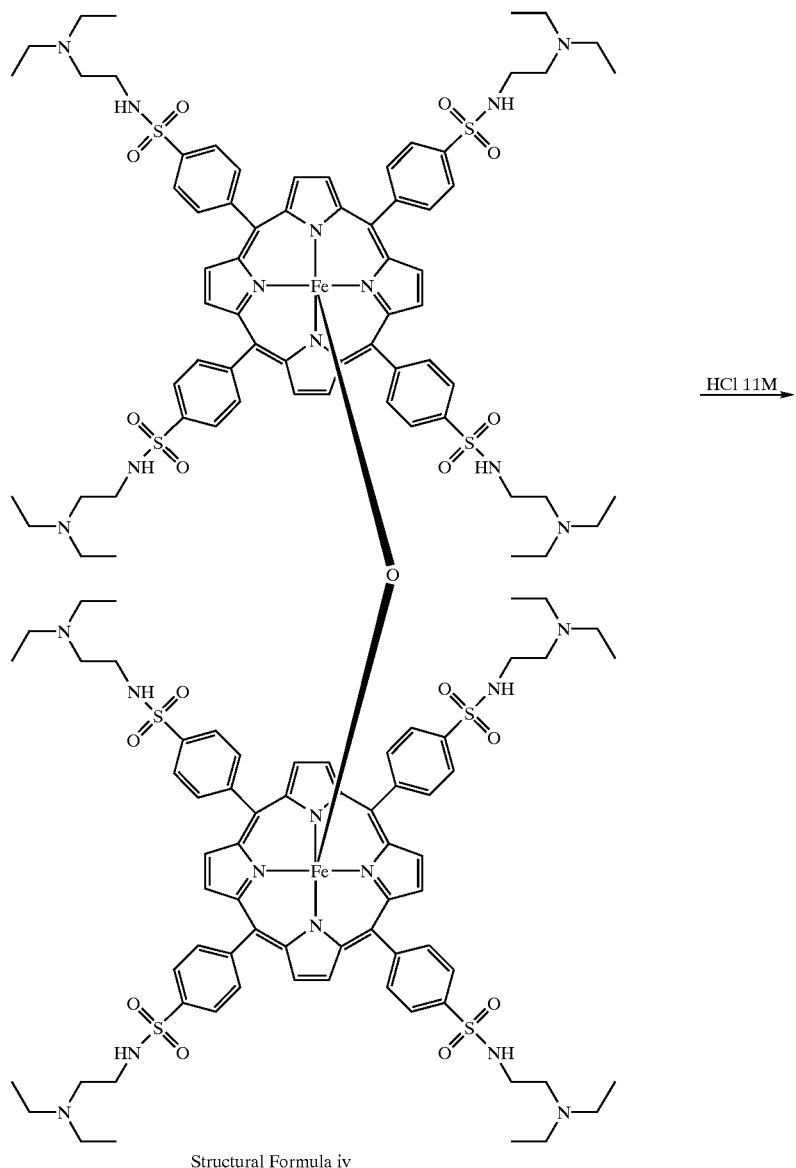
HCl 11M
Structural Formula iv

-continued

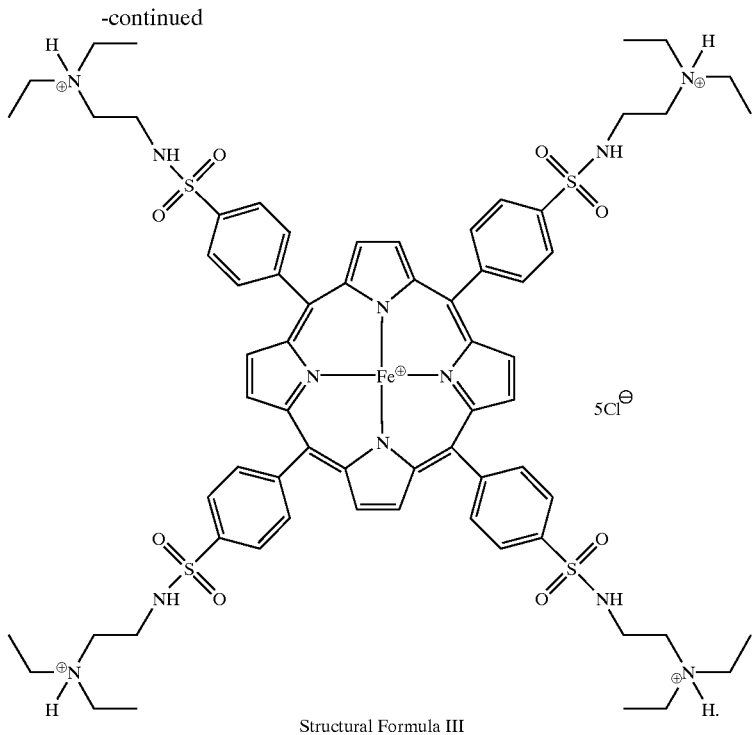

Structural Formula III

34. A Method of preparing compound meso-tetrakis[3-(N-(2-(N,N-diethylammonio)ethyl)aminosulfonyl)-2,4,6-trimethylphenyl]porphyrinato diaqua-manganese (III) pentachloride represented by Structural Formula IV comprising:

(a) reacting meso-tetrakis(2,4,6-trimethylphenyl) porphyrin, Structural Formula v with chlorosulfonic acid and subsequently N,N-diethylenediamine thereby forming first intermediate, Structural Formula vi, meso-tetrakis[3,(N-(2-(N,N-diethylamino)ethyl) aminosulfonyl)-2,4,6-trimethylphenyl]porphyrin;

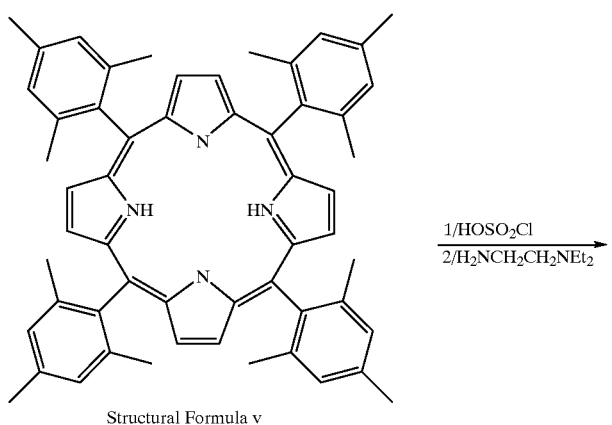

Structural Formula v

1/HOSO$_2$Cl
2/H$_2$NCH$_2$CH$_2$NEt$_2$
→

-continued
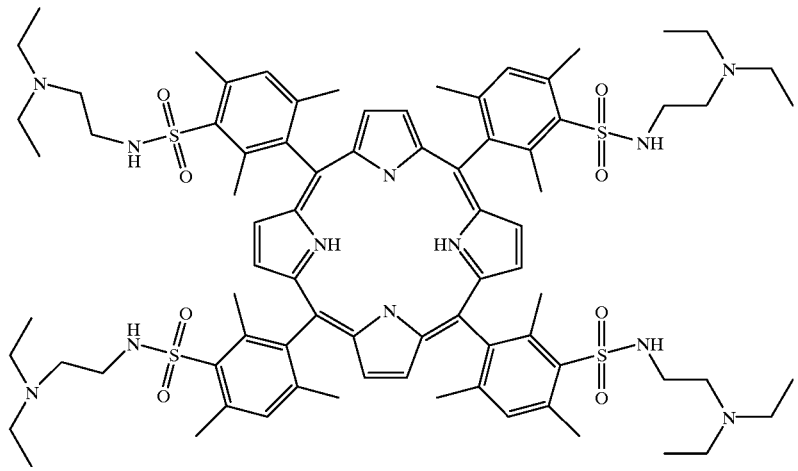
Structural Formula vi
(b) reacting first intermediate, Structural Formula vi, with Mn(OAc)$_2$ in the presence of hindered base thereby forming second intermediate, Structural Formula vii,
meso-tetrakis[3,(N-(2-(N,N-diethylamino)ethyl) aminosulfonyl)-2,4,6-trimethylphenyl]porphyrinato hydroxo-manganese (III); and
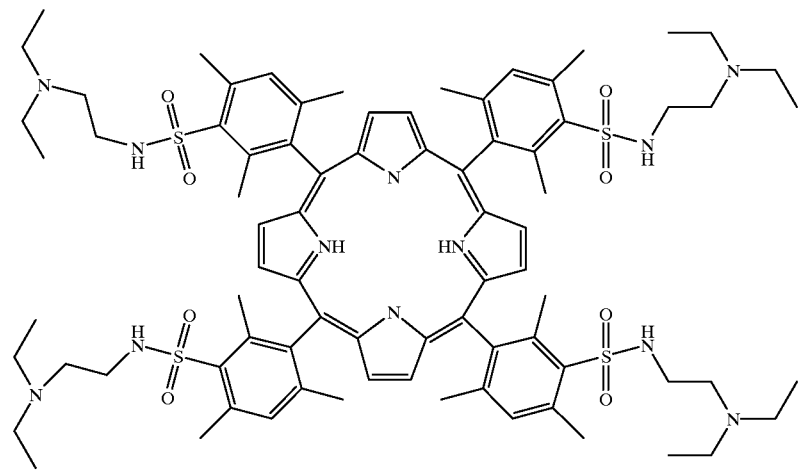
Structural Formula vi
Mn(OAc)$_2$
BASE

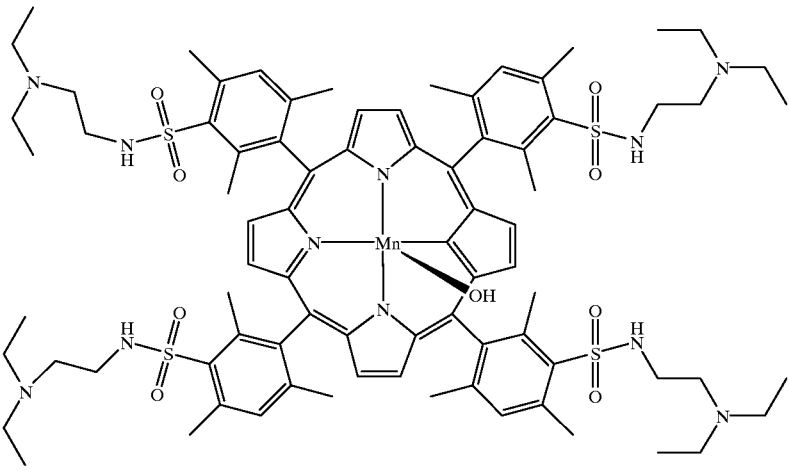
Structural Formula vii
(c) reacting second intermediate, Structural Formula vii, with hydrochloric acid thereby forming Structural Formula IV, meso-tetrakis[3-(N-(2-(N,N-diethylammonio) ethyl)aminosulfonyl)-2,4,6-trimethylphenyl] porphyrinato diaqua-manganese (III) pentachloride,
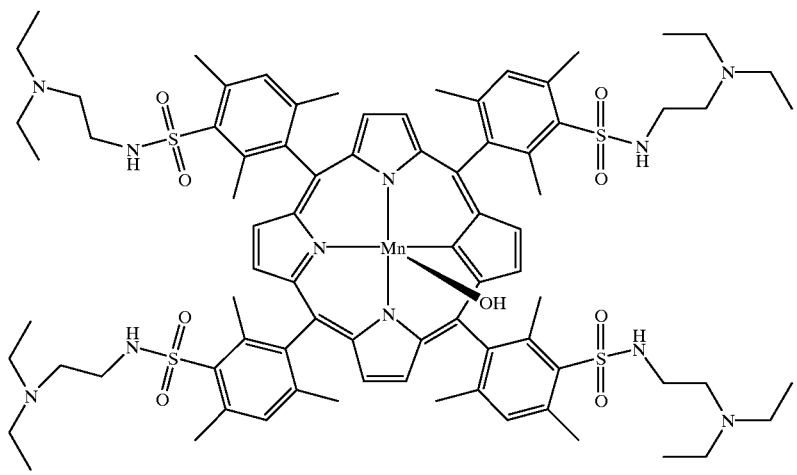
Structural Formula vii
↓ HCl 6M
  EtOH -continued

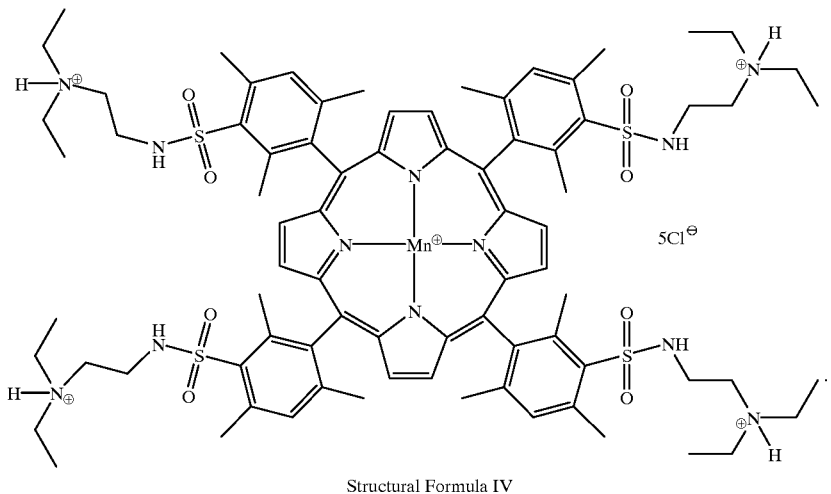

Structural Formula IV

35. A method of preparing compound meso-tetrakis[3-(N-(2-(N,N-diethylammonio)ethyl)aminosulfonyl)-2,4,6-trimethylphenyl]porphyrinato diaqua-iron(III) pentachloride represented by Structural Formula V comprising:

(a) reacting meso-tetrakis(2,4,6-trimethylphenyl) porphyrin, Structural Formula v, with chlorosulfonic acid and subsequently N,N-diethylenediamine thereby forming first intermediate, Structural Formula vi, meso-tetrakis[3,(N-(2-(N,N-diethylamino)ethyl) aminosulfonyl)-2,4,6-trimethylphenyl]porphyrin;

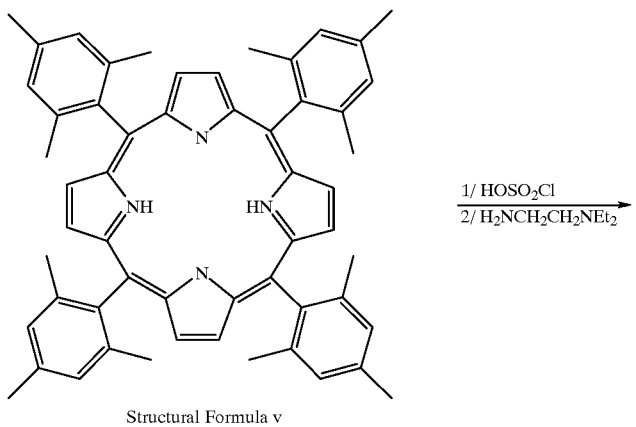

Structural Formula v

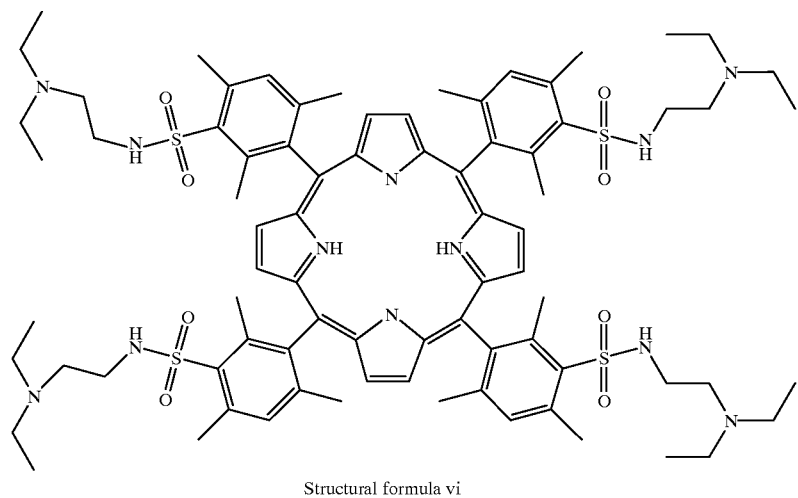

Structural formula vi (b) reacting first intermediate, Structural Formula vi, with ferrous chloride in the presence of a hindered base thereby forming second intermediate, Structural Formula viii, meso-tetrakis[3-N-(2-(N,N-diethylamino)ethyl)aminosulfonyl)-2,4,6-trimethylphenyl]porphyrinato hydroxo-iron (III); and

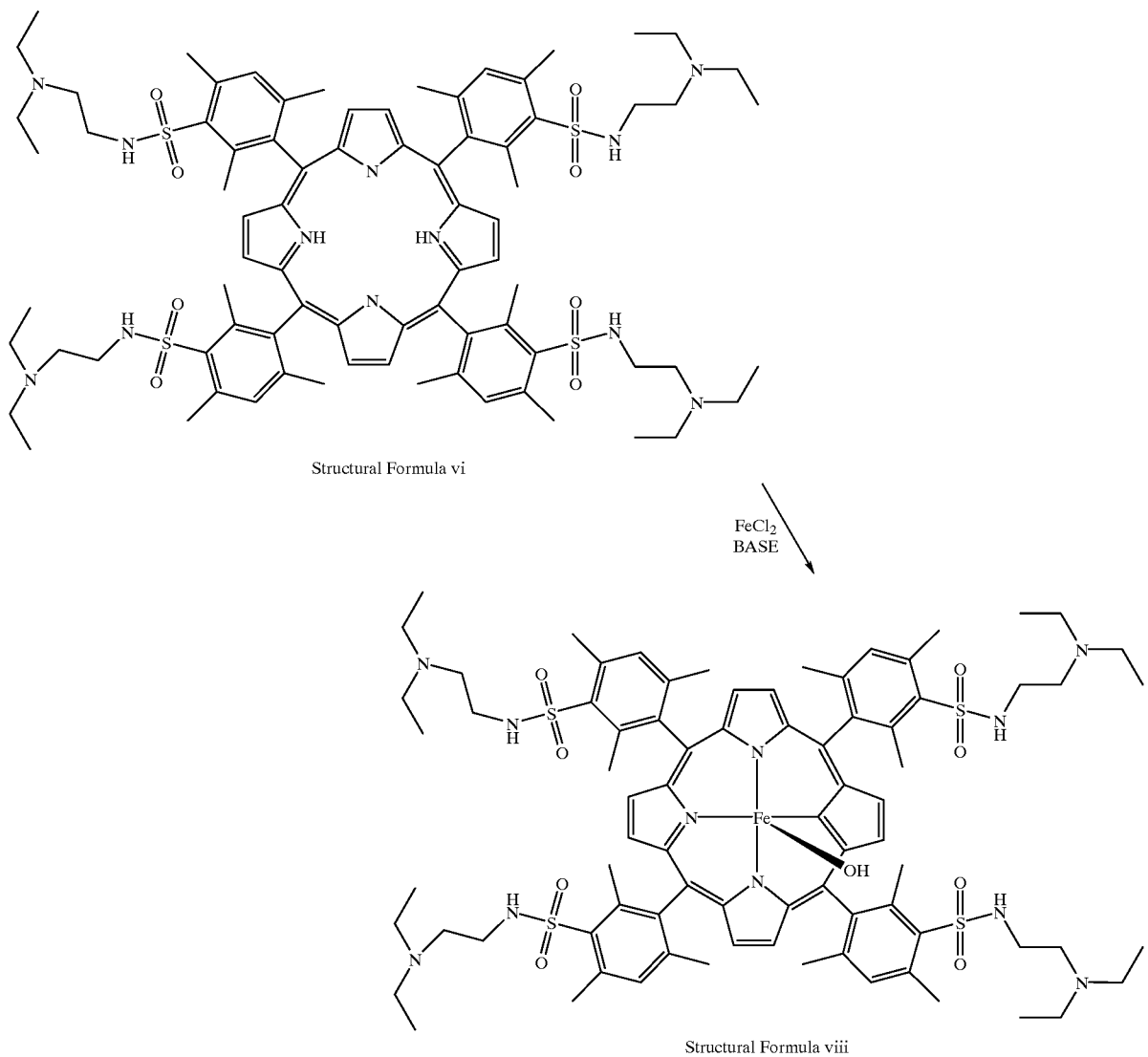

Structural Formula vi

Structural Formula viii (c) reacting second intermediate, Structural Formula viii, with hydrochloric acid thereby forming Structural Formula V, meso-tetrakis[3-(N-(2-(N,N-diethylammonio)ethyl)aminosulfonyl)-2,4,6-trimethylphenyl]porphyrinato diaqua-iron (III) pentachloride,

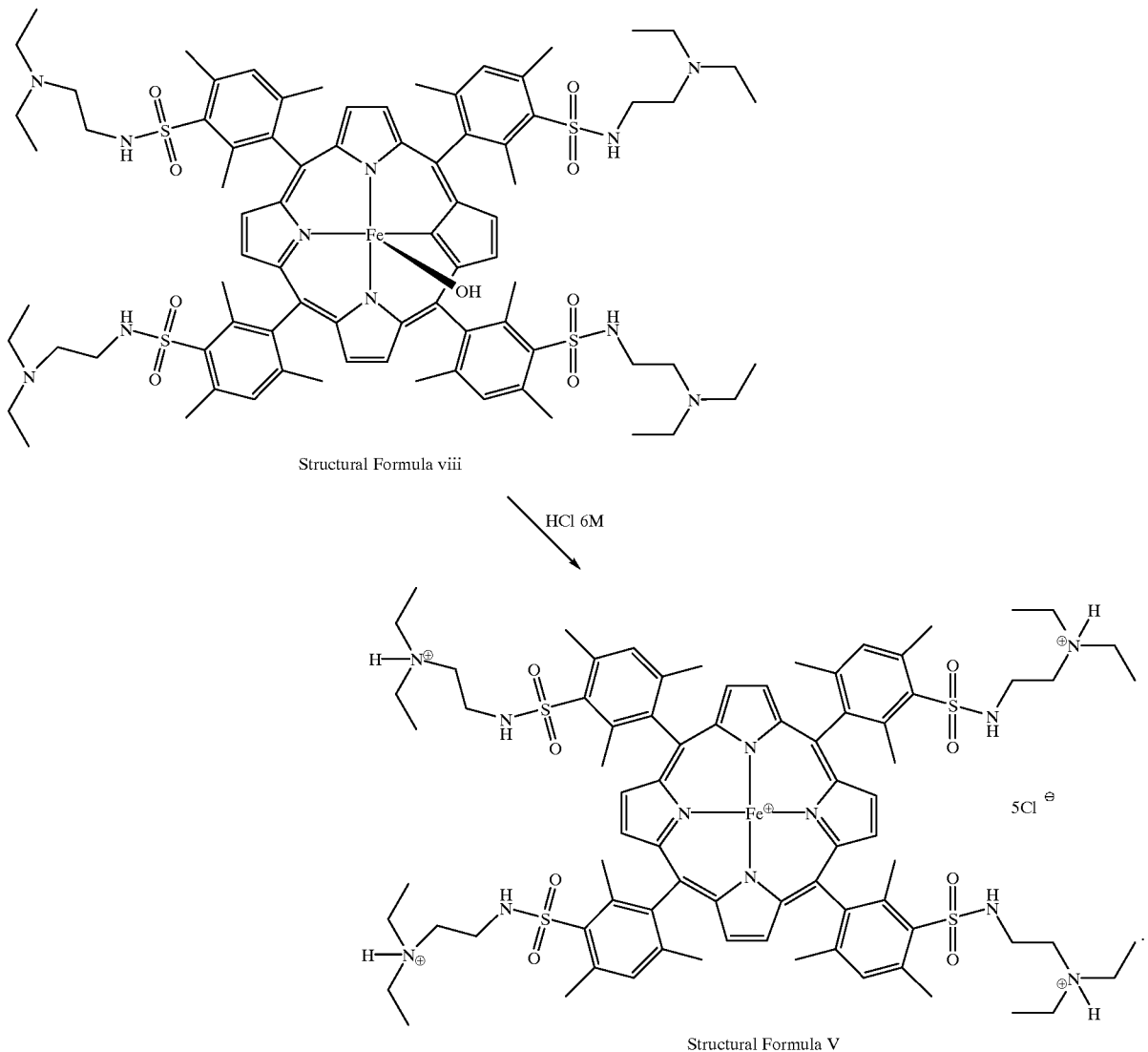

Structural Formula viii

HCl 6M

Structural Formula V

36. A method of preparing compound, meso-tetrakis[4-(N-(2-(N,N,N-diethylmethylammonio)ethyl)aminosulfonyl)phenyl]porphyrinato diaqua-manganese (III) pentaacetate, represented by Structural Formula VI, comprising:

(a) reacting meso-tetraphenyl porphyrin, Structural Formula i, with chlorosulfonic acid and subsequently N,N-diethylenediamine thereby forming first intermediate, Structural Formula ii, meso-tetrakis[4-(N-(2-(N,N-diethylamino)ethyl)aminosulfonyl)phenyl]porphyrin;

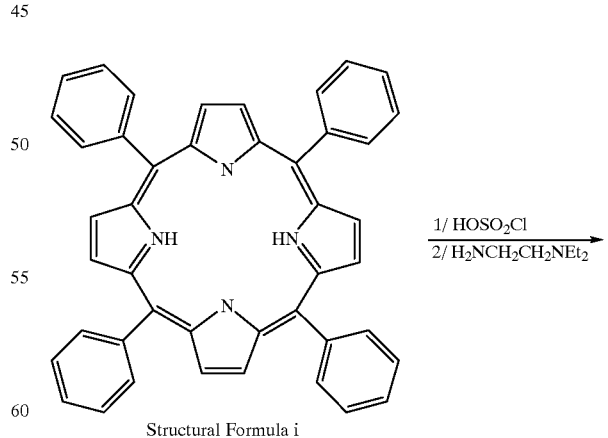

Structural Formula i

-continued
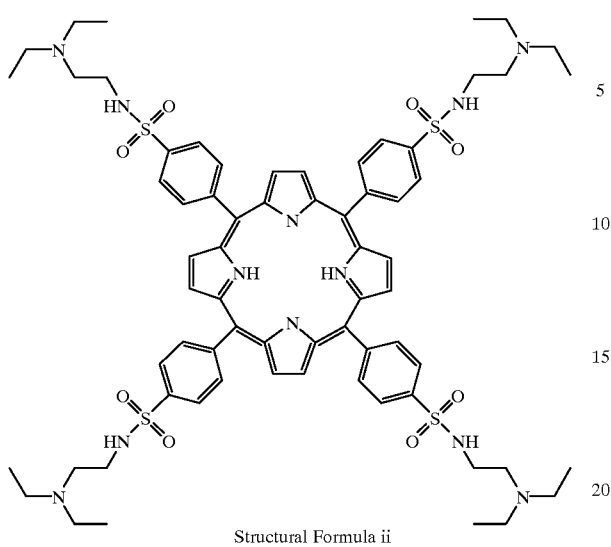
Structural Formula ii
(b) reacting first intermediate, Structural Formula ii, with Mn(OAc)$_2$ in the presence of hindered base, thereby forming second intermediate, Structural Formula iii, meso-tetrakis[4-(N-(2-(N,N-diethylamino)ethyl)aminosulfonyl)phenyl]porphyrinato hydroxomanganese (III);
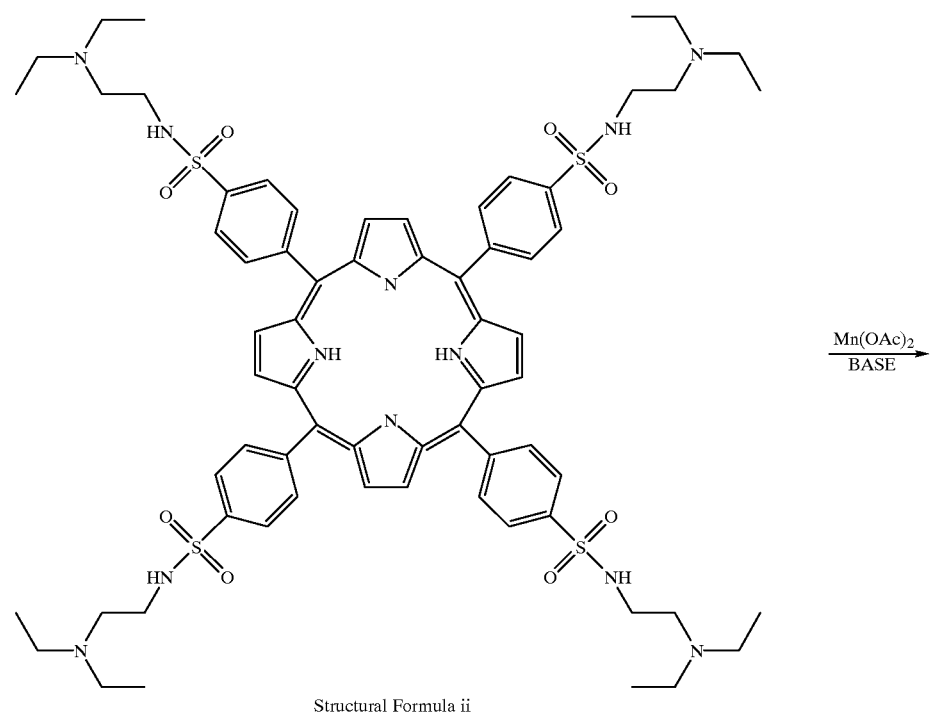
Structural Formula ii

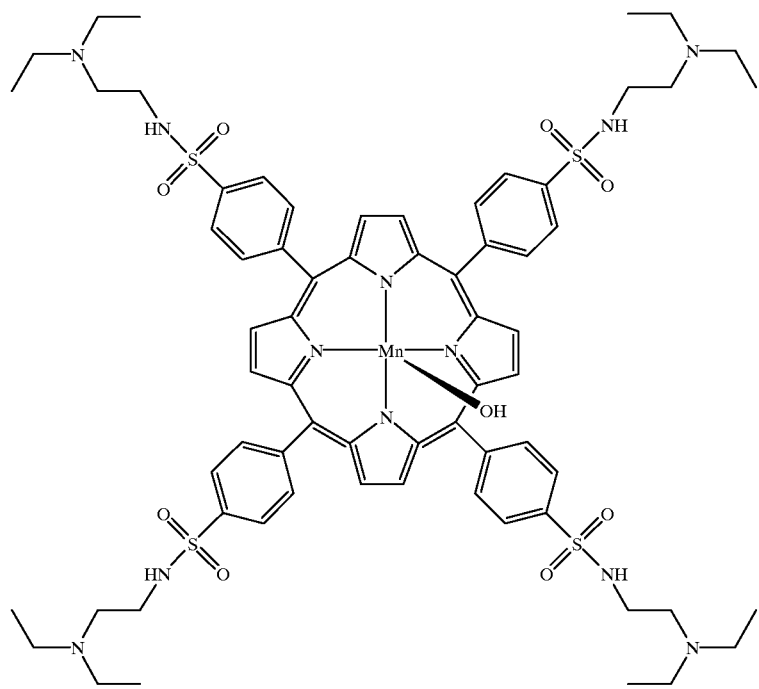
Structural Formula iii
(c) reacting second intermediate, Structural Formula iii, with methyl iodide thereby forming third intermediate, meso-tetrakis[4-(N-(2-(N,N,N,-diethylmethylammonio)ethyl)aminosulfonyl)phenyl] porphyrinato diaqua-manganese (III) pentaiodide, structural formula ix; and
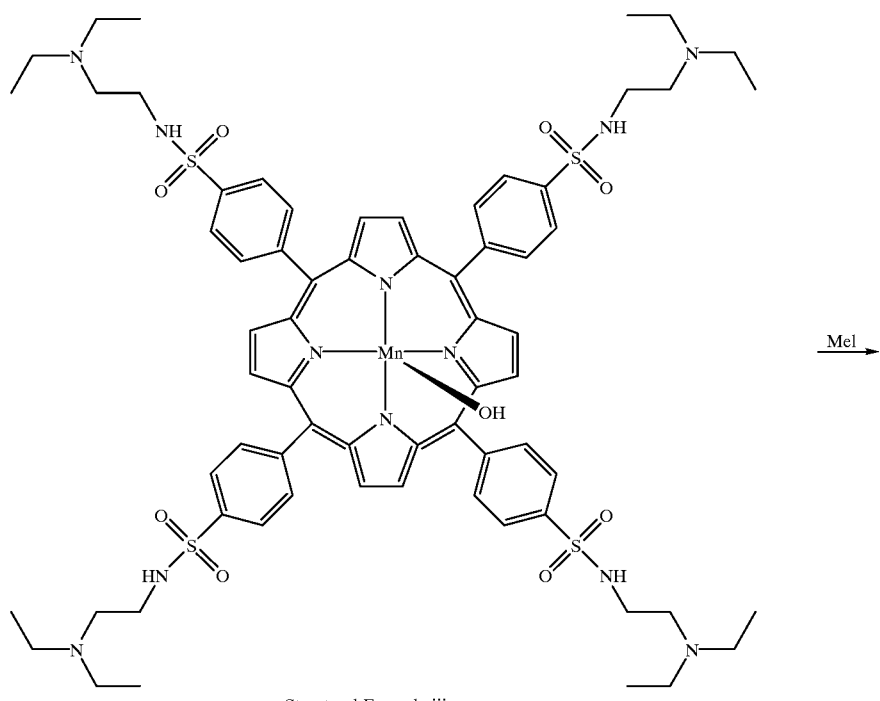
Structural Formula iii

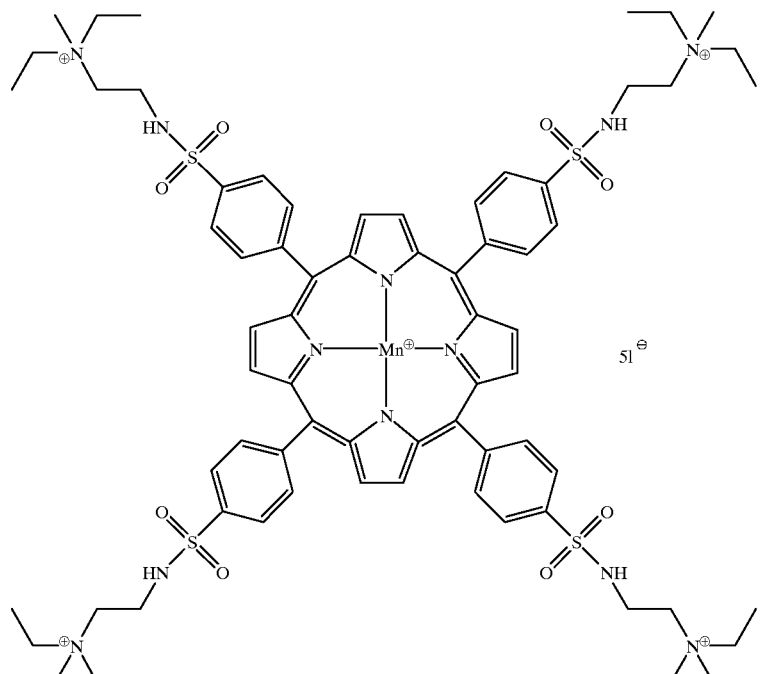
Structural Formula ix
(d) reacting Structural Formula ix with AGI-X8 acetate form resin to exchange the counter ion from iodide to acetate thereby forming Structural Formula VI, meso-tetrakis[4-(N-(2-(N,N,N-diethylmethylammonio)ethyl) aminosulfonyl)phenyl]porphyrinato diaqua-manganese (III) pentaacetate,
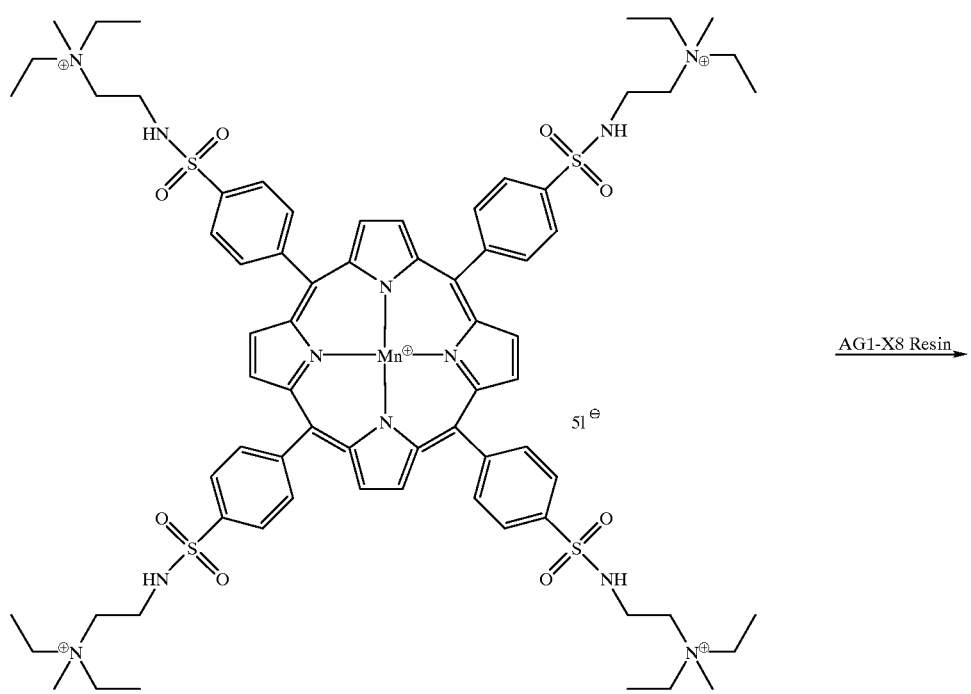
Structural Formula ix -continued

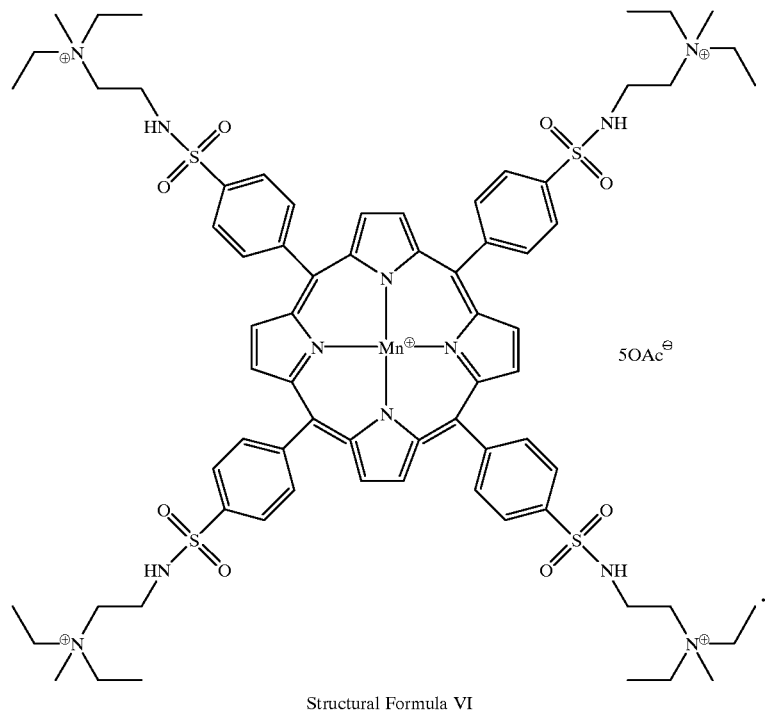

Structural Formula VI

37. A method of preparing compound, meso-tetrakis[3-(N-(2-(N,N,N-diethylmethylammonio)ethyl)aminosulfonyl)-2,4,6-trimethylphenyl]porphyrinato diaquamanganese (III) pentaacetate, represented by Structural Formula VII comprising:

(a) reacting meso-tetrakis (2,4,6-trimethylphenyl) porphyrin, Structural Formula v, with chlorosulfonic acid and subsequently N,N-diethylenediamine, thereby forming first intermediate, Structural Formula vi, meso-tetrakis[3,(N-(2-(N,N-diethylamino)ethyl)aminosulfonyl)-2,4,6-trimethylphenyl]porphyrin;

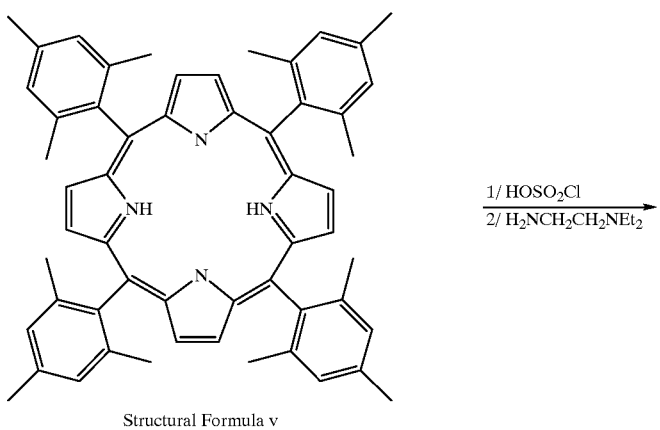

Structural Formula v

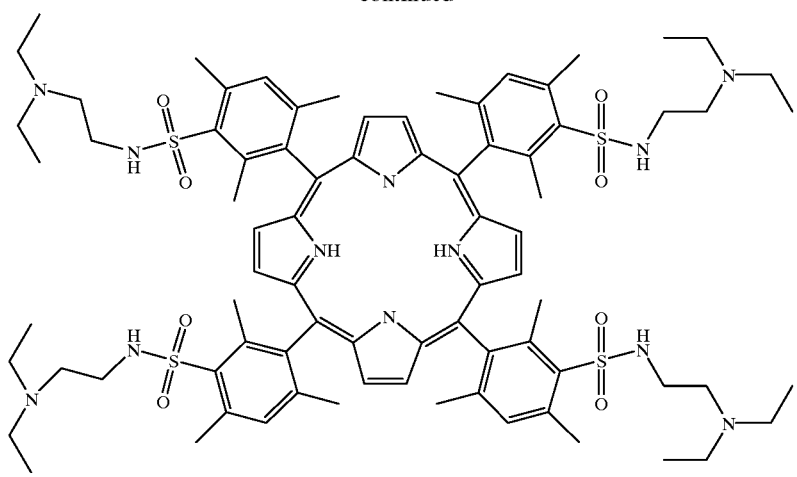
Structural Formula vi
(b) reacting first intermediate, Structural Formula vi, with Mn(OAc)$_2$ in the presence of a hindered base, thereby forming second intermediate, Structural Formula vii,
meso-tetrakis[3,(N-($^2$-(N,N-diethylamino)ethyl)aminosulfonyl)-2,4,6-trimethylphenyl]porphyrin hydroxo-manganese (III);
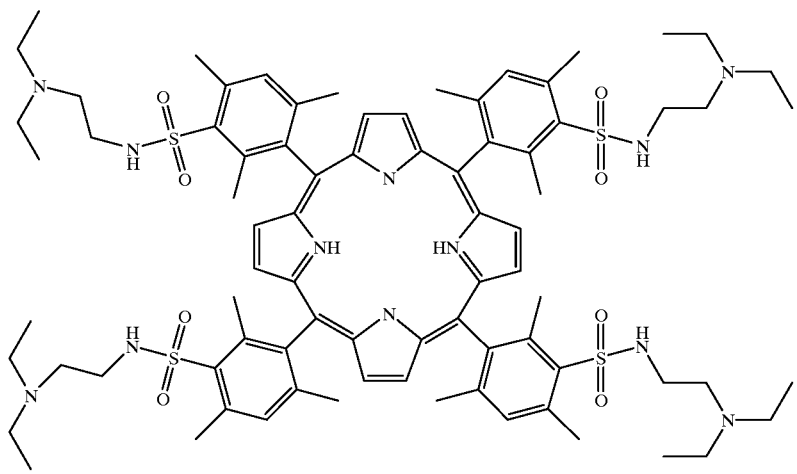
Structural Formula vi
Mn(OAc)$_2$
Base

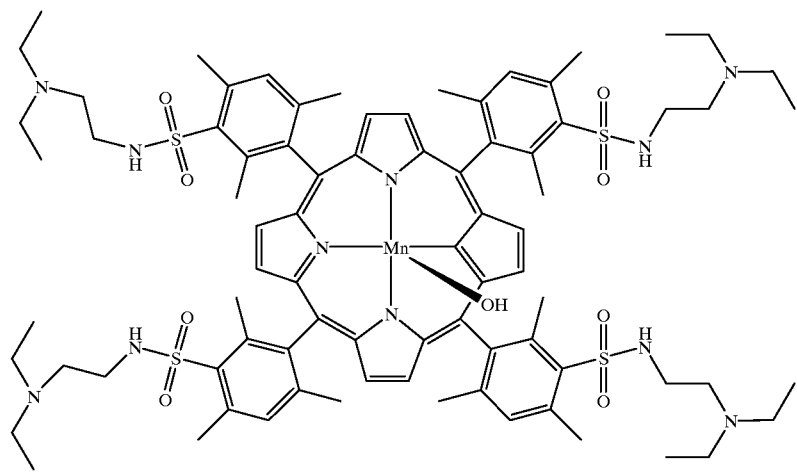
Structural Formula vii
(c) reacting second intermediate, Structural Formula vii, with methyl iodide thereby forming third intermediate, Structural Formula x, meso-tetrakis[3-(N-(2-(N,N,N,-diethylmethylammonio)ethyl)aminosulfonyl)-2,4,6-trimethylphenyl]porphyrinato diaqua-manganese (III) pentaiodide; and
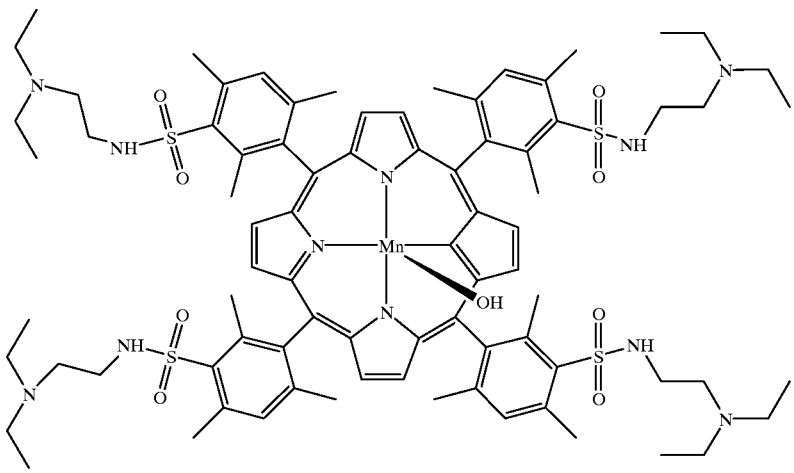
Structural Formula vii

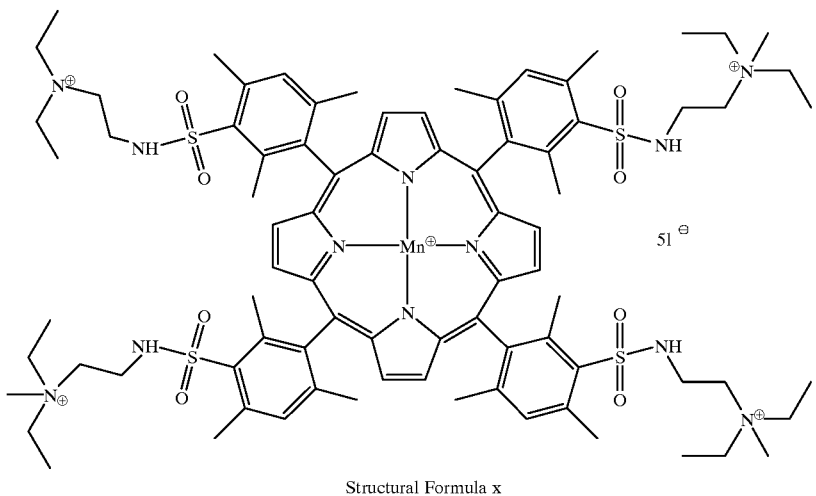

Structural Formula x (d) reacting third intermediate, Structural Formula x, with AGI-X8 acetate form resin to exchange the counter ion from iodide to acetate thereby forming meso-tetrakis [3-(N-(2-(N,N,N-diethylmethylammonio)ethyl) aminosulfonyl)-2,4,6-trimethylphenyl]porphyrinato manganese (III) pentaacetate represented by Structural Formula VII,

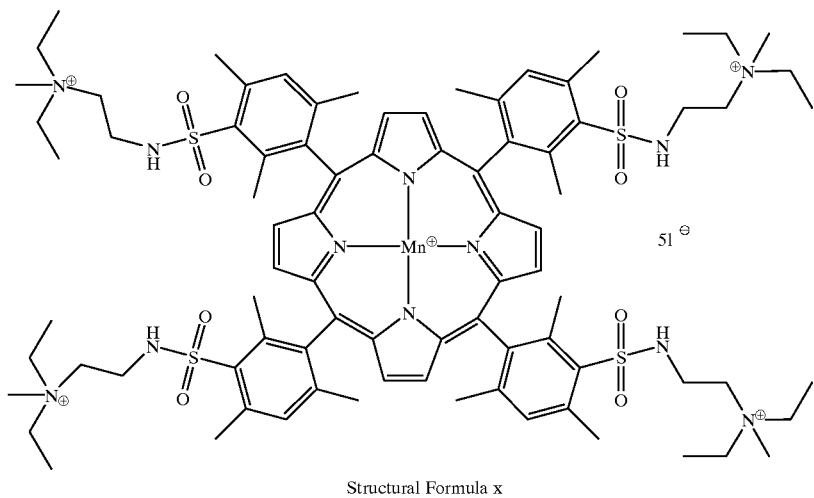

Structural Formula x

↓ AG1-X8 Resin

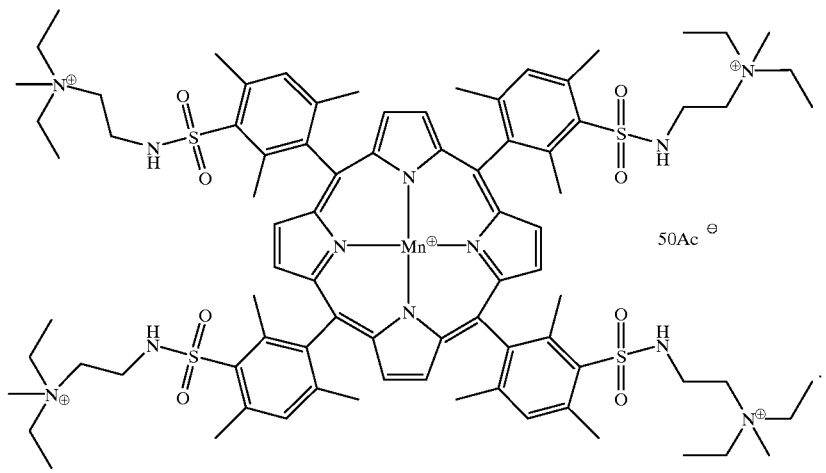

Structural Formula VII

38. A method of preparing compound, meso-tetrakis[3-(N-(2-(N,N,N,-diethylmethylammonio)ethyl)aminosulfonyl)2,4,6-trimethylphenyl]porphyrinato diaqua-iron (III) pentaacetate. Structural Formula VIII comprising;

(a) reacting meso-tetrakis(2,4,6-trimethylphenyl) porphyrin, Structural Formula v, with chlorosulfonic acid and subsequently N,N-diethylenediamine thereby forming first intermediate, Structural Formula vi, meso-tetrakis[3, (N-(2-(N,N-diethylamino)ethyl) aminosulfonyl)-2,4,6-trimethylphenyl]porphyrin;

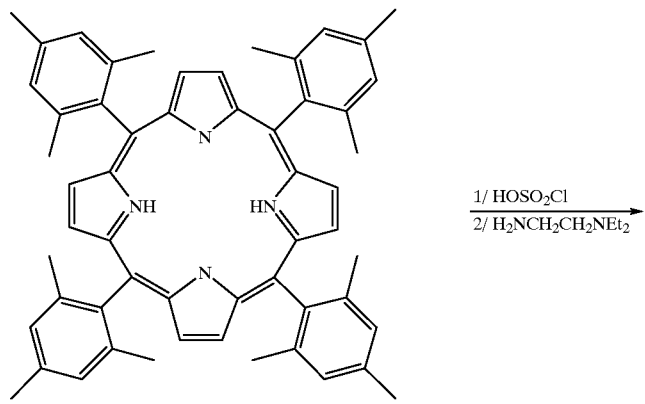

Structural Formula v

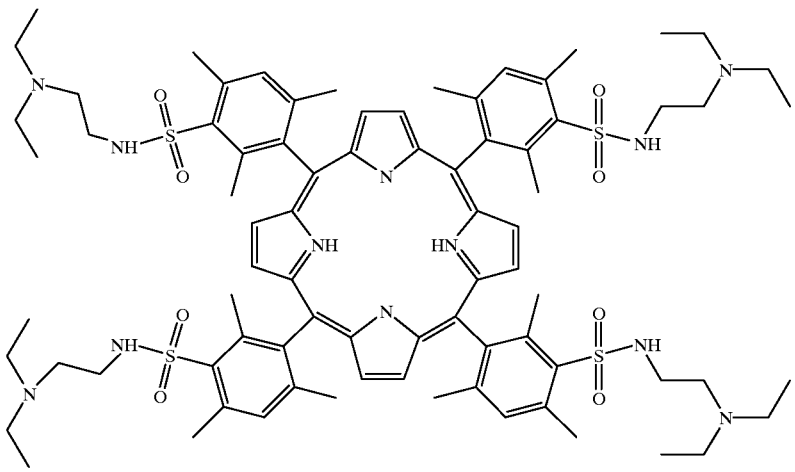
Structural formula vi
(b) reacting first intermediate, Structural formula vi, with ferrous chloride in the presence of a hindered base thereby forming second intermediate, Structural Formula viii, meso-tetrakis[3-(N-(2-(N,N-diethylamino)ethyl)aminosulfonyl)2,4,6-trimethylphenyl]porphyrinato hydroxo-iron (III);
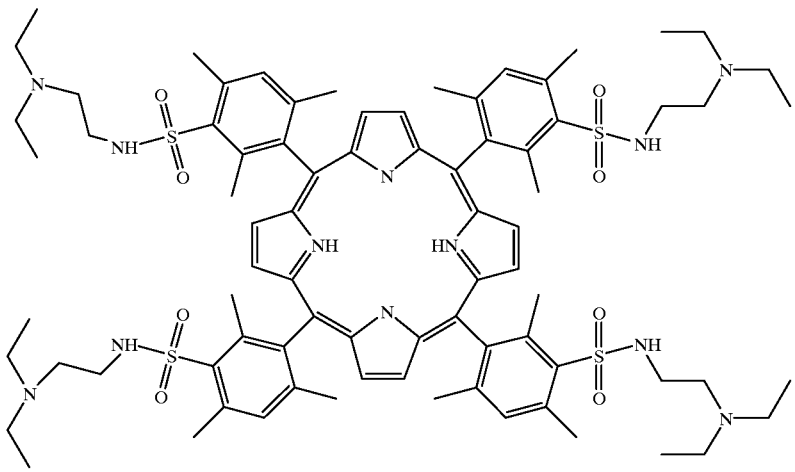
Structural Formula vi
FeCl₂
Base

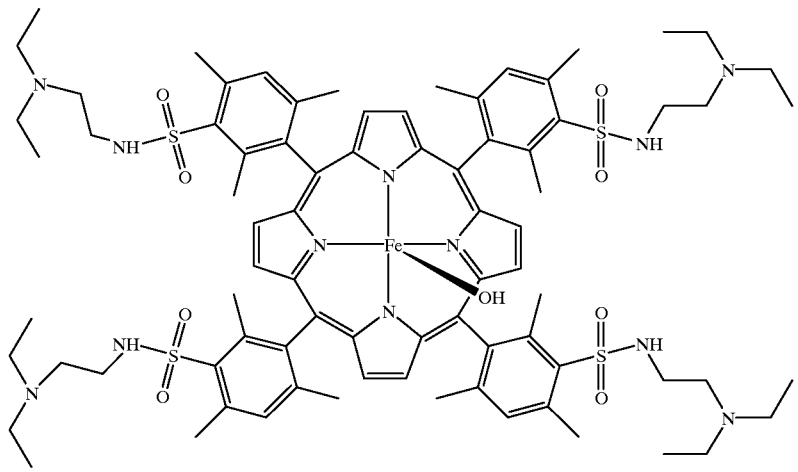

Structural Formula viii (c) reacting Structural Formula viii, meso-tetrakis[3-(N-(2-(N,N-diethylamino)ethyl)aminosulfonyl)2,4,6-trimethylphenyl]porphyrinato hydroxo-iron(III) with methyl iodide to form Structural Formula xi meso-tetrakis[3-(N-(2-(N,N,N-diethylmethylammonio)ethyl)aminosulfonyl)-2,4,6-trimethylphenyl]porphyrinato diaqua-iron (III) pentaiodide; and

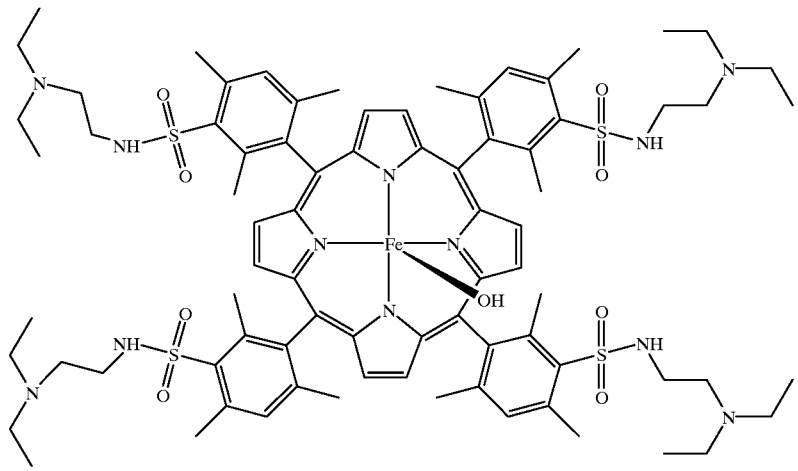

Structural Formula viii

↓ MeI

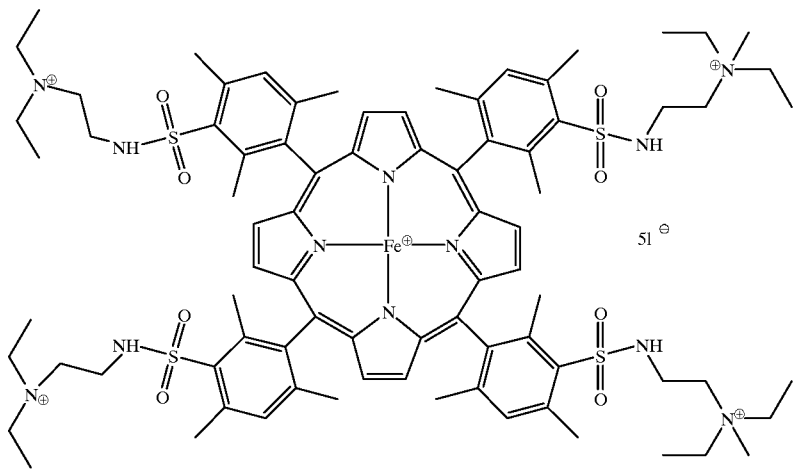

Structural Formula xi (d) reacting Structural Formula xi, meso-tetrakis[3-(N-(2-(N,N,N-diethylmethylammonio)ethyl)aminosulfonyl)-2,4,6-trimethylphenyl]porphyrinato diaqua-iron (III) pentaiodide, with AGI-X8 acetate form resin to exchange the counter ion from iodide to acetate thereby forming Structural Formula VIII, meso-tetrakis[3-(N-(2-(N,N,N,-diethylmethylammonio)ethyl) aminosulfonyl)-2,4,6-trimethylphenyl]porphyrinato diaqua-iron (III) pentaacetate,

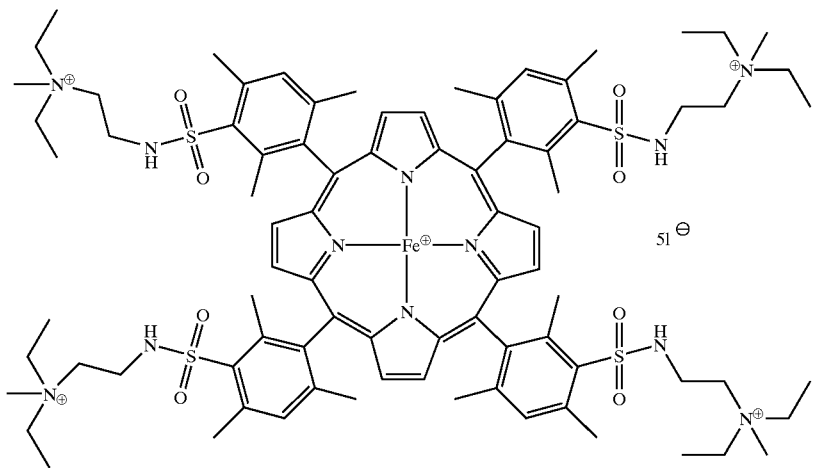

Structural Formula xi

AG1-X8 Resin

-continued

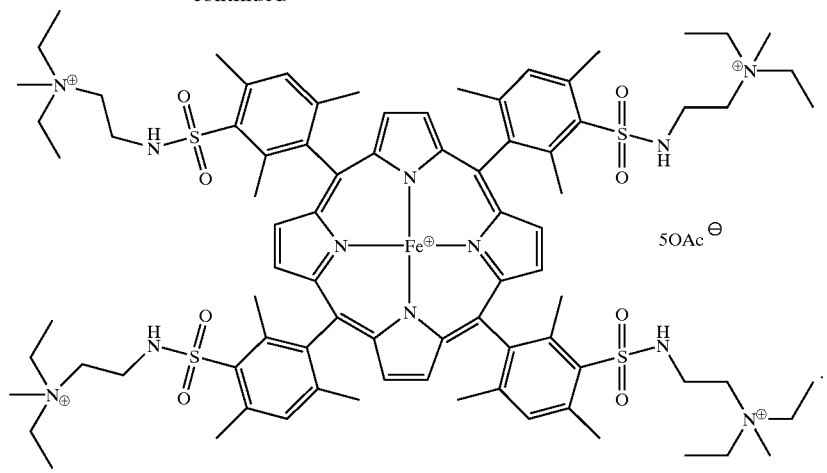

Structural Formula VIII

39. A method of reducing oxyradical- or reactive oxygen-induced damage to cells comprising introducing a compound of claim 1 to said cells wherein said introducing results in a decrease in the amount of free oxygen radical or nonradical reactive oxygen species in said cells when compared to not introducing said compound, wherein said decrease in the amount of free oxygen radical or nonradical reactive oxygen species reduces oxyradical- or reactive oxygen-induced damage to said cells.

* * * * *